United States Patent
Emery et al.

(10) Patent No.: US 9,623,076 B2
(45) Date of Patent: Apr. 18, 2017

(54) POLYPEPTIDES AND IMMUNIZING COMPOSITIONS CONTAINING GRAM POSITIVE POLYPEPTIDES AND METHODS OF USE

(71) Applicant: EPITOPIX, LLC, Willmar, MN (US)

(72) Inventors: Daryll A. Emery, New London, MN (US); Darren E. Straub, New London, MN (US); Lisa L. Herron-Olson, Minneapolis, MN (US); Laura Wonderling, Des Moines, IA (US)

(73) Assignee: EPITOPIX, LLC, Willmar, MN (US)

( * ) Notice: Subject to any disclaimer, the term of this patent is extended or adjusted under 35 U.S.C. 154(b) by 0 days.

(21) Appl. No.: 15/043,740

(22) Filed: Feb. 15, 2016

(65) Prior Publication Data

US 2016/0158312 A1 Jun. 9, 2016

Related U.S. Application Data

(63) Continuation of application No. 14/608,493, filed on Jan. 29, 2015, now Pat. No. 9,266,944, which is a continuation of application No. 13/362,992, filed on Jan. 31, 2012, now Pat. No. 8,961,979, which is a continuation of application No. 12/272,021, filed on Nov. 17, 2008, now Pat. No. 8,709,760, which is a continuation of application No. 11/353,459, filed on Feb. 14, 2006, now Pat. No. 8,007,811.

(60) Provisional application No. 60/652,843, filed on Feb. 14, 2005.

(51) Int. Cl.

| | |
|---|---|
| A61K 39/00 | (2006.01) |
| A61K 38/16 | (2006.01) |
| C07K 14/31 | (2006.01) |
| G01N 33/569 | (2006.01) |
| A61K 39/085 | (2006.01) |
| C07K 16/12 | (2006.01) |
| C07K 7/06 | (2006.01) |
| C07K 7/08 | (2006.01) |
| A61K 38/00 | (2006.01) |

(52) U.S. Cl.
CPC .......... *A61K 38/164* (2013.01); *A61K 39/085* (2013.01); *C07K 7/06* (2013.01); *C07K 7/08* (2013.01); *C07K 14/31* (2013.01); *C07K 16/1271* (2013.01); *C07K 16/1275* (2013.01); *C07K 16/1285* (2013.01); *C07K 16/1289* (2013.01); *G01N 33/56938* (2013.01); *A61K 38/00* (2013.01); *A61K 39/00* (2013.01); *A61K 2039/505* (2013.01); *C07K 2317/34* (2013.01); *C07K 2317/76* (2013.01); *Y10S 530/825* (2013.01)

(58) Field of Classification Search
None
See application file for complete search history.

(56) References Cited

U.S. PATENT DOCUMENTS

| | | |
|---|---|---|
| 4,981,685 A | 1/1991 | Healey |
| 5,538,733 A | 7/1996 | Emery et al. |
| 5,554,372 A | 9/1996 | Hunter |
| 5,830,479 A | 11/1998 | Emery et al. |
| 5,906,826 A | 5/1999 | Emery et al. |
| 6,027,736 A | 2/2000 | Emery et al. |
| 6,288,214 B1 | 9/2001 | Hook et al. |
| 6,432,412 B1 | 8/2002 | Emery et al. |
| 6,680,195 B1 | 1/2004 | Patti et al. |
| 6,682,754 B2 | 1/2004 | Emery et al. |
| 6,692,739 B1 | 2/2004 | Patti et al. |
| 6,703,025 B1 | 3/2004 | Patti et al. |
| 6,720,160 B2 | 4/2004 | Wolde-Mariam |
| 6,841,154 B2 | 1/2005 | Foster et al. |
| 7,138,124 B2 | 11/2006 | Emery et al. |
| 7,138,125 B2 | 11/2006 | Emery et al. |
| 7,147,857 B2 | 12/2006 | Emery et al. |
| 7,148,191 B2 | 12/2006 | Egyed et al. |
| 7,160,549 B2 | 1/2007 | Emery et al. |
| 7,341,732 B2 | 3/2008 | Emery et al. |
| 7,371,393 B2 | 5/2008 | Emery et al. |
| 7,413,743 B2 | 8/2008 | Emery et al. |
| 7,943,150 B2 | 5/2011 | Emery et al. |
| 7,943,151 B2 | 5/2011 | Emery et al. |
| 8,007,803 B2 | 8/2011 | Emery et al. |
| 8,007,811 B2 | 8/2011 | Emery et al. |
| 8,025,885 B2 | 9/2011 | Emery et al. |
| 8,119,147 B2 | 2/2012 | Emery et al. |
| 8,282,941 B2 | 10/2012 | Emery et al. |
| 8,425,916 B2 | 4/2013 | Emery et al. |
| 8,575,315 B2 | 11/2013 | Emery et al. |
| 8,637,048 B2 | 1/2014 | Emery et al. |
| 8,709,436 B2 | 4/2014 | Emery et al. |
| 8,709,760 B2 | 4/2014 | Emery et al. |

(Continued)

FOREIGN PATENT DOCUMENTS

| | | |
|---|---|---|
| WO | WO 90/12591 A1 | 11/1990 |
| WO | WO 95/21627 | 8/1995 |

(Continued)

OTHER PUBLICATIONS

U.S. Appl. No. 13/362,992, filed Jan. 31, 2012, Emery et al.
Extended European Search Report issued Aug. 22, 2012, in European Patent Application No. 10756718.2, filed Mar. 23, 2010.
International Search Report and Written Opinion for PCT application No. PCT/US2006/005058, Oct. 11, 2006; 17 pgs.
International Search Report and Written Opinion from PCT US2010-028326, dated Aug. 30, 2010; 13 pages.
International Preliminary Report on Patentability from PCT US2010-028326, dated Oct. 6, 2011; 10 pages.

(Continued)

*Primary Examiner* — Brian J Gangle
(74) *Attorney, Agent, or Firm* — Mueting, Raasch & Gebhart, PA

(57) ABSTRACT

The present invention provides isolated polypeptides isolatable from a *Staphylococcus* spp. Also provided by the present invention are compositions that include one or more of the polypeptides, and methods for making and methods for using the polypeptides.

26 Claims, 6 Drawing Sheets

(56) References Cited

U.S. PATENT DOCUMENTS

| | | | |
|---|---|---|---|
| 2002/0061569 | A1 | 5/2002 | Haselbeck et al. |
| 2003/0036639 | A1 | 2/2003 | Emery et al. |
| 2003/0064073 | A1 | 4/2003 | Emery et al. |
| 2003/0186364 | A1 | 10/2003 | Bailey et al. |
| 2005/0037444 | A1 | 2/2005 | Meinke et al. |
| 2005/0095682 | A1 | 5/2005 | Straub et al. |
| 2006/0115490 | A1 | 6/2006 | Masignani et al. |
| 2007/0128183 | A1 | 6/2007 | Meinke et al. |
| 2010/0111903 | A1 | 5/2010 | Emery et al. |
| 2012/0003269 | A1 | 1/2012 | Emery et al. |
| 2012/0195899 | A1 | 8/2012 | Emery et al. |
| 2013/0217048 | A1 | 8/2013 | Emery et al. |

FOREIGN PATENT DOCUMENTS

| | | | |
|---|---|---|---|
| WO | WO 96/01620 | A1 | 1/1996 |
| WO | WO 01/37810 | A2 | 5/2001 |
| WO | WO 01/37810 | A3 | 11/2001 |
| WO | WO 02/053180 | A2 | 7/2002 |
| WO | WO 02/059148 | A9 | 10/2002 |
| WO | WO 02/094868 | A2 | 11/2002 |
| WO | WO 02/053180 | A3 | 3/2003 |
| WO | WO 03/020875 | A2 | 3/2003 |
| WO | WO 03/020875 | A3 | 10/2003 |
| WO | WO 2004/013166 | A2 | 2/2004 |
| WO | WO 2004/013166 | A3 | 4/2004 |
| WO | WO 2006/021893 | A2 | 3/2006 |
| WO | WO 2006/021893 | A3 | 6/2006 |
| WO | WO 2006/059247 | A2 | 6/2006 |
| WO | WO 2006/088803 | A2 | 8/2006 |
| WO | WO 2006/088803 | A3 | 12/2006 |
| WO | WO 2010/111273 | A1 | 9/2010 |

OTHER PUBLICATIONS

Amorena et al., "Use of liposome-immunopotentiated exopolysaccharide as a component of an ovine mastitis staphococcal vaccine" Vaccine, 1994; 12(3):243-249.

Anderson et al., "*Staphylococcus aureus* Manganese Transport Protein C Is a Highly Conserved Cell Surface Protein That Elicits Protective Immunity Against *S. aureus* and *Staphylococcus epidermis*" The Journal of Infectious Diseases, Jun. 2012; 205:1688-1696.

Ando et al., "Characterization of the Role of the Divalent Metal Ion-Dependent Transcriptional Repressor MntR in the Virulence of *Staphylococcus aureus*" Infect. Immun., May 2003; 71(5):2584-90.

Anstead et al., "Recent Advances in the Treatment of Infections Due to Resistant *Staphylococcus aureus*" Curr. Opin. Infect., 2004; 17:549-555.

Ausubel et al., eds., Current Protocols in Molecular Biology, John Wiley & Sons, Inc., 1998; cover pg., publication pg., and table of contents only (12 pgs.).

Baba et al., "Genome and Virulence Determinants of High Virulence Community Acquired MRSA," Lancet, 2002; 359:1819-1827.

Baker et al., "Intravenous immune globulin for the prevention of nosocomial infection in low-birth-weight neonates," N. Engl. J. Med., Jul. 23, 1992; 327(4):213-9.

Bloom et al., "Multicenter Study to Assess Safety and Efficacy of INH-A21, a Donor-Selected Human Staphyococcal Immunoglobulin, for Prevention of Nosocomial Infections in Very Low Birth Weight Infants," Pediatr Infect Dis J., Oct. 2005; 24(10):858-66.

Bock et al., "Whole-proteome interaction mining," Bioinformatics, Jan. 2003;19(1):125-134.

Boulianne et al., "Production of functional chimaeric mouse/human antibody," Nature, Dec. 13-19, 1984; 312(5995):643-6.

Brouillette et al., "DNA immunization against the clumping factor A (C1fA) of *Staphylococcus aureus*," Vaccine, May 22, 2002; 20(17-18):2348-57.

Bruggeman et al., "Production of human antibody repertoires in transgenic mice," Curr. Opin. Biotechnol., Aug. 1997; 8(4):455-8.

Brown et al., "Characterization of Pit, a *Streptococcus pneumoniae* Iron Uptake ABC Transporter" Infect. Immun., Aug. 2002; 70(8):4389-98.

Bunce et al., "Murine Model of Cutaneous Infection with Gram-Positive Cocci" Infect. Immun., Jul. 1992; 60(7):2636-40.

Capparelli et al., "Multicenter Study to Determine Antibody Concentrations and Assess the Safety of Administration of INH-A21, a Donor-Selected Human *Staphylococcal* Immune Globulin, in Low-Birth-Weight Infants," Antimicrob Agents Chemother., Oct. 2005; 49(10):4121-7.

Cerca et al., "Protection Against *Escherichia coli* Infection by Antibody to the *Staphylococcus aureus* poly-N-acetylglucosamine Surface Polysaccharide," Proceedings of the National Academy of Sciences, May 1, 2007; 104(18) 7528-7533.

Clarke et al., "IsdA of *Staphylococcus aureus* is a broad spectrum, iron-regulated adhesin" Mol. Microbiol., Mar. 2004; 51(5):1509-19.

Clements et al. "Antibiotic Activity and Characterization of BB-3497, a Novel Peptide Deformylase Inhibitor", Antimicrob. Agents Chemother., Feb. 2001, 45(2):563-570.

Cockayne et al., "Molecular Cloning of a 32-Kilodalton Lipoprotein Component of a Novel Iron-Regulated *Staphylococcus epidermidis* ABC Transporter" Infect. Immun., Aug. 1998; 66(8):3767-74.

Colman, "Effects of amino acid sequence changes on antibody-antigen interactions" Research in Immunology, 1994; 145:33-36.

Cottrell et al., "Protein Identification by Peptide Mass Fingerprinting" Peptide Research, 1994; 7(3).

Courcol et al., "Effects of iron depletion and sub-inhibitory concentrations of antibiotics on siderophore production by *Staphylococcus aureus*," Journal of Antimicrobial Chemotherapy, 1991; 28:663-668.

Courcol et al., "Siderophore production by *Staphylococcus aureus* and identification of iron-regulated proteins," Infection and Immunity, May 1997; 65(5):1944-8.

Crichton, "Chapter 3. Microbial iron uptake and intracellular release" In: Inorganic Biochemistry of Iron Metabolism, Burgess, (ed)., 1991, Ellis Horwood Limited, Chichester, England, Title page and pp. 59-76.

Crosa, "The Relationship of Plasmid-Mediated Iron Transport and Bacterial Virulence," Annu. Rev. Microbiol., 1984; 38:69-89.

Crosa, "Genetics and Molecular Biology of Siderophore-Mediated Iron Transport in Bacteria," Microbiol. Rev., Dec. 1989; 53(4):517-530.

Dale et al., "Role of Siderophore Biosynthesis in Virulence of *Staphylococcus aureus*: Identification and Characterization of Genes Involved in Production of a Siderophore" Infect. Immun., Jan. 2004; 72(1):29-37.

Dale et al., "Involvement of SirABC in Iron-Siderophore Import in *Staphylococcus aureus*" J. Bacteriol., Dec. 2004; 186(24):8356-62.

Darenberg et al., "Differences in Potency of Intravenous Polyspecific Immunoglobulin G Against *Streptococcal* and *Staphylococcal* Superantigens: Implications for Therapy of Toxic Shock Syndrome," Clin Infect Dis., Mar. 15, 2004; 38(6):836-42.

Daugherty et al., "Polymerase chain reaction facilitates the cloning, CDR-grafting, and rapid expression of a murine monoclonal antibody directed against the CD18 component of leukocyte integrins," Nucleic Acids Res., May 11, 1991; 19(9):2471-6.

Definition of symptom and sign. Dorland's Medical Dictionary. Retrieved online Jun. 7, 2007 and Jun. 8, 2007. Retrieved from the Internet: <URL: http://mercksource.com>; 3 pgs.

Diarra et al., "Response of *Staphylococcus aureus* Isolates from Bovine Mastitis to Exogenous Iron Sources" J. Dairy Sci., 2002; 85(9):2141-8.

Domanski et al., "Characterization of a Humanized Monoclonal Antibody Recognizing Clumping Factor a Expressed by *Staphylococcus aureus*," Infect. Immun., Aug. 2005; 73(8):5229-32.

Drechsel et al., "Purification and chemical characterization of staphyloferrin B, a hydrophilic siderophore from staphylococci" Biometals, 1993; 6:185-92.

Dryla et al., "Identification of a novel iron regulated staphylococcal surface protein with haptoglobin-haemoglobin binding activity" Mol. Microbiol., Jul. 2003; 49(1):37-53.

Durfee, "Classification of 110 Strains of *Staphylococcus aureus*" J. Bacteriol., Nov. 1942; 44(5):589-95.

Ellis, "New Technologies for Making Vaccines", Chapter 29 of Vaccines, Philadelphia, PA, 1988, cover page, copyright page, and p. 568-575; 10 pages total.

(56) References Cited

OTHER PUBLICATIONS

Fattom et al., "Developement of StaphVAX, a polysaccharide conjugate vaccine against S. aureus infection: from the lab bench to phase III clinical trials," Vaccine, Feb. 17, 2004; 22(7):880-7.
Ferguson et al., "Siderophore-Mediated Iron Transport: Crystal Structure of FhuA with Bound Lipopolysaccharide," Science, Dec. 18, 1998;282(5397):2215-2220.
Finkelstein et al., "Role of Iron in Microbe-Host Interactions," Rev. Infect. Dis., Sep.-Oct. 1983;5 Suppl 4: S759-776.
Foster et al., "Surface protein adhesins of Staphylococcus aureus" Trends Microbiol., 1998; 6:Title page, Publication page, and pp. 484-488.
Furugouri, "Iron Binding Substances in the Intestinal Mucosa of Neonatal Piglets," J Nutr. Mar. 1977; 107(3):487-494.
Gampfer et al., "Epitope mapping of neutralizing TSST-1 specific antibodies induced by immunization with toxin or toxoids," Vaccine, Nov. 1, 2002; 20(31-32):3675-84.
Geret et al., "Vaccination against staphylococcal infections in animal experiments," Helvetica Chirurgica Acta, May 1979; 46(1-2):167-169.
Giddings et al., "Genome-based peptide fingerprint scanning" PNAS, 2003; 100(1):20-25.
Gilleland, Jr. et al., "Perspectives on the Potential for Successful Development of Outer Membrane Protein Vaccines," Eur. J. Clin. Microbiol., Jun. 1987;6(3):231-233. (0039 added "Review. (No abstract available.)").
Greenbaum et al., "Towards a Consensus on Datasets and Evaluation Metrics for Developing B-cell epitope Prediction Tools," Journal of Molecular Recognition, 2007; (20)2:75-82.
Greenspan et al., "Defining Epitopes: It's not as easy as it seems" Nature Biotechnology, Oct. 1999; 17:936-937.
Hall et al., "Characterization of a Protective Monoclonal Antibody Recognizing Staphylococcus aureus MSCRAMM Protein Clumping Factor A," Infect. Immun., Dec. 2003; 71(12):6864-70.
Harlow et al., Antibodies, A Laboratory Manual, Cold Spring Harbor Laboratory, Cold Spring Harbor, NY, 1988; generally and Chapter 5.
Harlow et al., Antibodies, A Laboratory Manual, Cold Spring Harbor Laboratory, Cold Spring Harbor, NY, 1988; cover page, copyright page and pp. 23-25, 27-33.
Heinrichs et al., "Identification and characterization of SirA, an iron-regulated protein from Staphylococcus aureus" J. Bacteriol., Mar. 1999; 181(5):1436-43.
Henzel et al., "Identifying proteins from two-dimensional gels by molecular mass searching of peptide fragments in protein sequence databases" PNAS USA, 1993; 90:5011-5015.
Herbert, Dictionary of Immunology, Fourth Edition, Academic Press, 1995, pp. 58-59.
Herron-Olson, Lisa, "Molecular correlates of host-specific adaptation in Staphylococcus aureus associated with bovine mastitis and human toxic shock syndrome," A Dissertation submitted to the Faculty of the Graduate School of the University of Minnesota, Jul. 2005; 200 pgs.
Hill, "Additional confirmation of the lack of effect of intravenous immunoglobulin in the prevention of neonatal infection" J. Pediatr., Nov. 2000; 137(5):595-7.
Hill et al., "SirR, a Novel Iron-Dependent Repressor in Staphylococcus epidermis" Infect. Immun., Sep. 1998; 66(9):4123-9.
Holden et al., "Complete genomes of two clinical Staphylococcus aureus strains: Evidence for the rapid evolution of virulence and drug resistance," Proceedings of the National Academy of Sciences of USA, National Academy of Science, Jun. 29, 2004; 101(26):9786-9791.
Horsburgh et al., "In Staphylococcus aureus, Fur Is an Interactive Regulator with PerR, Contributes to Virulence, and Is Necessary for Oxidative Stress Resistance through Positive Regulation of Catalase and Iron Homeostasis" J. Bacteriol., Jan. 2001; 183(2):468-75.
Houghten et al., "Relative importance of position and individual amino acid residues in peptide antigen-antibody interactions: Implications in the mechanism of antigenic drift and antigenic shift" Vaccines 86, New Approaches to Immunization, Cold Spring Harbor Laboratory, Cold Spring Harbor, NY, 1986; cover page, copyright page, and pp. 21-25.
Hussain et al., "A Lithium Chloride-Extracted, Broad-Spectrum-Adhesive 42-Kilodalton Protein of Staphylococcus epidermidis is Ornithine Carbomoylotransferase" [online] Infection and Imunnity, Dec. 1999; 67(12):6688-90. [retrieved on Jul. 12, 2002]. Retrieved from the Internet:<URL:http://iai.asm.org/cgi/content/full/67/12/6668?view=full&pmid=10569792> . 8 pgs.
Jiang et al., "Ligand-Specific Opening of a Gated-Porin Channel in the Outer Membrane of Living Bacteria," Science, May 1997, 276:1261-1264.
Joiner et al., "A Quantitative Model for Subcutaneous Abscess Formation in Mice" Br. J. Exp. Pathol. Feb. 1980; 61(1):97-107.
Jones et al., "Replacing the complementarity-determining regions in a human antibody with those from a mouse," Nature, May 29-Jun. 4, 1986; 321(6069): 522-525.
Kaplan, "Treatment of Community-Associated Methicillin-Resistant Staphylococcus aureus Infections" The Pediatric Infectious Disease Journal, May 2005; 24(5):457-458.
Kim et al., "IsdA and IsdB antibodies protect mice against Staphylococcus aureus abscess formation and lethal challenge," Vaccine, Aug. 31, 2010; 28(38):6382-6392.
Koebnik et al., "Structure and function of bacterial outer membrane proteins: barrels in a nutshell," Molecular Microbiology, 2000, 37/2:239-253.
Konetschny-Rapp et al., "Staphyloferrin A: a structurally new siderophore from staphylococci" Eur. J. Biochem., 1990; 191:65-74.
Kuklin et al., "A novel Staphylococcus aureus Vaccine: Iron Surface Determinant B Induces Rapid Antibody Response in Rhesus Macaques and Specific Increased Survival in a Murine S. aureus Sepsis Model," Infection and Immunity, Apr. 2006;74(4):2215-2223.
Leitner et al., "Development of a Staphylococcus aureus vaccine against mastitis in dairy cows. II. Field trial" Veterinary Immunology and Immunopathology, 2003; 93:153-8.
Liebler, Introduction to Proteomics: Tools for the New Biology, Humana Press, Totowa, NJ, 2002; title page, copyright page, and pp. 77-82.
Lin et al., "Th1-Th17 Cells Mediate Protective Adaptive Immunity against Staphylococcus aureus and Candida albicans Infection in Mice," PLOS Pathogens, Dec. 2009; 5(12):1-10.
Lindsay et al., "Staphylococcus aureus but not Staphylococcus epidermidis can acquire iron from transferrin" Microbiology, Jan. 1995; 141(Pt 1):197-203.
Lindsay et al., "Staphylococcal iron requirements, siderophore production, and iron-regulated protein expression" Infection and Immunity, Jun. 1994; 62(6):2309-14.
Lipman et al., "Rapid and sensitive protein similarity searches" Science, 1985; 227:1435-1441.
LoBuglio et al., "Mouse/human chimeric monoclonal antibody in man: Kinetics and immune response," Proc. Natl. Acad. Sci. USA, Jun. 1989; 86(11):4220-4.
Lonberg et al., "Antigen-specific human antibodies from mice comprising four distinct genetic modifications," Nature, Apr. 28, 1994; 368(6474):856-9.
Lonberg et al., "Human Antibodies from Transgenic Mice," Int. Rev. Immunol., 1995; 13(1):65-93.
Lowell et al., "Immunogenicity and Efficacy against Lethal Aerosol Staphylococcal Enterotoxin B Challenge in Monkeys by Intramuscular and Respiratory Delivery of Proteosome-Toxoid Vaccines," Infect. Immun., Nov. 1996; 64(11):4686-93.
Maira-Litrán et al. "Immunochemical Properties of the Staphylococcal Poly-N-Acetylglucosamine Surface Polysaccharide," Infect. Immun., Aug. 2002; 70(8):4433-40.
Maira-Litrán et al. "Biologic properties and vaccine potential of the stphylococcal poly-N-acetyl glucosamine surface polysaccharide," Vaccine, Feb. 17, 2004; 22(7):872-9.
Maira-Litrán et al. "Comparative Opsonic and Protective Activities of Staphylococcus aureus Conjugate Vaccines Containing Native or Deacetylated Staphylococcal Poly-N-Acetyl-β-(1-6)-Glucosamine," Infect. Immun., Oct. 2005; 73(10):6752-62.

(56) References Cited

OTHER PUBLICATIONS

Mazmanian et al., "Passage of Heme-Iron Across the Envelope of *Staphylococcus aureus*" Science, Feb. 7, 2003; 299(5608):906-9.
Mazmanian et al., "An iron-regulated sortase anchors a class of surface protein during *Staphylococcus aureus* pathogenesis" Proc. Natl. Acad. Sci. USA, Feb. 19, 2002; 99(4):2293-8.
McKenney et al., "Broadly Protective Vaccine for *Staphylococcus aureus* Based on an in Vivo-Expressed Antigen," Science, May 28, 1999; 284(5419):1523-7.
McKenney et al., "Vaccine potential of poly-1-6 beta-D-N-succinylglucosamine, an immunoprotective surface polysaccharide of *Staphylococcus aureus* and *Staphylococcus epidermidis*" J. Biotechnol., Sep. 29, 2000; 83(1-2):37-44.
Mendoza et al., "Identification of *Staphyloccus* species by 16S-23S rDNA intergenic spacer PCR analysis" I'ntl J. Systematic Bacteriology, 1998; 48:1049-1055.
Menzies et al., "Inhibition of *Staphylococcal* Wound Infection and Potentiation of Antibiotic Prophylaxis by a Recombinant Fragment of the Fibronectin-Binding Protein of *Staphylococcus aureus*," J. Infect Dis., Apr. 1, 2002; 185(7):937-43.
Miller et al., "Ensuring the pathogen safety of intravenous immunoglobulin and other human plasma-derived therapeutic proteins," J. Allergy Clin Immunol., Oct. 2001; 108(4 suppl):S91-4.
Modun et al., "The *Staphylococcus aureus* and *Staphylococcus epidermidis* transferrin-binding proteins are expressed in vivo during infection" Microbiology, Apr. 1998; 144(Pt 4):1005-12.
Modun et al., "Staphylococci Express a Receptor for Human Transferrin: Identification of a 42-Kilodalton Cell Wall Transferrin-Binding Protein" Infect. Immun., Sep. 1994; 62(9):3850-8.
Morrissey et al., "The *Staphylococcal* Ferritins are Differentially Regulated in Response to Iron and Manganese and via PerR and Fur" Infect. Immun., Feb. 2004; 72(2):972-9.
Morrissey et al., "Conservation, Surface Exposure, and In Vivo Expression of the Frp Family of Iron-Regulated Cell Wall Proteins in *Staphylococcus aureus*" Infect. Immun., May 2002; 70(5):2399-407.
Morrissey et al., "Molecular Cloning and Analysis of a Putative Siderophore ABC Transporter from *Staphylococcus aureus*" Infect. Immun., Nov. 2000; 68(11):6281-8.
Morrison et al., "Chimeric human antibody molecules: Mouse antigen-binding domains with human constant region domains," Proc. Natl. Acad. Sci. USA, Nov. 1984; 81(21) 6851-5.
NCBI (National Center for Biotechnology Information) accession No. YP_416181/GI: 825750440, first available Nov. 29, 2005.
NCBI (National Center for Biotechnology Information) accession No. NP_373946.1/GI:15926413, first available Oct. 4, 2001.
Neilands, "Microbial Iron Compounds," Ann. Rev. Biochem., 1981; 50:715-731.
Neilands, "Microbial Envelope Proteins Related to Iron," Ann. Rev. Microbiol., 1982; 36:285-309.
Nilsson et al. "Vaccination with a Recombinant Fragment of Collagen Adhesion Provides Protection Against *Staphylococcus aureus*-mediated Septic Death," J Clin Invest., Jun. 1998; 101(12):2640-9.
Ohwada et al., "DNA vaccination by mecA sequence evokes an antibacterial immune response against methicillin-resistant *Staphylococcus aureus*," J. Antimicrob. Chemother., Dec. 1999; 44(6):767-74.
Pengov et al., "Antimicrobial Drug Susceptibility of *Staphylococcus aureus* Strains Isolated from Bovine and Ovine Mammary Glands" J.Dairy Sci, 2003; 86:3157-3163.
Perkins et al., "Probability-based protein identification by searching sequence databases using mass spectrometry data" Electrophoresis, Dec. 1999; 20(18):3551-3567.
Poelstra et al., "Surgical Irrigation with Pooled Human Immunoglobulin G to Reduce Post-Operative Spinal Implant Infection," Tissue Eng., Aug. 2000; 6(4): 401-11.
Poutrel et al., "Reactivity of Coagulase-Negative Staphylococci Isolated from Cow and Goat Milk with Monoclonal Antibodies to *Staphylococcus aureus* Capsular Polysaccharide Types 5 and 8" J. Clinical Microbiology, 1990;28(2):358-360.
Projan et al., "*Staphylococcal* vaccines and immunotherapy: to dream the impossible dream?" Current Opinion in Pharmacology, 2006; 6:473-479.
Queen et al., "A humanized antibody that binds to the interleukin 2 receptor," Proc. Natl. Acad. Sci. USA, Dec. 1989; 86(24):10029-33.
Reinoso et al., "Bovine and rabbit models for the study of a *Staphylococcus aureus* avirulent mutant strain, RC122," Can J. Vet Res., Oct. 2002; 66(4):285-8.
Riechmann et al., "Reshaping human antibodies for therapy," Nature, Mar. 24, 1988; 332(6162):323-7.
Sacher, "Intravenous immunoglobulin consensus statement," J. Allergy Clin Immunol., Oct. 2001;108(4 Suppl):S139-46.
Schlievert, "Use of intravenous immunoglobulin in the treatment of *staphylococcal* and *streptococcal* toxic shock syndromes and related illnesses," J. Allergy Clin Immunol., Oct. 2001; 108(4 Suppl): S107-10.
Sebulsky et al., "Identification and Characterization of fhuD1 and fhuD2, Two Genes Involved in Iron-Hydroxamate Uptake in *Staphylococcus aureus*" J. Bacteriol., Sep. 2001; 183(17):4994-5000.
Sebulsky et al., "Identification and Characterization of a Membrane Permease Involved in Iron-Hydroxamate Transport in *Staphylococcus aureus*" J. Bacteriol., Aug. 2000; 182(16):4394-400.
Senna et al., "Protective immune response against methicillin resistant *Staphylococcus aureus* in a murine model using a DNA vaccine approach," Vaccine, Jun. 2, 2003; 21(19-20):2661-6.
Smith et al., "Environmentally regulated genes of *Streptococcus suis*: identification by the use of iron-restricted conditions in vitro and by experimental infection of piglets" Microbiology, Feb. 2001; 147(Pt 2):271-280.
Spellberg et al., "The Antifungal Vaccine Derived from the Recombinant N Terminus of A1s3p Protects Mice against the Bacterium *Staphylococcus aureus*," Infection and Immunity, Oct. 2008; 76(10):4574-4580.
*Staphylococcal* Infections. Merck Manual Home Edition. Retrieved online Jun. 7, 2007. Retrieved from the Internet: <URL:http://www.merck.com/mmhe>; 2 pgs.
Stiles et al., "Mucosal Vaccination with Recombinantly Attenuated *Staphylococcal* Enteroxin B and Protection in a Murine Model," Infect. Immun., Apr. 2001; 69(4):2031-6.
Stohl et al., "Human T Cell-Dependent B Cell Differentiation Induced by *Staphylococcal* Superantigens," J. Immunol., Jul. 1, 1994; 153(1):117-27.
Stohl et al., "Differential Human T Cell-Dependent B Cell Differentiation Induced by *Staphylococcal* Superantigens (SAg). Regulatory Role for SAg-Dependent B Cell Cytolysis," J. Immunol., Aug. 15, 1995; 155(4):1838-50.
Stohl et al., "In Vitro Inhibition by Intravenous Immunoglobulin of Human T Cell-Dependent B Cell Differentiation Induced by *Staphylococcal* Superantigens," Clin Immunol Immunopathol., May 1996; 79(2):122-33.
Stoppler et al., "Staph Infection (*Staphylococcus aureus*)" [online]. MedicineNet, Inc., San Clemente, CA, Copyright 2008 [retrieved Mar. 6, 2008]. Retrieved from the internet: <URL:http://www.medicinenet.com/script/main/ art.asp?articlekey=1991&pf=3&page=2>; 4 pgs.
Stranger-Jones,"Vaccine assembly from surface proteins of *Staphylococcus aureus*," PNAS USA, Nov. 7, 2006; 103(45):16942-16947.
Takei et al., "Intravenous Immunoglobulin Contains Specific Antibodies Inhibitory to Activation of T Cells by *Staphylococcal* Toxin Superantigens," J. Clin Invest., Feb. 1993; 91(2):602-7.
Taylor et al., "A transgenic mouse that expresses a diversity of human sequence heavy and light chain immunoglobulins," Nucleic Acids Res., Dec. 11, 1992; 20(23):6287-95.
Tatusova et al., "BLAST 2 Sequences, a new tool for comparing protein and nucleotide sequences," FEMS Microbiol Lett., May 15, 1999; 174(2):247-50.

(56) References Cited

OTHER PUBLICATIONS

Todar's Online Textbook of Bacteriology, "The Bacterial Flora of Humans", 2002. Retrieved online May 11, 2007. Retrived from the Internet: <URL: http//www.textbookofbacteriology.net/normalflora.html>; 20 pgs.
Trivier et al., "Influence of iron depletion on growth kinetics, siderophore production, and protein expression of *Staphylococcus aureus*" FEMS Microbiol. Lett., Apr. 1, 1995; 127(3): 195-9.
van der Helm, "Physical Biochemistry of FEPA and other Siderophore Receptor Proteins," J. Inorg. Biochem., 1995;59(2-3):90 (abstract only).
van der Zee et al., "Molecular Genotyping of *Staphylococcus aureus* Strains: Comparison of Repetitive Element Sequence-Based PCR with Various Typing Methods and Isolation of a Novel Epidemicity Marker" Journal of Clinical Microbiology, Feb. 1999;37(2):342-349.
Verhoef et al. "Prospects for monoclonal antibodies in the diagnosis and treatment of bacterial infections" Eur. J. Clin. Microbiol. Infect. Dis., 1990; 9(4):247-250.
Verhoeyen et al., "Reshaping Human Antibodies: Grafting an Antilysozyme Activity," Science, Mar. 25, 1988; 239(4847):1534-6.
Vernachio et al., "Anti-Clumping Factor a Immunoglobulin Reduces the Duration of Methicillin-Resistant *Staphylococcus aureus* Bacteremia in an Experimental Model of Infective Endocarditis," Antimicrob Agents Chemother., Nov. 2003; 47(11):3400-6.
Vytvytska et al., "Identification of vaccine candidate antigens of *Staphylococcus aureus* by serological proteome analysis," Proteomics, 2002; 2:580-590.
Wysocki et al., "Receptors for Endogenous and Heterogenous Hydroxamate Siderophores in *Staphylococcus aureus* B 47[1]" Pol. J. Microbiol., 2005; 54:97-103.
Xiong et al., "Molecular characterization of the ferric-uptake regulator, Fur, from *Staphylococcus aureus*" Microbiology, 2000; 146(Pt 3):659-68.

Figure 3    Kaplan-Meier survival curve showing percent survival after vaccination and homologous challenge with S. aureus ATCC19636
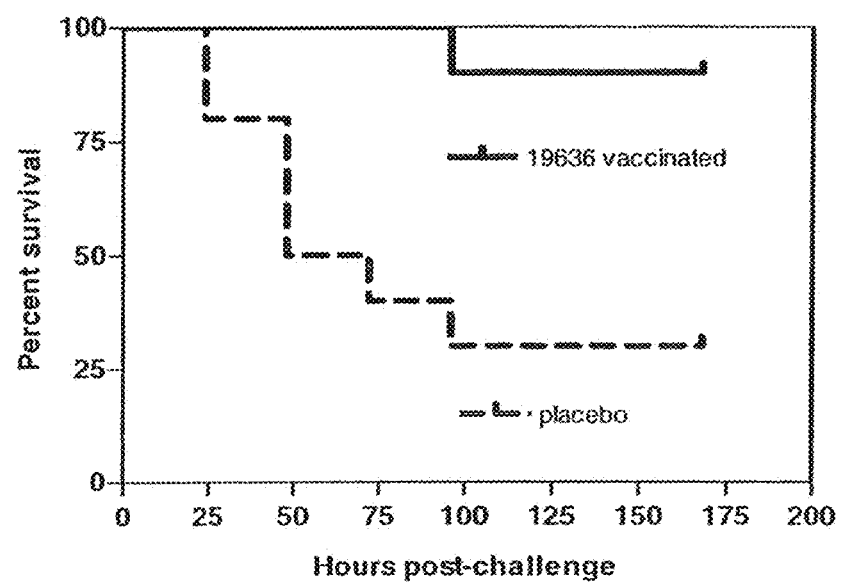

Figure 4   Kaplan-Meier survival curve showing percent survival after vaccination and heterologous challenge with *S. aureus* ATCC19636
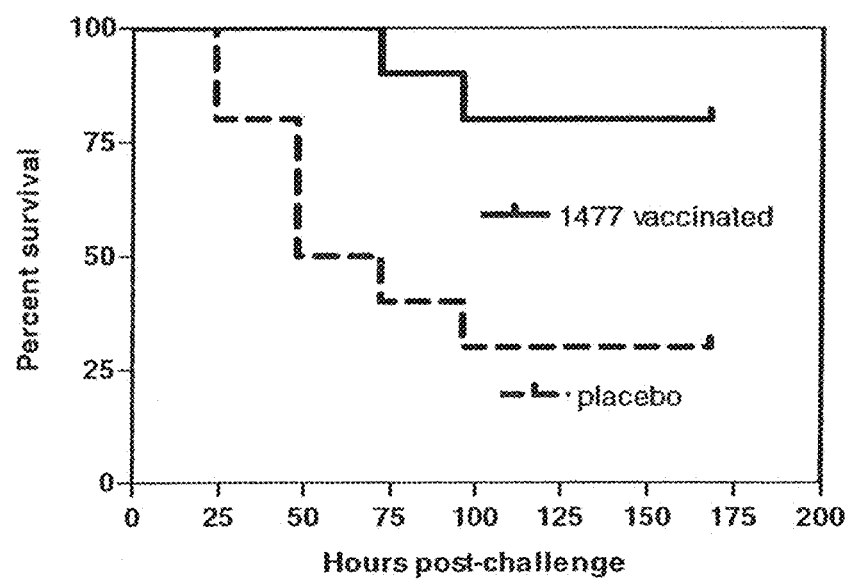

Figure 5  Kaplan-Meier survival curve showing percent survival after passive immunization and homologous challenge with *S. aureus* ATCC19636
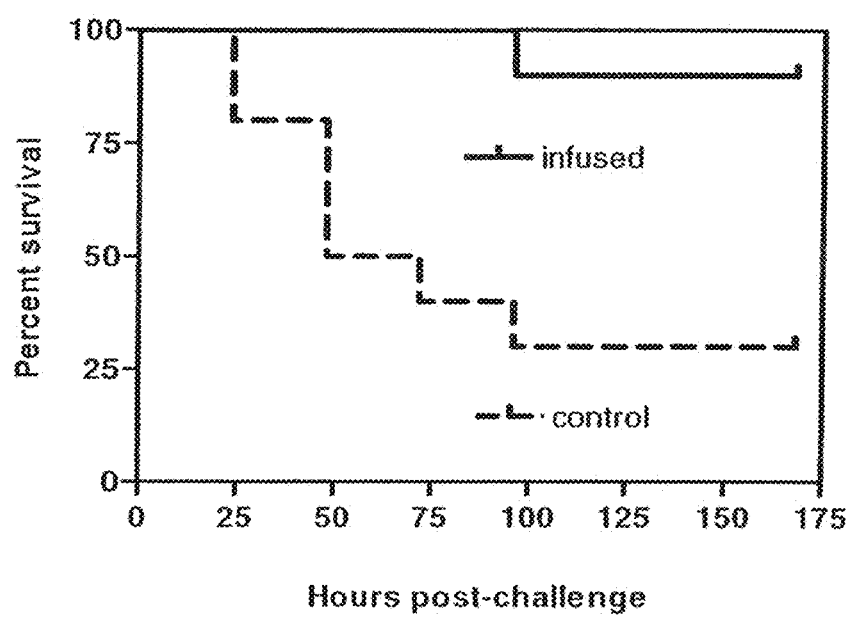

Figure 6     Kaplan-Meier survival curve showing percent survival after passive immunization and heterologous challenge with *S. aureus* 1477
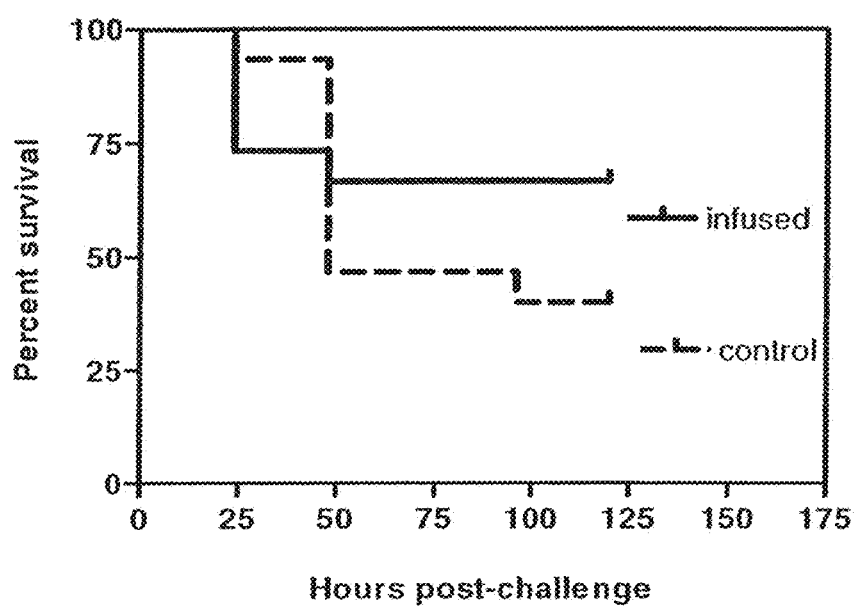

POLYPEPTIDES AND IMMUNIZING COMPOSITIONS CONTAINING GRAM POSITIVE POLYPEPTIDES AND METHODS OF USE

CONTINUING APPLICATION DATA

This application is a continuation patent application of U.S. patent application Ser. No. 14/608,493, filed on Jan. 29, 2015 (now U.S. Pat. No. 9,266,944), which is a continuation patent application of U.S. patent application Ser. No. 13/362,992, filed on Jan. 31, 2012, (now U.S. Pat. No. 8,961,979), which is a continuation patent application of U.S. patent application Ser. No. 12/272,021, filed on Nov. 17, 2008 (now U.S. Pat. No. 8,709,760), which is a continuation of U.S. patent application Ser. No. 11/353,459, filed on Feb. 14, 2006 (now U.S. Pat. No. 8,007,811), which claims the benefit of U.S. Provisional Application No. 60/652,843, filed Feb. 14, 2005, each of which is incorporated by reference herein.

SEQUENCE LISTING

This application contains a Sequence Listing electronically submitted via EFS-Web to the United States Patent and Trademark Office as an ASCII text file entitled "29300380106SequenceListg_ST25.txt," having a size of 85 kilobytes and created on Feb. 15, 2016. The information contained in the Sequence Listing is incorporated by reference herein.

BACKGROUND

Gram-positive bacteria are a remarkably diverse group of organisms that cause a variety of diseases in both humans and animals. Some of the pathogens recognized as important in human and/or animal health include bacteria belonging to the families of Corynebacteriaceae, Enterococcacae, Micrococcaceae, Mycobacteriaceae, Nocardiaceae, and Peptococcaceae, which include such bacterial species as *Actinomyces* spp., *Bifidobacterium* spp., *Corynebacterium* spp., *Enterococcus* spp., *Erysipelothrix* spp. *Eubactrerium* spp., *Kytococcus* spp., *Lactobacillus* spp., *Micrococcus* spp., *Mobiluncus* spp., *Mycobacteria* spp., *Peptostreptococcus* spp., *Propionibacterium* spp., and *Staphylococcus* spp. These pathogens cause a multitude of clinical manifestations in many different animal species. The treatment for such infections has historically been antibiotics that attack the common structures and functions of gram-positive organisms. However, many of the more ubiquitous gram-positive organisms have developed resistance to several classes of antibiotics, making treatment of infections difficult. The widespread use of antibiotics in the treatment of bacterial diseases in both humans and food production animals is likely a major contributing factor in the proliferation of antibiotic-resistant strains of many species of gram-positive organisms. Therefore, there is a great need to find different treatments that prevent or eliminate infections by gram-positive organisms in animals as well as humans.

Staphylococcal Infections in Agricultural Animals

In the agricultural industry a number of important diseases are caused by gram-positive organisms. Examples of clinical conditions caused by gram positive bacterial infections include, mastitis, septicemia, pneumonia, osteomyclitis, meningoencephalitis, lymphangitis, dermatitis, genital tract infections, metritis, perinatal disease, pituitary abscesses, arthritis, bursitis, orchitis, cystitis and pyelonephritis, caseous lymphadenitis, tuberculosis, ulcerative lymphangitis, erysipelas, laminitis, tyzzer's disease, tetanus, botulism, enteritis, malignant edema, braxy, bacillary hemoglobinuria, enterotoxemia. *Staphylococcus* spp., in particular, are capable of infecting many different species of agricultural animals and can cause enormous economic losses. For example, the United States dairy industry is estimated to lose approximately $185 per cow annually due to mastitis, a disease often caused by *Staphylococcus aureus*. Since there are 9.5 million head of milking cows in the U.S., the annual cost of mastitis is approximately $1.8 billion. This is approximately 10% of the total value of farm milk sales, and about two-thirds of this loss is due to reduced milk production in sub-clinically infected cows. Other losses are due to discarded abnormal milk and milk withheld from cows treated with antibiotic, costs of early replacement of affected cows, reduced sale value of culled cows, costs of drugs and veterinary services, and increased labor costs. In addition to its prevalence within the bovine dairy industry, mastitis caused by gram-positive cocci is also common among goats and sheep. Additional animal diseases caused by *S. aureus* include botryomycosis in horses, purulent synovitis and osteomyelitis in poultry, snuffles in rabbits, abortions in swine, and tick pyemia in lambs. Other species of staphylococci are major skin pathogens of canine (*S. intermedius*) and swine (*S. hycius*). In poultry species, staphylococcal pathogens cause endorcarditis and septicemia.

Staphylococcal Infections in Humans

*Staphylococcus* spp. are also human pathogens causing a wide variety of infections. The species *Staphylococcus aureus*, a common colonizer of human mucosa and skin, is an opportunistic pathogen that can cause diverse human infections. For example, *S. aureus* is the causative agent of several skin infections, including impetigo, furunculosis, cellulitus, and scalded skin syndrome, as well as potentially fatal post-surgical wound infections. In addition, the exposure of immunocompromised individuals to *S. aureus* in hospital settings has resulted in organ infections such as pneumonia, urinary tract infections, osteomyelitis, arthritis, bacteremia, and endocarditis. *S. aureus* is also the causative agent of toxinoses, most notably toxic shock syndrome and food poisoning. Food poisoning caused by the staphylococcal enterotoxin B is the most common cause of food-borne illness, surpassing even *salmonellosis*, campylobacteriosis and listeriosis. Other species of staphylococci also cause human disease; *S. epidermidis, S. haemolyticus* and *S. hominis* commonly infect implanted medical devices and *S. saprophyticus* is associated with urinary tract infections in women.

Virulence Mechanisms of Staphylococci

Staphylococci infect a variety of host tissues and evade the immune system through the production of several types of secreted proteins, surface expressed virulence factors and metabolic systems designed for survival amidst the limited resources and active defenses associated with the host environment. Colonization is the necessary first step in establishing infection; numerous factors including capsule, lipoteichoic acid, and teichoic acid are common structural components contributing to colonization. In addition, surface proteins such as staphylococcal fibronectin-binding protein and bone-sialoprotein binding proteins specifically bind host tissue components. Toxins are commonly produced among staphylococcal pathogens and are highly damaging; several human diseases, including food poisoning, toxic shock syndrome and exfoliative skin conditions, are the direct result of extracellular secreted toxin proteins. A single isolate may encode genes for 20-30 different secreted toxins. Some of the secreted protein products are superantigens that can bind nonspecifically to the MHC class II molecule of an antigen-presenting cell and, simultaneously, to the T-cell receptor of a T cell. The binding induces T cell signaling and leads to the release of high levels of proinflammatory factors, ultimately inducing host damage due to the overwhelming immune response. Another class of virulence factors expressed on the surface disguise the bacteria from the host immune system. For example, the *S. aureus* surface-expressed Protein A inhibits opsonization and phagocytosis by binding of the Fc component of host antibody. Numerous proteases, hemolysins (alpha, beta, gamma and delta), nucleases, lipases, hyaluronidase, and collagenase also aid bacteria in extracting nutrients from surrounding cells and protecting them against host defenses.

Antibiotic Resistance Among Staphylococci

The CDC estimates that each year nearly 2 million people in the United States acquire a nosocomial infection, resulting in 90,000 deaths annually. Of these fatal infections, 70% are caused by antibiotic-resistant bacteria. The increase in antibiotic-resistance among microbial species is particularly pronounced in skin and mucosal colonizers such as *S. aureus*. For example, the vast majority of *S. aureus* isolated from hospital settings are resistant to penicillin, and 50% are also resistant to the semisynthetic penicillins, such as methicillin, nafcillin, and oxacillin. These isolates, referred to as MRSA (methicillin resistant *S. aureus*) were first seen in the 1970s, and are now firmly established in hospital settings. Recently there have been several cases of MRSA infections in the community, where the infected individuals had no previous exposure to hospitals or healthcare workers. This alarming trend is intensified by the isolation of MRSA isolates that are less susceptible to vancomycin, a glycopeptide used to treat MRSA. Very few strains have been shown to be truly resistant to vancomycin according to the CDC's definition of vancomycin resistance, but several MRSA strains have been characterized as consisting of subpopulations with reduced susceptibility to vancomycin, or VISA (vancomycin intermediate *S. aureus*). Since the isolation of vancomycin resistant and vancomycin intermediate strains is a relatively new development, there is little data concerning their prevalence in hospitals and/or the community. Occasionally, VRSA (vancomycin resistant *S. aureus*) with full resistance to vancomycin and carrying a resistance plasmid likely acquired from *Enterococcus* spp. have also been recovered from humans.

Strategies for the Prevention and Treatment of *Staphylococcus* Infections

The emergence of numerous gram-positive pathogens that are resistant to multiple antibiotics has fueled research efforts aimed at developing preventative vaccines to protect against disease. Vaccines are designed to be administered to patients in order to elicit a long-term memory response from the immune system, so that if the pathogen is encountered at a future time, the immune system can more quickly and efficiently clear the pathogen. To date, a broadly-protective vaccine against gram-positive pathogens associated with a number of severe human diseases, particularly those disease associated with staphylococcal infections, is not available. Vaccine development approaches for the prevention of staphylococcal infections include those reporting the use of microbial surface components recognizing adhesion matrix molecules [MSCRAMMS (Nilsson et al. 1998. J Clin Invest 101:2640-9; Menzies et al. 2002. J Infect Dis 185:937-43; Fattom et al. 2004. Vaccine 22:880-7], surface polysaccharides (McKenney et al. 2000: McKenney et al. 1999. Science 284:1523-7; Maira-Litran et al. 2002. Infect Immun 70:4433-40; Maira-Litran et al. 2004. Vaccine 22:872-9; Maira-Litran et al. 2005. Infect Immun 73:6752-62) and mutated exoproteins (Lowell et al. 1996. Infect Immun 64:4686-93; Stiles et al. 2001. Infect Immun 69:2031-6; Gampfer et al. 2002. Vaccine 20:3675-84), as antigens in subunit vaccine compositions, as well as one live avirulent strain (Reinoso et al. 2002. Can J Vet Res 66:285-8) and several DNA vaccine approaches (Ohwada et al. 1999. J Antimicrob Chemother 44:767-74); Brouillette et al. 2002. Vaccine 20:2348-57; Senna et al. 2003. Vaccine 21:2661-6). Although many of these compositions have shown some degree of protection, they have achieved little cross-protection against diverse staphyloccocal strains and have additionally failed to elicit substantial immune responses in immunocompromised patients, an important at-risk population for nosocomial infections.

The most severe staphylococcal diseases are those mediated by the aforementioned supernantigenic pyrogenic exotoxins (SPEs) that nonspecifically stimulate T-cells independent of antigen presentation. Such diseases include toxic shock syndrome, exfoliative skin disease, and possibly Kawasaki syndrome. For these SPE-mediated diseases, immunotherapeutic agents that boost the immune system during an active infection are often more effective than vaccines, which are typically administered prior to infection. The overwhelming nature of the immune response to SPE necessitates rapid reduction in toxin activity as the first objective in therapy. To date, toxin neutralization in *S. aureus*-mediated disease has been most effectively accomplished by the administration of intravenous human immunoglobulin (IVIG), a purified, concentrated human antibody preparation from several thousand human donors (Takei et al. 1993. J Clin Invest 91:602-7; Stohl and Elliot. 1996. Clin Immunol Immunopathol 79:122-33). The widespread distribution of *S. aureus*, which colonizes approximately 30% of healthy human adults, coincides with high exposure rates for the majority of the population, so the level of anti-staphylococcal anti-toxin antibodies in IVIG is often sufficient to neutralize toxin long enough to stabilize the immune response until the bacterial load is reduced with antibiotics (Schlievert, 2001. J Allergy Clin Immunol 108(4 Suppl): S07-110). IVIG preparations from multiple manufacturers have been shown to neutralize toxin in proliferation assays with human peripheral blood mononuclear cells, inhibit toxin-induced human T cell-driven B cell differentiation in vitro (Stohl and Elliot. 1996. Clin Immunol Immunopathol 79:122-33; Stohl and Elliott. 1995. J Immunol 155:1838-50; Stohl et al. 1994. J Immunol 153:117-27) and reduce IL-4 and IL-2 secretion in PBMCs stimulated with staphylococcal enterotoxin B (Takei et al. 1993. J Clin Invest 91:602-7; Darenberg et al. 2004. Clin Infect Dis 38:836-42). IVIG therapy, with its proven ability to neutralize SPE, is now a recommended therapy for Kawasaki syndrome and is gaining favor as a treatment method for staphylococcal toxic shock syndrome (Schlievert 2001. J Allergy Clin Immunol 108(4 Suppl):S107-110). Use of IVIG as an immunoprotective wound lavage during surgery has also been investigated in mice (Poelstra et al. 2000. Tissue Eng 6(4):401-411). Although standard IVIG has utility for limiting the advance of some staphylococcal SPE-mediated disease, the safety, efficacy and consistency of human IVIG preparations generated from thousands of unselected human donors remains controversial (Baker et al. 1992. N Engl J Med 327:213-9; Miller et al. 2001. J Allergy Clin Immunol 108:S91-4; Sacher, 2001. J Allergy Clin Immunol 108:S139-46; Darenberg et al. 2004. Clin Infect Dis 38:836-42). Furthermore, the benefit of IVIG in preventing some staphylococcal infections is doubtful (Baker et al. 1992. N Engl J Med 327:213-9; Hill, H. R. 2000. J Pediatr 137:595-7; Darenberg et al. 2004. Clin Infect Dis 38:836-42). In order to increase the effectiveness of IVIG in treating staphylococcal infections in certain at-risk populations, a plasma-derived, donor-selected, polyclonal anti-staphylococcal human IgG with high titers of antibody directed toward the staphylococcal MSCRAMMS clumping factor A (ClfA) and fibrinogen-binding protein G (SdrG) was created and tested with success in very low birthweight infants to prevent staphylococcal sepsis (Vernachio et al. 2003. Antimicrob Agents Chemother 47:3400-6; Bloom et al. 2005. Pediatr Infect Dis J 24:858-866; Capparelli et al. 2005. Antimicrob Agents Chemother 49:4121-7). A specific humanized monoclonal antibody toward the S. aureus MSCRAMM Clumping factor A, is also being developed. The antibody was selected from a pool of thousands of murine anti-ClfA antibodies for its ability to bind ClfA in a manner that abrogates S. aureus binding to human fibronectin and was subsequently humanized by mutating specific targeted residues to mimic the homologous human germline subgroup antibody (Hall et al. 2003. Infect Immun 71:6864-70; Domanski et al. 2005. Infect Immun 73:5229-32). The specific antibody is being designed for use in conjunction with antibiotics for the treatment of severe life-threatening S. aureus infection, although animal studies also demonstrated a prophylactic protective effect.

SUMMARY

The present invention provides compositions including two or more isolated polypeptides. The two isolated polypeptides may have a molecular weight of 88 kDa, 55 kDa, 38 kDa, 37 kDa, 36 kDa, 35 kDa, 33 kDa, or a combination thereof. For instance, a composition may include isolated proteins of 88 kDa and 55 kDa. In some aspects the composition may include isolated polypeptides having molecular weights of 88 kDa, 55 kDa, 38 kDa, 37 kDa, 36 kDa, 35 kDa, and 33 kDa. The molecular weight is determined by electrophoresis on a sodium dodecyl sulfate-polyacrylamide gel. The polypeptides are isolatable from a Staphylococcus aureus when incubated in media including an iron chelator and not isolatable when grown in the media without the iron chelator. The composition protects an animal, such as a mouse or cow or human, against challenge with an S. aureus strain, for instance ATCC strain 19636. The composition may further include a pharmaceutically acceptable carrier, and may further include an isolated polypeptide having a molecular weight of 150 kDa, 132 kDa, 120 kDa, 75 kDa, 58 kDa, 50 kDa, 44 kDa, 43 kDa, 41 kDa, 40 kDa, or a combination thereof, and isolatable from a S. aureus when grown in the media without the iron chelator. In some aspects the polypeptides of the composition may be isolated from S. aureus ATCC strain 19636.

The present invention also provides methods for using the compositions. In one aspect the method is for treating in infection in a subject, and includes administering an effective amount of a composition of the present invention to a subject having or at risk of having an infection caused by a Staphylococcus spp. In another aspect, the method is for treating a symptom in a subject, and it includes administering an effective amount of a composition of the present invention to a subject having an infection caused by a Staphylococcus spp. The subject may be a mammal, such as a human, horse, or cow. The Staphylococcus spp. may be S. aureus.

The present invention further provides methods for using antibody, for instance, polyclonal antibody, that specifically binds polypeptides of the present invention. In one aspect, the method is for treating an infection in a subject, and includes administering an effective amount of a composition to a subject having or at risk of having an infection caused by a Staphylococcus spp., wherein the composition includes antibody that specifically binds two isolated polypeptides of the present invention. In another aspect, the method is for treating a symptom in a subject, and includes administering an effective amount of a composition to a subject having an infection caused by a Staphylococcus spp., wherein the composition includes antibody that specifically binds two isolated polypeptides of the present invention. The subject may be a mammal, such as a human, horse, or cow. The Staphylococcus spp. may be S. aureus.

Also provided by the present invention are methods for decreasing colonization in a subject. In one aspect, the method includes administering an effective amount of a composition of the present invention to a subject colonized by a Staphylococcus spp. In another aspect, the method includes administering an effective amount of a composition to a subject colonized by Staphylococcus spp., wherein the composition includes antibody that specifically binds two isolated polypeptides of the present invention.

The present invention provides a kit for detecting antibody that specifically binds a polypeptide. The kit includes, in separate containers, an isolated polypeptide of the present invention, and a reagent that detects an antibody that specifically binds the polypeptide.

The present invention further provides a composition including two isolated polypeptides having molecular weights selected from 88 kDa, 55 kDa, 38 kDa, 37 kDa, 36 kDa, 35 kDa, and 33 kDa, wherein molecular weight is determined by electrophoresis on a sodium dodecyl sulfate-polyacrylamide gel. Each polypeptide of the composition has a mass fingerprint of at least 80% similarity to a mass fingerprint of a polypeptide of the same molecular weight polypeptide expressed by Staphylococcus aureus ATCC strain 19636, wherein the polypeptide is isolatable from a Staphylococcus aureus when incubated in media comprising an iron chelator and not isolatable when grown in the media without the iron chelator. For instance, the isolated polypeptide with a molecular weight of 88 kDa has a mass fingerprint of at least 80% similarity to a mass fingerprint of a 88 kDa polypeptide expressed by Staphylococcus aureus ATCC strain 19636, and the isolated polypeptide with a molecular weight of 55 kDa has a mass fingerprint of at least 80% similarity to a mass fingerprint of a 55 kDa polypeptide expressed by Staphylococcus aureus ATCC strain 19636.

BRIEF DESCRIPTION OF THE FIGURES

FIG. 3. Kaplan-Meier survival curve showing percent survival after vaccination and homologous challenge with S. aureus ATCC 19636.

FIG. 4. Kaplan-Meier survival curve showing percent survival after vaccination and heterologous challenge with S. aureus ATCC 19636.

FIG. 5. The Kaplan-Meier survival curve showing percent survival after passive immunization and homologous challenge with *S. aureus* ATCC 19636.

FIG. 6. The Kaplan-Meier survival curve showing percent survival after passive immunization and heterologous challenge with *S. aureus* strain 1477.

DETAILED DESCRIPTION OF PREFERRED EMBODIMENTS OF THE INVENTION

Figure 1:
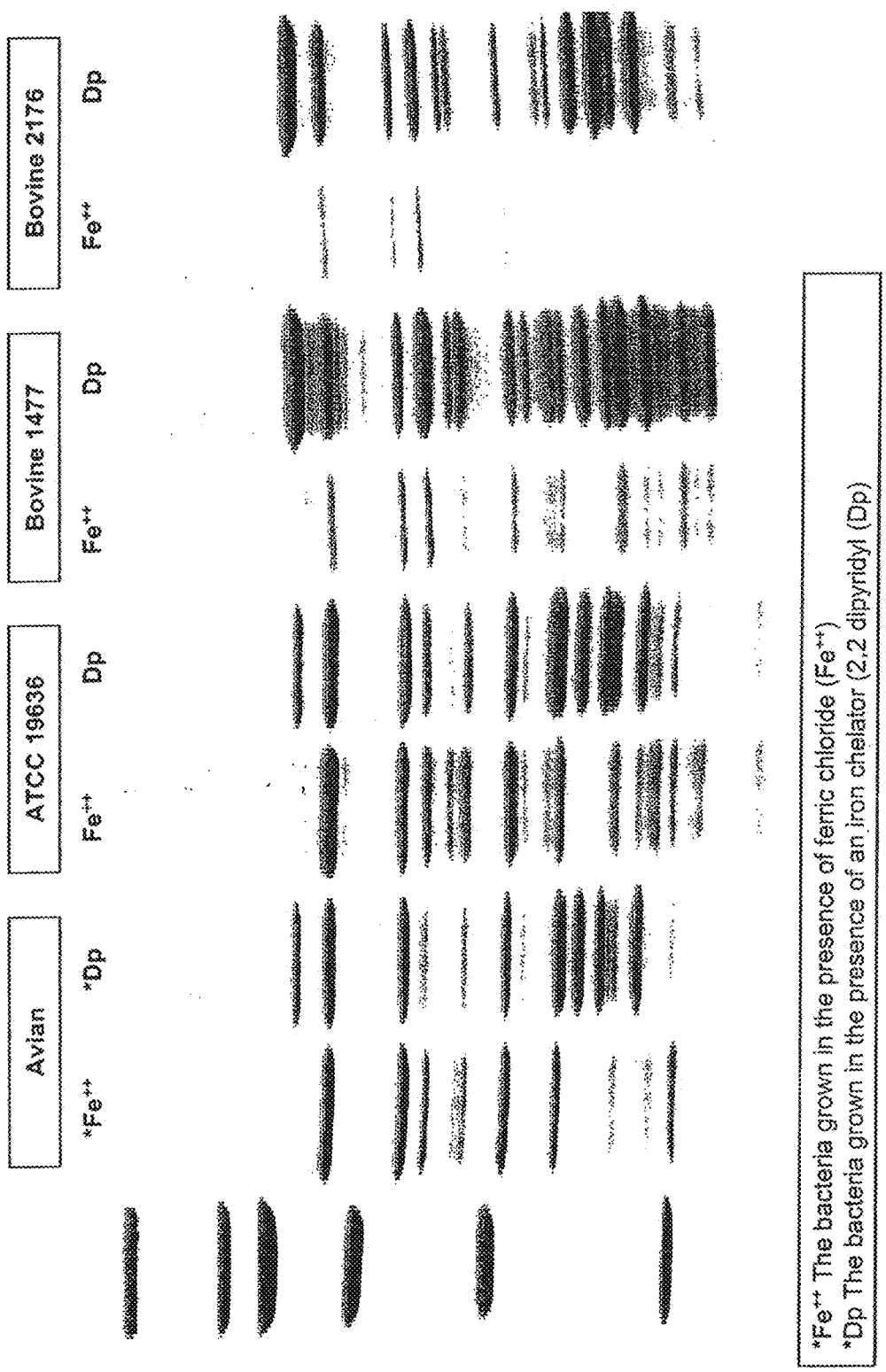
FIG. 1. The electrophoretic profile of the proteins of different strains Staphylococcus aureus derived from different species grown with and without iron (lanes marked Fe++ and DP, respectively).

The present invention provides polypeptides and compositions including polypeptides. As used herein, "polypeptide" refers to a polymer of amino acids linked by peptide bonds. Thus, for example, the terms peptide, oligopeptide, protein, and enzyme are included within the definition of polypeptide. This term also includes post-expression modifications of the polypeptide, such as glycosylations, acetylations, phosphorylations, and the like. The term polypeptide does not connote a specific length of a polymer of amino acids. A polypeptide may be isolatable directly from a natural source, or can be prepared with the aid of recombinant, enzymatic, or chemical techniques. In the case of a polypeptide that is naturally occurring, such a polypeptide is typically isolated. An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present. An "isolatable" polypeptide is a polypeptide that could be isolated from a particular source. A "purified" polypeptide is one that is at least 60% free, preferably at least 75% free, and most preferably at least 90% free from other components with which they are naturally associated. Polypeptides that are produced outside the organism in which they naturally occur, e.g., through chemical or recombinant means, are considered to be isolated and purified by definition, since they were never present in a natural environment. As used herein, a "polypeptide fragment" refers to a portion of a polypeptide that results from digestion of a polypeptide with a protease. Unless otherwise specified, "a," "an," "the," and "at least one" are used interchangeably and mean one or more than one. The terms "comprises" and variations thereof do not have a limiting meaning where these terms appear in the description and claims.

A polypeptide of the present invention may be characterized by molecular weight, mass fingerprint, or the combination thereof. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, and liquid chromatography including HPLC. Preferably, molecular weight is determined by resolving a polypeptide using an SDS polyacrylamide gel having a stacking gel of about 4% and a resolving gel of about 10% under reducing and denaturing conditions. Unless indicated otherwise, molecular weight refers to molecular weight as determined by SDS-PAGE. As used herein, a "mass fingerprint" refers to a population of polypeptide fragments obtained from a polypeptide after digestion with a protease. Typically, the polypeptide fragments resulting from a digestion are analyzed using a mass spectrometric method. Each polypeptide fragment is characterized by a mass, or by a mass (m) to charge (z) ratio, which is referred to as an "m/z ratio" or an "m/z value". Methods for generating a mass fingerprint of a polypeptide are routine. An example of such a method is disclosed in Example 13.

Polypeptides of the present invention may be metal regulated polypeptides. As used herein, a "metal regulated polypeptide" is a polypeptide that is expressed by a microbe at a greater level when the microbe is grown in low metal conditions compared to growth of the same microbe in high metal conditions. Low metal and high metal conditions are described herein. For instance, one class of metal regulated polypeptide produced by *Staphylococcus* spp. is not expressed at detectable levels during growth of the microbe in high metal conditions but is expressed at detectable levels during growth in low metal conditions. Examples of such metal regulated polypeptides isolatable from *S. aureus* after growth in low iron conditions have molecular weights of 88 kDa, 55 kDa, 38 kDa, 37 kDa, 36 kDa, 35 kDa, and 33 kDa. Examples of such metal regulated polypeptides isolatable from *S. aureus* after growth in low zinc or low copper conditions have molecular weights of 115 kDa, 88 kDa, 80 kDa, 71 kDa, 69 kDa, 35 kDa, 30 kDa, 29, kDa, and 27 kDa.

The present invention also includes polypeptides that are not metal regulated. Such polypeptides are expressed in the presence of a metal ion such as ferric chloride, and also expressed when grown in low iron conditions. Examples of such polypepides isolatable from *S. aureus* have molecular weights of 150 kDa, 132 kDa, 120 kDa, 75 kDa, 58 kDa, 50 kDa, 44 kDa, 43 kDa, 41 kDa, and 40 kDa.

Whether a polypeptide is a metal regulated polypeptide or not can be determined by methods useful for comparing the presence of polypeptides, including, for example, gel filtration, gel electrophoresis including sodium dodecyl sulfate-polyacrylamide gel electrophoresis (SDS-PAGE), capillary electrophoresis, mass spectrometry, and liquid chromatography including HPLC. Separate cultures of a microbe are grown under high metal conditions and under low metal conditions, polypeptides of the present invention are isolated as described herein, and the polypeptides present in each culture are resolved and compared. Typically, an equal amount of polypeptides from each culture is used. Preferably, the polypeptides are resolved using an SDS polyacrylamide gel having a stacking gel of about 4% and a resolving gel of about 10% under reducing and denaturing conditions. For instance, 30 micrograms (μg) of total polypeptide from each culture may be used and loaded into wells of a gel. After running the gel and staining the polypeptides with Coomasic Brilliant Blue, the two lanes can be compared. When determining whether a polypeptide is or is not expressed at a detectable level, 30 μg of total polypeptide from a culture is resolved on an SDS-PAGE gel and stained with Coomasie Brilliant Blue using methods known in the art. A polypeptide that can be visualized by eye is considered to be expressed at a detectable level, while a polypeptide that cannot be visualized by eye is considered to not be expressed at a detectable level.

Polypeptides of the present invention may have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced.

The immunogenic activity may be protective. "Protective immunogenic activity" refers to the ability of a polypeptide to elicit an immunological response in an animal that prevents or inhibits infection by Staphylococcus spp., for instance, S. aureus. Whether a polypeptide has protective immunogenic activity can be determined by methods known in the art, for instance as described in Examples 5, 9, or 12. For example, a polypeptide of the present invention, or combination of polypeptides of the present invention, protect a rodent such as a mouse against challenge with a Staphylococcus spp. A polypeptide of the present invention may have seroactive activity. "Seroactive activity" refers to the ability of a candidate polypeptide to react with antibody present in convalescent serum from an animal infected with a Staphylococcus spp., for instance, S. aureus. In some aspects, the convalescent serum may be from an animal infected with the ATCC isolate 19636, strain SAAV1, strain 2176, or strain 1477. Polypeptides of the present invention may have immunoregulatory activity. "Immunoregulatory activity" refers to the ability of a polypeptide to act in a nonspecific manner to enhance an immune response to a particular antigen. Methods for determining whether a polypeptide has immunoregulatory activity are known in the art.

A polypeptide of the present invention may have the characteristics of a polypeptide expressed by a reference microbe. The characteristics can include both molecular weight and mass fingerprint. The reference microbe can be a gram positive, preferably a member of the family Micrococcaceae, preferably, Staphylococcus spp., more preferably, Staphylococcus aureus. Preferred examples of strain are detailed in Table 1.

TABLE 1

Bacterial strains.

| Bacterial cell | Laboratory designation |
| --- | --- |
| S. aureus | ATCC isolate 19636 |
| S. aureus | strain SAAV1 |
| S. aureus | strain 1477 |
| S. aureus | strain 2176 |

When the reference microbe is S. aureus ATCC isolate 19636, a candidate polypeptide is considered to be a polypeptide of the present invention if it has a molecular weight of 88 kDa, 55 kDa, 38 kDa, 37 kDa, 36 kDa 35 kDa, or 33 kDa, and has a mass fingerprint that is similar to the mass fingerprint of a metal regulated polypeptide expressed by a reference microbe and having a molecular weight of 88 kDa, 55 kDa, 38 kDa, 37 kDa, 36 kDa 35 kDa, or 33 kDa, respectively. Preferably, such polypeptides are metal regulated. For instance, a candidate polypeptide is a polypeptide of the present invention if it has a molecular weight of 88 kDa and has a mass fingerprint similar to the mass fingerprint of an 88 kDa metal regulated polypeptide produced by the reference strain S. aureus ATCC isolate 19636.

When the reference microbe is S. aureus isolate SAAV1, a candidate polypeptide is considered to be a polypeptide of the present invention if it has a molecular weight (as determined by SDS-PAGE) of 88 kDa, 55 kDa, 38 kDa, 37 kDa, 36 kDa, 35 kDa, or 33 kDa, and has a mass fingerprint that is similar to the mass fingerprint of a polypeptide expressed by a reference microbe and having a molecular weight (as determined by SDS-PAGE) of 88 kDa, 55 kDa, 38 kDa, 37 kDa, 36 kDa, 35 kDa, or 33 kDa, respectively. Preferably, such polypeptides are metal regulated. For instance, a candidate polypeptide is a polypeptide of the present invention if it has a molecular weight of 88 kDa and has a mass fingerprint similar to the mass fingerprint of an 88 kDa metal regulated polypeptide produced by the reference strain S. aureus isolate SAAV1.

When the reference microbe is S. aureus strain 2176, a candidate polypeptide is considered to be a polypeptide of the present invention if it has a molecular weight (as determined by SDS-PAGE) of 88 kDa, 80 kDa, 65 kDa, 55 kDa, 37 kDa, 36 kDa, 35 kDa, 33 kDa, or 32 kDa, and has a mass fingerprint that is similar to the mass fingerprint of a polypeptide expressed by a reference microbe and having a molecular weight (as determined by SDS-PAGE) of 88 kDa, 80 kDa, 65 kDa, 55 kDa, 37 kDa, 36 kDa, 35 kDa, 33 kDa, or 32 kDa, respectively. Preferably, such polypeptides are metal regulated. For instance, a candidate polypeptide is a polypeptide of the present invention if it has a molecular weight of 88 kDa and has a mass fingerprint similar to the mass fingerprint of an 88 kDa metal regulated polypeptide produced by the reference strain S. aureus isolate 2176.

When the reference microbe is S. aureus strain 1477, a candidate polypeptide is considered to be a polypeptide of the present invention if it has a molecular weight (as determined by SDS-PAGE) of 88 kDa, 80 kDa, 65 kDa, 55 kDa, 37 kDa, 36 kDa, 35 kDa, 33 kDa, or 32 kDa, and has a mass fingerprint that is similar to the mass fingerprint of a polypeptide expressed by a reference microbe and having a molecular weight (as determined by SDS-PAGE) of 88 kDa, 80 kDa, 65 kDa, 55 kDa, 37 kDa, 36 kDa, 35 kDa, 33 kDa, or 32 kDa, respectively. Preferably, such polypeptides are metal regulated. For instance, a candidate polypeptide is a polypeptide of the present invention if it has a molecular weight of 88 kDa and has a mass fingerprint similar to the mass fingerprint of an 88 kDa metal regulated polypeptide produced by the reference strain S. aureus isolate 1477.

The polypeptides expressed by a reference microbe and referred to above by molecular weight can be obtained by growth of the reference microbe under low metal conditions and the subsequent isolation of a polypeptide by the processes disclosed herein. A candidate polypeptide is isolatable from a microbe, preferably a gram positive microbe, more preferably, a member of the family Micrococcaceae, preferably, Staphylococcus spp., more preferably, Staphylococcus aureus.

Other gram positive microbes from which polypeptides can be isolated include Corynebacterium spp., Enterococcus spp., Erysipelothrix spp., Kytococcus spp., and Micrococcus spp., Mycobacterium spp., and Erysipelothrix spp. A candidate polypeptide may also be produced using recombinant, enzymatic, or chemical techniques.

A candidate polypeptide may be evaluated by mass spectrometric analysis to determine whether the candidate polypeptide has a mass fingerprint similar to one of the polypeptides expressed by a reference microbe and referred to above by molecular weight. Typically, the candidate polypeptide is isolated, for instance by resolving the candidate polypeptide by gel electrophoresis and excising the portion of the gel containing the candidate polypeptide. Any gel electrophoresis method that separates polypeptides based on differing characteristics can be used, including 1 dimensional or 2 dimensional gel electrophoresis, as well as liquid chromatographic separation based on, for instance, hydrophobicity, pI, or size. The candidate polypeptide is fragmented, for instance by digestion with a protease. Preferably, the protease cleaves the peptide bond on the carboxy-terminal side of the amino acid lysine and the amino acid arginine, except when the amino acid following the lysine or the arginine is a proline. An example of such a protease is trypsin. Methods for digesting a polypeptide with trypsin are routine and known in the art. An example of such a method is disclosed in Example 13.

Methods for the mass spectrometric analysis of polypeptides are routine and known in the art and include, but are not limited to, matrix assisted laser desorption/ionization time of flight mass spectroscopy (MALDI-TOF MS). Typically, a mixture containing the polypeptide fragments obtained from a candidate polypeptide is mixed with a matrix that functions to transform the laser energy to the sample and produce ionized, preferably monoisotopic, polypeptide fragments. Examples of matrices that can be used include, for instance, sinapinic acid or cyano-4-hydroxycinnamic acid. An example of a method for the analysis of polypeptides by MALDI-TOF MS is described in Example 13. The ionized polypeptide fragments are separated according to their m/z ratio, and detected to yield a spectrum of m/z ratio versus intensity. The spectrum includes m/z values that represent the polypeptide fragments derived from the candidate polypeptide. For any given polypeptide, the amount of each polypeptide fragment resulting from a trypsin digestion should be equimolar. However, it is known that trypsin digestion is not always 100% efficient, for instance, some sites are more efficiently cleaved. Thus, when MALDI-TOF MS is used to determine m/z values, the intensity of each m/z value is typically not identical. Generally, a spectrum has a background level of noise present across most of the x-axis (i.e., the axis having the values of the m/z ratios). This background level of noise varies depending on the running conditions and the machine used, and is easily identified by visual inspection of the spectrum. An m/z value is generally considered to represent a polypeptide fragment when the intensity is at least 2 times greater, at least 3 times greater, or at least 4 times greater than the background level of noise. The spectrum usually includes other m/z values that are artifacts resulting from, for instance, incomplete digestion, over digestion, other polypeptides that may be present in the mixture, or the protease used to digest the polypeptide including m/z values resulting from autolysis of the protease. This method of digesting a polypeptide with a protease is recognized in the art as resulting in a mass fingerprint of great specificity that can be used to accurately characterize the polypeptide and distinguish it from other polypeptides.

In this aspect of the invention, when a candidate polypeptide is analyzed by mass spectroscopy, preferably both the candidate polypeptide and the polypeptide from the reference microbe are prepared and analyzed together, thereby decreasing any potential artifacts resulting from differences in sample handling and running conditions. Preferably, all reagents used to prepare and analyze the two polypeptides are the same. For instance, the polypeptide from the reference microbe and the candidate polypeptide are isolated under substantially the same conditions, fragmented under substantially the same conditions, and analyzed by MALDI-TOF MS on the same machine under substantially the same conditions. A mass fingerprint of a candidate polypeptide is considered to be similar to the mass fingerprint of a polypeptide from a reference microbe when at least 80%, at least 90%, at least 95%, or substantially all of the m/z values present in the spectrum of the reference microbe polypeptide and above the background level of noise are also present in the spectrum of the candidate polypeptide.

In another aspect, a polypeptide is considered to be a polypeptide of the present invention if it has a molecular weight of a reference polypeptide described in Table 2, 3, 4, or 5 and has a mass fingerprint that includes the population of polypeptide fragments of the reference polypeptide as listed in Table 2, 3, 4, or 5. For instance, a polypeptide of the present invention includes a polypeptide of 88 kDa and a mass fingerprint that includes polypeptide fragments having masses of HVDVR, YSYER, IIGDYRR, IFTDYRK, ELKELGQK, YAQVKPIR, QMQFFGAR, SMQPFGGIR, VSGYAVNFIK, NHATAWQGFK, LWEQVMQLSK, SLGKEPEDQNR, DGISNTFSIVPK, AGVITGLPDAYGR, TSTFLDIYAER, SMQPFGGIRMAK, THNQGVFDAYSR, KAGVITGLPDAYGR. TLLYAINGGKDEK, IEMALHDTEIVR, AGEPFAPGANPMHGR, VALYGVDFLMEEK, KTHNQGVFDAYSR, YGFDLSRPAENFK, TSSIQYENDDIMR, KAGEPFAPGANPMHGR, RVALYGVDFLMEEK, LWEQVMQLSKEER, MLETNKNH ATA WQGFK, MHDFNTMSTEMSEDVIR, YGNNDDRVDDIAVDLVER, ETLIDAMEHPEEYPQLTIR, YAQVKPIRNEEGLVVDFEIEGDFPK. The mass fingerprint of a candidate polypeptide can be determined by a mass spectrometric method, for instance by MALDI-TOF MS. The mass fingerprint of a candidate polypeptide will generally have additional polypeptide fragments and therefore additional m/z values other than those listed for a polypeptide in Table 2, 3, 4, or 5. Preferably, when the candidate polypeptide is being compared to a polypeptide in Table 2, 3, 4, or 5, the candidate polypeptide is isolatable from a microbe, preferably a gram positive microbe, more preferably, a member of the family Micrococcaceae, preferably, *Staphylococcus* spp., more preferably, *Staphylococcus aureus*. Other gram positive microbes include *Corynebacterium* spp., *Enterococcus* spp., *Erysipelothrix* spp., *Kytococcus* spp., *Listeria* spp., *Micrococcus* spp., and *Mycobacterium* spp., and *Erysipelothrix* spp. A candidate polypeptide can be obtained by growth of a microbe under low metal conditions and the subsequent isolation of a polypeptide by the processes described herein.

It is well known in the art that modifications of amino acids can be accidentally introduced during sample handling, such as oxidation, and formation of carbamidomethyl derivatives. Further, these types of modifications alter the m/z value of a polypeptide fragment. For instance, if a polypeptide fragment contains a methionine that is oxidized, the m/z value will be increased by 16 relative to the same fragment that does not contain the oxidized methionine. Accordingly, those polypeptide fragments in Tables 2, 3, 4, or 5 having the notation "oxidation (M)" have an m/z value that is increased by 16 relative to the same fragment that does not contain the oxidized methionine. It is understood that the polypeptide fragments of Table 2, 3, 4, or 5 can be modified during sample handling.

TABLE 2

Characteristics of polypeptides obtained from *S. aureus* ATCC isolate 19636.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| P23 | 88 | 625.4 | HVDVR |
| | | 717.3 | YSYER |
| | | 892.5 | IIGDYRR |
| | | 942.5 | IFTDYRK |
| | | 944.5 | ELKELGQK |
| | | 974.6 | YAQVKPIR |
| | | 984.5 | QMQFFGAR |
| | | 992.5 | SMQPFGGIR |
| | | 1097.6 | VSGYAVNFIK |
| | | 1159.5 | NHATAWQGFK |
| | | 1261.7 | LWEQVMQLSK |
| | | 1272.7 | SLGKEPEDQNR |
| | | 1277.7 | DGISNTFSIVPK |
| | | 1289.7 | AGVITGLPDAYGR |
| | | 1315.7 | TSTFLDIYAER |
| | | 1322.7 | SMQPFGGIRMAK |
| | | 1394.7 | THNQGVFDAYSR |
| | | 1417.8 | KAGVITGLPDAYGR |
| | | 1421.8 | TLLYAINGGKDEK |
| | | 1426.8 | IEMALHDTEIVR |
| | | 1508.8 | AGEPFAPGANPMHGR |
| | | 1513.9 | VALYGVDFLMEEK |
| | | 1522.8 | KTHNQGVFDAYSR |
| | | 1543.9 | YGFDLSRPAENFK |
| | | 1571.8 | TSSIQYENDDIMR |
| | | 1636.9 | KAGEPFAPGANPMHGR |
| | | 1670.0 | RVALYGVDFLMEEK |
| | | 1676.0 | LWEQVMQLSKEER |
| | | 1876.2 | MLETKNHATAWQGFK |
| | | 2043.1 | MHDFNTMSTEMSEDVIR |
| | | 2078.2 | YGNNDDRVDDIAVDLVER |
| | | 2285.5 | ETLIDAMEHPEEYPQLTIR |
| | | 2892.9 | YAQVKPIRNEEGLVVDFEIEGDFPK |
| P25 | 55 | 783.6 | LHSWLK |
| | | 911.7 | KLHSWLK |
| | | 937.6 | TYTFHLR |

TABLE 2-continued

Characteristics of polypeptides obtained from *S. aureus* ATCC isolate 19636.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 996.6 | KFDGTGPFK |
| | | 1025.6 | QAIGHMVNR |
| | | 1063.6 | KWDVSEDGK |
| | | 1185.6 | IYNSIDDAFK |
| | | 1277.6 | NLEMAMYYDK |
| | | 1324.7 | ENKQLTYTTVK |
| | | 1346.7 | AESLLDEAGWKK |
| | | 1381.8 | TVRQAIGHMVNR |
| | | 1394.8 | TYTFHLRDDVK |
| | | 1400.7 | KGETNFAFTDDR |
| | | 1419.7 | FHDGTPFDADAVK |
| | | 1422.8 | NVTDINFDMPTR |
| | | 1428.8 | DKIYNSIDDAFK |
| | | 1483.8 | EQAEYLQAEFKK |
| | | 1509.8 | VMPAGETAFLSMKK |
| | | 1547.9 | FHDGTPFDADAVKK |
| | | 1550.9 | NVTDIHFDMPTRK |
| | | 1559.9 | LNINGETSDKIAER |
| | | 1788.1 | EILDGQEKPATQLFAK |
| | | 1930.1 | GSSSQKEQAEYLQAEFK |
| | | 1946.0 | DESADFNKNDQYWGEK |
| | | 2100.4 | IAKEILDGQEKPATQLFAK |
| | | 2239.3 | VSFTQSQYELPFNEMQYK |
| | | 2493.5 | EAYQPALAELAMPRPYVFVSPK + Oxidation (M) |
| | | 2900.6 | DIGDMNPHVYGCSMSAESMIYEPLVR + 2 Oxidation (M) |
| | | 2916.6 | DIGDMNPHVYGGSMSAHSMIYEPLVR + 3 Oxidation (M) |
| P26 | 38 | 993.6 | IVYVGADEK |
| | | 996.7 | QALNNPVLK |
| | | 1237.7 | ETVKIENNYK |
| | | 1272.7 | ENPDVILAMDR |
| | | 1502.0 | IAATKPEVIFISGR |
| | | 1507.9 | NAVVLDYGALDVMK |
| | | 1523.9 | ALPNFLESFKDDK |
| | | 1559.9 | LWYFAAGSTTTTIK |
| | | 1716.0 | FGGLVYDTLGFNAVDK |

TABLE 2-continued

Characteristics of polypeptides obtained from *S. aureus* ATCC isolate 19636.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1737.0 | IVYVGADEKNLIGSMK |
| | | 1844.1 | FGGLVYDTLGFNAVDKK |
| | | 1929.1 | GRFGGLVYDTLGFNAVDK |
| | | 1998.2 | TVMYLLVNEGELSTFGPK |
| | | 2234.4 | EVNFDKIAATKPEVIFISGR |
| | | 3143.8 | VSNSNHGQNVSNEYVNKENPDVILAMDR |
| P27 | 37 | 699.5 | FEYIK |
| | | 729.4 | DAWPLK |
| | | 792.5 | ASVVNFR |
| | | 852.4 | VYDQLSK |
| | | 987.5 | HAMGTTEIK |
| | | 1008.5 | LIDDLYEK |
| | | 1020.5 | YKDAWPLK |
| | | 1074.5 | EKEAEDLLK |
| | | 1083.6 | LKPDLIVASK |
| | | 1169.5 | FEYIKNDLK |
| | | 1182.5 | KTESEWTSSK |
| | | 1184.5 | YDDKVAAFQK |
| | | 1223.5 | NEKVYDQLSK |
| | | 1278.6 | IAPTVSTDTVFK |
| | | 1497.6 | TESEWTSSKEWK |
| | | 1502.7 | DAWPLKASVVNFR |
| | | 1558.8 | QVDNGKDIIQLTSK |
| | | 1605.8 | LIDDLYEKLNIEK |
| | | 1623.8 | IVGQEPAPNLEEISK |
| | | 1712.8 | ESIPLMNADHIFVVK |
| | | 1800.9 | IYAGGYAGEILNDLGFK |
| | | 1957.0 | IYAGGYAGEILNDLGFKR |
| | | 2252.0 | NNQVSDDLDEITWNLAGGYK |
| | | 3383.9 | RVVTLYQGATDVAVSLGVKPVGAVESWTQKPK |
| P28 | 36 | 646.4 | DVWAR |
| | | 725.5 | IIKPVR |
| | | 1068.4 | IGDYTSVGTR |
| | | 1185.5 | KQPNLEEISK |
| | | 1327.6 | LKPDLIIADSSR |
| | | 1343.6 | VDIVRDVWAR |

TABLE 2-continued

Characteristics of polypeptides obtained from S. aureus ATCC isolate 19636.

| Polypeptide designation | Approximate molecular weight in kilodaltons (kDa)[1] | m/z value of polypeptide fragments resulting from trypsin digest[2] | Predicted amino acid sequence of the polypeptide fragment |
| --- | --- | --- | --- |
| | | 2080.9 | GPYLQLDTEHLADLNPER |
| | | 2438.1 | AGLLAHPNYSYVGQFLNELGFK |
| | | 2789.4 | IVVLEYSFADALAALDVKPVGIADDGK |
| P29 | 35 | 760.5 | AGWAEVK |
| | | 1012.6 | TVDIPKDPK |
| | | 1107.6 | KDWEETTAK |
| | | 1204.7 | VAPTVVVDYNK |
| | | 1238.6 | YLEQQEMLGK |
| | | 1244.6 | LYTYGDNWGR |
| | | 1259.7 | IAVVAPTYAGGLK |
| | | 1281.7 | GGEVLYQAFGLK |
| | | 1516.8 | AGWAEVKQEEIEK |
| | | 1683.9 | LGANIVAVNQQVDQSK |
| | | 1877.1 | EKPDLIIVYSTDKDIK |
| | | 1884.0 | AIGQDATVSLFDEFDKK |
| | | 2227.1 | VDAGTYWYNDPYTLDFMR |
| | | 2781.4 | YAGDYIVSTSEGKPTPGYESTNMWK |
| P30 | 33 | 834.5 | QAIEFVK |
| | | 864.5 | YIAQLEK |
| | | 946.5 | QGTPEQMR |
| | | 962.5 | QAIEFVKK |
| | | 976.5 | DKFNDIPK |
| | | 1054.5 | AMITSEGAFK |
| | | 1202.5 | SNIETVHGSMK |
| | | 1268.6 | HLLVETSVDKK |
| | | 1443.6 | DIFGEVYTDSIGK |
| | | 1450.7 | TIQQTFIDNDKK |
| | | 1454.7 | VVTTNSILYDMAK |
| | | 1571.7 | KDIFGEVYTDSIGK |
| | | 1593.7 | QDPHAWLSLDNGIK |
| | | 1818.9 | DVKPIYLNGEEGNKDK |
| | | 1836.9 | DKQDPHAWLSLDNGIK |
| | | 1911.9 | QYGITPGYIWEINTEK |

TABLE 2-continued

Characteristics of polypeptides obtained from *S. aureus* ATCC isolate 19636.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 2582.3 | LTDADVILYNGLNLETGNGWFEK |
| | | 2710.2 | KLTDADVILYNGLNLETGNGWFEK |
| | | 2942.4 | NVGGDNVDIHSIVPVGQDPHEYEVKPK |

[1]Molecular weight as determined by SDS-PAGE.
[2]The m/z value of a polypeptide fragment can be converted to mass by subtracting 1 from the m/z value. Each mass includes a range of plus or minus 300 parts per million (ppm), or plus or minus 1 Da.

TABLE 3

Characteristics of polypeptides obtained from *S. aureus* isolate SAAV1.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| P33A | 55 | 783.4 | LHSWLK |
| | | 911.5 | KLHSWLK |
| | | 937.5 | TYTFHLR |
| | | 956.5 | KFDGTGPFK |
| | | 1025.5 | QAIGHMVNR |
| | | 1039.4 | NDQYWGEK |
| | | 1178.5 | GTDSLDKDSLK |
| | | 1185.5 | IYNSIDDAFK |
| | | 1222.6 | DKYTVELNLK |
| | | 1229.5 | ISTLIDNVKVK |
| | | 1346.6 | AESLLDEAGWKK |
| | | 1355.5 | EQAEYLQAEFK |
| | | 1381.6 | VMPAGETAFLSMK |
| | | 1400.5 | KGETNFAFTDDR |
| | | 1419.6 | FHDGTPFDADAVK |
| | | 1422.6 | NVTDINFDMPTR |
| | | 1483.6 | EQAEYLQAEFKK |
| | | 1547.7 | FHDGTPFDADAVKK |
| | | 1550.6 | NVTDINFDMPTRK |
| | | 1559.7 | LNINGETSDKIAER |
| | | 1787.9 | EILDGQEKPATQLFAK |
| | | 1945.8 | DESADFNKNDQYWGEK |
| | | 2239.0 | VSFTQSQYELPFNEMQYK |

TABLE 3-continued

Characteristics of polypeptides obtained from *S. aureus* isolate SAAV1.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 2354.1 | QIDDEGIFIPISHGSMTVVAPK |
| | | 2868.1 | DIGDMNPHVYGGSMSAESMIYEPLVR |
| P33B | 55 | 895.4 | FPYAANGR |
| | | 904.5 | ALLHASHR |
| | | 1045.5 | EEGLAIKASK |
| | | 1384.5 | GEAYFVDNNSLR |
| | | 1435.7 | TIEADYVLVTVGR |
| | | 1669.8 | RPNTDELGLEELGVK |
| | | 1841.0 | NAIIATGSRPIEIPNFK |
| | | 2179.2 | TSISNIYAIGDIVPGLPLAHK |
| | | 2546.2 | FVEAQHSENLGVIAESVSLNFQK |
| | | 2587.3 | VVGDFPIETDTIVIGAGPGGYVAAIR |
| P35 | 37 | 699.4 | FEYIK |
| | | 729.4 | DAWPLK |
| | | 792.4 | ASVVNFR |
| | | 852.4 | VYDQLSK |
| | | 1008.4 | LIDDLYEK |
| | | 1020.4 | YKDAWPLK |
| | | 1074.4 | EKEAEDLLK |
| | | 1083.5 | LKPDLIVASK |
| | | 1169.5 | FEYIKNDLK |
| | | 1182.4 | KTESEWTSSK |
| | | 1184.4 | YDDKVAAFQK |
| | | 1278.5 | IAPTVSTDTVFK |
| | | 1558.7 | QVDNGKDIIQLTSK |
| | | 1623.7 | IVGQEPAPNLEEISK |
| | | 1712.7 | ESIPLMNADHIFVVK |
| | | 1800.7 | IYAGGYAGEILNDLGFK |
| | | 1956.8 | IYAGGYAGEILNDLGFKR |
| | | 2251.9 | NNQVSDDLDEITWNLAGGYK |
| | | 3227.5 | VVTLYQGATDVAVSLGVKPVGAVESWTQKPK |
| P38 | 33 | 864.5 | YIAQLEK |
| | | 946.4 | QGTPEQMR |
| | | 976.5 | DKFNDIPK |
| | | 1054.5 | AMITSEGAFK |

TABLE 3-continued

Characteristics of polypeptides obtained from S. aureus isolate SAAV1.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1146.5 | FNDIPKEQR |
| | | 1268.6 | HLLVETSVDKK |
| | | 1322.5 | TIQQTFIDNDK |
| | | 1443.6 | DIFGEVYTDSIGK |
| | | 1450.6 | TIQQTFIDNDKK |
| | | 1454.6 | VVTTNSILYDMAK |
| | | 1593.7 | QDPHAWLSLDNGIK |
| | | 1818.9 | DVKPIYLNGEEGNKDK |
| | | 1836.8 | DKQDPHAWLSLDNGIK |
| | | 1911.9 | QYGITPGYIWEINTEK |
| | | 2942.4 | NVGGDNVDIHSIVPVGQDPHEYEVKPK |

[1]Molecular weight as determined by SDS-PAGE.
[2]The m/z value of a polypeptide fragment can be converted to mass by substracting 1 from the m/z value. Each mass includes a range of plus or minus 300 parts per million (ppm) or plus or minus 1 Da.

TABLE 4

Characteristics of polypeptides obtained from S. aureus isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| P478 | 88 | 736.35 | IIGDYR |
| | | 814.49 | IFTDYR |
| | | 942.42 | IFTDYRK |
| | | 945.36 | TGNTPDGRK |
| | | 974.40 | YAQVKPIR |
| | | 984.27 | QMQFFGAR |
| | | 992.41 | SMQPFGGIR |
| | | 1087.31 | EQQLDVISR |
| | | 1097.31 | VSGYAVNFIK |
| | | 1159.37 | NHATAWQGFK |
| | | 1261.37 | LWEQVMQLSK |
| | | 1289.46 | AGVITGLPDAYGR |
| | | 1315.42 | TSTFLDIYAER |
| | | 1322.39 | LREELSEQYR |
| | | 1394.37 | THNQGVFDAYSR |
| | | 1417.52 | KAGVITGLPDAYGR |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1426.36 | IEMALHDTEIVR |
| | | 1487.39 | NHATAWQGFKNGR |
| | | 1508.42 | AGEPFAPGANPMHGR |
| | | 1513.52 | VALYGVDFLMEEK |
| | | 1543.43 | YGFDLSRPAENFK |
| | | 1571.50 | TSSIQYENDDIMR |
| | | 1636.56 | KAGEPFAPGANPMHGR |
| | | 1859.80 | DLETIVGVQTEKPFKR |
| | | 1876.77 | TMATGIAGLSVAADSLSAIK |
| | | 2042.57 | MHDFNTMSTEMSEDVIR |
| | | 2077.68 | YGNNDDRVDDIAVDLVER |
| | | 2158.88 | AGVITESEVQEIIDHFIMK |
| | | 2284.90 | ETLIDAMEHPEEYPQLTIR |
| | | 2575.08 | FLHSLDNLGPAPEPNLTVLWSVR |
| | | 2628.01 | SGAQVGPNFEGINSEVLEYDEVFK |
| | | 2756.06 | SGAQVGPNFEGINSEVLEYDEVFKK |
| | | 3262.33 | VASTITSHDAGYLDKDLETIVGVQTEKPFK |
| P479 | 80 | 625.27 | HVDVR |
| | | 736.26 | IIGDYR |
| | | 814.22 | IFTDYR |
| | | 942.27 | IFTDYRK |
| | | 974.26 | YAQVKPIR |
| | | 984.18 | QMQFFGAR |
| | | 992.23 | SMQPFGGIR |
| | | 1087.16 | EQQLDVISR |
| | | 1097.24 | VSGYAVNFIK |
| | | 1159.12 | NHATAWQGFK |
| | | 1243.14 | VDDIAVDLVER |
| | | 1261.22 | LWEQVMQLSK |
| | | 1272.24 | SLGKEPEDQNR |
| | | 1277.18 | DGISNTFSIVPK |
| | | 1289.21 | AGVITGLPDAYGR |
| | | 1315.19 | TSTFLDIYAER |
| | | 1322.21 | LREELSEQYR |
| | | 1394.16 | THNQGVFDAYSR |
| | | 1417.32 | KAGVITGLPDAYGR |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1426.23 | IEMALHDTEIVR |
| | | 1487.19 | NHATAWQGFKNGR |
| | | 1508.25 | AGEPFAPGANPMHGR |
| | | 1513.21 | VALYGVDFLMEEK |
| | | 1522.25 | KTHNQGVFDAYSR |
| | | 1543.26 | YGFDLSRPAENFK |
| | | 1571.23 | TSSIQYENDDIMR |
| | | 1636.29 | KAGEPFAPGANPMHGR |
| | | 1703.43 | DLETIVGVQTEKPFK |
| | | 1751.45 | EAVQWLYLAYLAAIK |
| | | 1859.53 | DLETIVGVQTEKPFKR |
| | | 1876.50 | TMATGIAGLSVAADSLSAIK |
| | | 1936.37 | NEEGLVVDFEIEGDFPK |
| | | 2042.43 | MHDFNTMSTEMSEDVIR |
| | | 2077.45 | YGNNDDRVDDIAVDLVER |
| | | 2158.57 | AGVITESEVQEIIDHFIMK |
| | | 2284.61 | ETLIDAMEHPEEYPQLTIR |
| | | 2574.77 | FLHSLDNLGPAPEPNLTVLWSVR |
| | | 2627.61 | SGAQVGPNFEGINSEVLEYDEVFK |
| | | 2355.70 | SGAQVGPNFEGINSEVLEYDEVFKK |
| | | 2907.66 | EFIQLNYTLYEGNDSFLAGPTEATSK |
| | | 3261.91 | VASTITSHDAGYLDKDLETIVGVQTEKPFK |
| | | 3421.02 | TPDYNELFSGDPTWVTESIGGVGIDGRPLVTK |
| P480 | 65 | 625.35 | HVDVR |
| | | 717.38 | YSYER |
| | | 733.42 | LPDNFK |
| | | 736.44 | IIGDYR |
| | | 814.33 | IFTDYR |
| | | 853.31 | YGNNDDR |
| | | 942.33 | IFTDYRK |
| | | 944.39 | ELKELGQK |
| | | 974.52 | YAQVKPIR |
| | | 984.36 | QMQFFGAR |
| | | 992.44 | SMQPFGGIR |
| | | 1049.44 | TLLYAINGGK |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1087.43 | EQQLDVISR |
| | | 1097.51 | VSGYAVNFIK |
| | | 1159.52 | NHATAWQGFK |
| | | 1289.53 | AGVITGLPDAYGR |
| | | 1315.51 | TSTFLDIYAER |
| | | 1322.46 | LREELSEQYR |
| | | 1394.50 | THNQGVFDAYSR |
| | | 1417.65 | KAGVITGLPDAYGR |
| | | 1442.56 | IEMALHDTEIVR + Oxidation (M) |
| | | 1467.60 | VSGYAVNFIKLTR |
| | | 1522.61 | KTHNQGVFDAYSR |
| | | 1524.55 | AGEPFAPGANPMHGR + Oxidation (M) |
| | | 1529.64 | VALYGVDFLMEEK + Oxidation (M) |
| | | 1543.62 | YGFDLSRPAENFK |
| | | 1652.68 | KAGEPFAPGANPMHGR + Oxidation (M) |
| | | 1671.76 | TSTFLDIYAERDLK |
| | | 1766.76 | VDDIAVDLVERFMTK + Oxidation (M) |
| | | 1876.86 | TMATGIAGLSVAADSLSAIK |
| | | 2077.93 | YGNNDDRVDDIAVDLVER |
| | | 2225.07 | DSEHTMSVLTITSNVVYGKK + Oxidation (M) |
| | | 2575.33 | FLHSLDNLGPAPEPNLTVLWSVR |
| | | 2628.25 | SGAQVGPNFEGINSEVLEYDEVFK |
| | | 2748.36 | NLTSMLDGYAMQCGHHLNINVFNR |
| | | 2756.63 | SGAQVGPNFEGINSEVLEYDEVFKK |
| | | 3001.02 | DEKSGAQVGPNFEGINSEVLEYDEVFK |
| | | 3420.75 | TPDYNELFSGDPTWVTESIGGVGIDGRPLVTK |
| P481 | 55 | 634.33 | AKSNSK |
| | | 883.24 | TFYPEAR |
| | | 1014.24 | QFWGHLVK |
| | | 1131.17 | WIPLMMKGR |
| | | 1207.21 | VINEEFEISK |
| | | 1324.10 | NEDWQLYTAGK |
| | | 1360.28 | TLLFGPFANVGPK |
| | | 1386.31 | LDRPAIESSNER |
| | | 1565.30 | IDEGTDVNFGELTR |
| | | 1584.34 | EFINPLPHISYVR |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1699.29 | EIEPDWNIHVYER |
| | | 1744.36 | EPPGTPPMTVPHLDTR |
| | | 2046.52 | QVTDYVFIGAGGGAIPLLQK |
| | | 2189.43 | TFYPEARNEDWQLYTAGK |
| | | 2806.58 | HLGGFPISGQFLACTNPQVIEQHDAK |
| P482 | 37 | 699.28 | FEYIK |
| | | 729.26 | DAWPLK |
| | | 792.33 | ASVVNFR |
| | | 852.28 | VYDQLSK |
| | | 1008.30 | LIDDLYEK |
| | | 1020.31 | YKDAWPLK |
| | | 1083.43 | LKPDLIVASK |
| | | 1278.36 | IAPTVSTDTVFK |
| | | 1623.44 | IVGQEPAPNLEEISK |
| | | 1712.62 | ESIPLMNADHIFVVK |
| | | 1800.61 | IYAGGYAGEILNDLGFK |
| | | 1956.77 | IYAGGYAGEILNDLGFKR |
| | | 2251.77 | NNQVSDDLDEITWNLAGGYK |
| | | 3227.44 | VVTLYQGATDVAVSLGVKPVGAVESWTQKPK |
| P483 | 36 | 646.50 | DVWAR |
| | | 672.41 | KLNAVK |
| | | 716.41 | VDIVDR |
| | | 725.61 | IIKPVR |
| | | 842.50 | IAPTLSLK |
| | | 850.47 | QNINSFK |
| | | 1068.50 | IGDYTSVGTR |
| | | 1075.42 | MIIMTDHAK + Oxidation (M) |
| | | 1185.53 | KQPNLEEISK |
| | | 1327.59 | LKPDLIIADSSR |
| | | 1343.58 | VDIVDRDVWAR |
| | | 1592.76 | LKPDLIIADSSRHK |
| | | 2081.00 | GPYLQLDTEHLADLNPER |
| | | 2438.24 | AGLLAHPNYSYVGQFLNELGFK |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 2789.48 | IVVLEYSFADALAALDVKPVGIADDGK |
| | | 2917.60 | IVVLEYSFADALAALDVKPVGIADDGKK |
| P484 | 35 | 857.38 | AAAIDLAGR |
| | | 1022.23 | NIEADTGMR + Oxidation (M) |
| | | 1056.32 | VVDANIAAQR |
| | | 1075.36 | ADIDLPFER |
| | | 1285.44 | LVGGAGEETIIAR |
| | | 1435.44 | AMAVATEQEMKAR |
| | | 1632.50 | HHTEVLENPDNISK |
| | | 1813.65 | VVEAESEVPLAMAEALR |
| | | 1887.67 | VIETPFIAGVAMNGIEVK |
| | | 2295.85 | AGLALTTNQLESHYLAGGNVDR |
| | | 2806.95 | TVLSKGLDSGTAFEILSIDIADVDISK |
| | | 3337.42 | AGLALTTNQLESHYLAGGNVDRVVDANIAAQR |
| P485 | 33 | 625.28 | ADYEK |
| | | 864.28 | YIAQLEK |
| | | 946.23 | QGTPEQMR |
| | | 1045.26 | ALEQAGKSLK |
| | | 1268.35 | HLLVETSVDKK |
| | | 1443.34 | DEFGEVYTDSIGK |
| | | 1450.40 | TIQQTFIDNDKK |
| | | 1454.37 | VVTTNSILYDMAK |
| | | 1571.45 | KDIFGEVYTDSIGK |
| | | 1576.44 | DVKPIYLNGEEGNK |
| | | 1593.47 | QDPHAQLSLDNGIK |
| | | 1819.59 | DVKPIYLNGEEGNKDK |
| | | 1836.62 | DKQDPHAWLSLDNGIK |
| | | 1911.66 | QYGITPGYIWEINTEK |
| | | 2172.83 | VIAVSKDVKPIYLNGEEGNK |
| | | 2582.00 | LTDADVILYNGLNLETGNGWFEK |
| | | 2942.26 | NVGGDNVDIHSIVPVGQDPHEYEVKPK |
| P486 | 32 | 625.42 | ADYEK |
| | | 864.41 | YIAQLEK |
| | | 1268.48 | HLLVETSVDKK |
| | | 1443.49 | DIFGEVYTDSIGK |

TABLE 4-continued

Characteristics of polypeptides obtained from *S. aureus* isolate 2176.

| Polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1450.53 | TIQQTFIDNDKK |
| | | 1454.61 | VVTTNSILYDMAK |
| | | 1576.64 | DVKPIYLNGEEGNK |
| | | 1593.57 | QDPHAWLSLDNGIK |
| | | 1818.77 | DVKPIYLNGEEGNKDK |
| | | 1836.78 | DKQDPHAWLSLDNGIK |
| | | 1911.81 | QYGITPGYIWEINTEK |
| | | 2582.18 | LTDADVILYNGLNLETGNGWFEK |
| | | 2942.32 | NVGGDNVDIHSIVPVGQDPHEYEVKPK |

[1]Molecular weight as determined by SDS-PAGE.
[2]The m/z value of a polypeptide fragment can be converted to mass by subtracting 1 from the m/z value. Each mass includes a range of plus or minus 400 parts per million (ppm) or 1 Dalton.

TABLE 5

Characteristics of polypeptides obtained from *S. aureus* bovine isolate 1477.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| P487 | 88 | 717.39 | YSYER |
| | | 736.52 | IIGDYR |
| | | 814.46 | IFTDYR |
| | | 942.46 | IFTDYRK |
| | | 974.54 | YAQVKPIR |
| | | 984.41 | QMQFFGAR |
| | | 992.40 | SMQPFGGIR |
| | | 1087.49 | EQQLDVISR |
| | | 1097.50 | VSGYAVNFIK |
| | | 1159.39 | NHATAWQGFK |
| | | 1261.45 | LWEQVMQLSK |
| | | 1272.50 | SLGKEPEDQNR |
| | | 1277.50 | DGISNTFSIVPK |
| | | 1289.54 | AGVITGLPDAYGR |
| | | 1315.54 | TSTFLDIYAER |
| | | 1322.53 | LREELSEQYR |
| | | 1394.50 | THNQGVFDAYSR |
| | | 1417.62 | KAGVITGLPDAYGR |
| | | 1426.65 | IEMALHDTEIVR |

TABLE 5-continued

Characteristics of polypeptides obtained from *S. aureus* bovine isolate 1477.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1508.59 | AGEPFAPGANPMHGR |
| | | 1522.61 | KTHNQGVFDAYSR |
| | | 1543.68 | YGFDLSRPAENFK |
| | | 1877.74 | TMATGIAGLSVAADSLSAIK |
| | | 2077.86 | YGNNDDRVDDIAVDLVER |
| | | 2159.08 | AGVITESEVQEIIDHFIMK |
| | | 2285.07 | ETLIDAMEHPEEYPQLTIR |
| | | 2575.32 | FLHSLDNLGPAPEPNLTVLWSVR |
| | | 2628.24 | SGAQVGPNFEGINSEVLEYDEVFK |
| | | 2756.41 | SGAQVGPNFEGINSEVLEYDEVFKK |
| | | 3262.68 | VASTITSHDAGYLDKDLETIVGVQTEKPFK |
| P488 | 80 | 625.49 | HVDVR |
| | | 814.54 | IFTDYR |
| | | 942.66 | IFTDYRK |
| | | 974.69 | YAQVKPIR |
| | | 984.59 | QMQFFGAR |
| | | 992.55 | SMQPFGGIR |
| | | 1159.64 | NHATAWQGFK |
| | | 1261.63 | LWEQVMQLSK |
| | | 1272.74 | SLGKEPEDQNR |
| | | 1277.69 | DGISNTFSIVPK |
| | | 1289.76 | AGVITGLPDAYGR |
| | | 1315.73 | TSTFLDIYAER |
| | | 1322.72 | SMQPFGGIRMAK |
| | | 1394.73 | THNQGVFDAYSR |
| | | 1417.86 | KAGVITQLPDAYGR |
| | | 1422.76 | TLLYAINGGKDEK |
| | | 1426.80 | IEMALHDTEIVR |
| | | 1508.82 | AGEPFAPGANPMHGR |
| | | 1513.80 | VALYGVDFLMEEK |
| | | 1543.82 | YGFDLSRPAENFK |
| | | 1571.82 | TSSIQYENDDIMR |
| | | 1703.99 | DLETIVGVQTEKPFK |
| | | 1860.23 | DLETIVGVQTEKPFKR |
| | | 1877.07 | TMATGIAGLSVAADSLSAIK |

TABLE 5-continued

Characteristics of polypeptides obtained from *S. aureus* bovine isolate 1477.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1937.09 | NEEGLVVDFEIEGDFPK |
| | | 2078.13 | YGNNDDRVDDIAVDLVER |
| | | 2575.56 | FLHSLDNLGPAPEPNLTVLWSVR |
| | | 2628.30 | SGAQVGPNFEGINSEVLEYDEVFK |
| | | 2908.63 | EFIQLNYTLYEGNDSFLAGPTEATSK |
| P489 | 65 | 733.67 | IVKFAR |
| | | 944.71 | ELKELGQK |
| | | 974.79 | YAQVKPIR |
| | | 984.69 | QMQFFGAR |
| | | 1049.83 | TLLYAINGGK |
| | | 1087.78 | EQQLDVISR |
| | | 1097.79 | VSGYAVNFIK |
| | | 1243.80 | VDDIAVDLVER |
| | | 1272.82 | SLGKEPEDQNR |
| | | 1289.87 | AGVITGLPAYGR |
| | | 1299.92 | LPDNFKTYCAK |
| | | 1315.83 | TSTFLDIYAER |
| | | 1322.84 | SMQPFGGIRMAK |
| | | 1390.93 | DQKGALSSLSSVAK |
| | | 1394.84 | THNQGVFDAYSR |
| | | 1577.94 | VASTITSHDAGYLDK |
| | | 1637.09 | KAGEPFAPGANPMHGR |
| | | 1704.16 | DLETIVGVQTEKPFK |
| | | 2030.42 | MSIKTSSIQYENDDIMR |
| | | 2078.34 | YGNNDDRVDDIAVDLVER |
| | | 2284.60 | ETLIDAMEHPEEYPQLTIR |
| | | 2575.77 | FLHSLDNLGPAPEPNLTVLWSVR |
| | | 2628.64 | SGAQVGPNFEGINSEVLEYDEVFK |
| P490 | 55 | 883.81 | TFYPEAR |
| | | 1014.87 | QFWGHLVK |
| | | 1131.97 | WIPLMMKGR |
| | | 1207.99 | VINEEFEISK |
| | | 1231.97 | YSFDQVIMTK |
| | | 1325.02 | NEDWQLYTAGK |
| | | 1361.17 | TLLFGPFANVGPK |
| | | 1362.14 | GREDNPGIMAASK + Oxidation (M) |

TABLE 5-continued

Characteristics of polypeptides obtained from *S. aureus* bovine isolate 1477.

| polypeptide designation | Approximate molecular weight in kilodaltons (kDa)[1] | m/z value of polypeptide fragments resulting from trypsin digest[2] | Predicted amino acid sequence of the polypeptide fragment |
|---|---|---|---|
| | | 1387.14 | LDRPAIESSNER |
| | | 1481.24 | NEDWQLYTAGKR |
| | | 1566.28 | IDEGTDVNFGELTR |
| | | 1585.34 | EFINPLPHISYVR |
| | | 1700.36 | EIEPDWNIHVYER |
| | | 1761.49 | EPPGTPPMTVPHLDTR + Oxidatiton (M) |
| | | 2047.67 | QVTDYVFIGAGGGAIPLLQK |
| | | 2208.82 | VYGKEPPGTPPMTVPHLDTR + Oxidation (M) |
| | | 2865.21 | HLGGFPISGQFLACTNPQVIEQHDAK |
| P492 | 36 | 857.57 | AAAIDLAGR |
| | | 1056.59 | VVDANIAAQR |
| | | 1075.61 | ADIDLPFER |
| | | 1285.74 | LVGGAGEETIIAR |
| | | 1632.95 | HHTEVLENPDNISK |
| | | 1814.09 | VVEAESEVPLAMAEALR |
| | | 2284.45 | AAAIDLAGRDVLEAVQMSVNPK + OXidation (M) |
| | | 2300.40 | AGLALTTNQLESHYLAGGNVDR |
| | | 2807.80 | TVLSKGLDSGTAFEILSIDIADVDISK |
| P493 | 35 | 762.46 | FVFHGR |
| | | 964.39 | DGFNNIER |
| | | 363.56 | GHVYNGISGGQFK |
| | | 1443.56 | YTPTSILYFNPK |
| | | 1450.64 | QLAEDLQKHLGAK |
| | | 1819.88 | NHSEYVTDMRLIGIR + Oxidation (M) |
| | | 1875.84 | DLPPMEQVFDTLDLDK |
| | | 1941.00 | IRPEDMHIMANIFLPK + Oxidation (M) |
| | | 2081.10 | RIRPEDMHIMANIFLPK |
| | | 2283.30 | ISHLVLTRTGLYIIDSQLLK |
| P495 | 32 | | |

[1]Molecular weight as determined by SDS-PAGE.
[2]The m/z value of a polypeptide fragment can be converted to mass by subtracting 1 from the m/z value. Each mass includes a range of plus or minus 430 parts per million (ppm) or 1 Dalton.

In yet another aspect, the present invention further includes polypeptides having similarity with an amino acid sequence. The similarity is referred to as structural similarity and is generally determined by aligning the residues of the two amino acid sequences (i.e., a candidate amino acid sequence and a reference amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. Reference amino acid sequences are disclosed in Tables 6, 7, 8, and 9. Two amino acid sequences can be compared using commercially available algorithms. Preferably, two amino acid sequences are compared using the BLASTP program of the BLAST 2 search algorithm, as described by Tatusova, et al., (*FEMS Microbiol Lett* 1999, 174:247-250), and available through the World Wide Web, for instance at the internet site maintained by the National Center for Biotechnology Information, National Institutes of Health. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities." Preferably, a candidate amino acid sequence has at least 80% identity, at least 90% identity, at least 95% identity, at least 96% identity, at least 97% identity, at least 98% identity, or at least 99% identity to a reference amino acid sequence. Preferably, the molecular weight of the candidate amino acid sequence and the reference amino acid sequence are substantially the same value. Preferably, the molecular weight of the candidate amino acid sequence and the reference amino acid sequence is determined by SDS polyacrylamide gel electrophoresis. A candidate polypeptide can be obtained by growth of a microbe under low metal conditions and the subsequent isolation of a polypeptide by the procedures disclosed herein.

Typically, a candidate amino acid sequence having structural similarity to a reference amino acid sequence has immunogenic activity, protective immunogenic activity, seroactive activity, immunoregulatory activity, or a combination thereof.

TABLE 6

*S. aureus* ATCC isolate 19636.

| Molecular weight of reference polypeptide (kDa)[1] | NCBI sequence identifier of polypeptide identified by the computer algorithm as having best match to mass fingerprint of reference polypeptide |
|---|---|
| 88 | 49243545 |
| 55 | 81762012 |
| 38 | 82750440 |
| 37 | 49243435 |
| 36 | 57286380 |
| 35 | 49245508 |
| 33 | 49243946 |

[1]Molecular weight as determined by SDS-PAGE.

TABLE 7

*S. aureus* SAAV1.

| Molecular weight of reference polypeptide (kDa)[1] | NCBI sequence identifier of polypeptide identified by the computer algorithm as having best match to mass fingerprint of reference polypeptide |
|---|---|
| 55 | 57286470 |
| 55 | 48874 |
| 37 | 49243435 |
| 33 | 49243946 |

[1]Molecular weight as determined by SDS-PAGE.

TABLE 8

*S. aureus* 2176.

| Molecular weight of reference polypeptide (kDa)[1] | NCBI sequence identifier of polypeptide identified by the computer algorithm as having best match to mass fingerprint of reference polypeptide |
|---|---|
| 88 | 57285406 |
| 80 | 57285406 |
| 65 | 57285406 |
| 55 | 57286528 |
| 37 | 49482358 |
| 36 | 57286380 |
| 35 | 15927153 |
| 33 | 57285658 |
| 32 | 57285658 |

[1]Molecular weight as determined by SDS-PAGE.

TABLE 9

*S. aureus* 1477.

| Molecular weight of reference polypeptide (kDa)[1] | NCBI sequence identifier of polypeptide identified by the computer algorithm as having best match to mass fingerprint of reference polypeptide |
|---|---|
| 88 | 49482458 |
| 80 | 57285406 |
| 65 | 57285406 |
| 55 | 57286528 |
| 36 | 15927153 |
| 35 | 49484031 |

[1]Molecular weight as determined by SDS-PAGE.

The polypeptides expressed by a reference microbe and referred to above by molecular weight can be obtained by growth of the reference microbe under low metal conditions and the subsequent isolation of a polypeptide by the processes disclosed herein. A candidate polypeptide is isolatable from a microbe, preferably a gram positive microbe, more preferably, a member of the family Micrococcaceae, preferably, *Staphylococcus* spp., more preferably, *Staphylococcus aureus*. Other gram positive microbes include *Corynebacterium* spp., *Erysipelothrix* spp., *Mycobacterium* spp., and *Erysipelothrix* spp. A candidate polypeptide may also be produced using recombinant, enzymatic, or chemical techniques.

Also provided by the present invention are whole cell preparations of a microbe, where the microbe expresses one or more of the polypeptides of the present invention. The cells present in a whole cell preparation are preferably inactivated such that the cells cannot replicate, but the immunogenic activity of the polypeptides of the present invention expressed by the microbe is maintained. Typically, the cells are killed by exposure to agents such as glutaraldehyde, formalin, or formaldehyde.

Compositions

A composition of the present invention may include at least one polypeptide described herein, or a number of polypeptides that is an integer greater than 1 (e.g., at least 2, at least 3, at least 4). For example, a composition can include 2, 3, 4, 5, or more isolated metal regulated polypeptides having molecular weights of 88 kDa, 55 kDa, 38 kDa, 37 kDa, 36 kDa, 35 kDa, 33 kDa, or any subset or combination thereof. A composition can include polypeptides isolatable from 1 microbe, or can be isolatable from a combination of 2 or more microbes. For instance, a composition can include polypeptides isolatable from 2 or more *Staphyloccocus* spp., or from a *Staphyloccocus* spp. and a different microbe that is not a member of the genus *Staphyloccocus*. The present invention also provides compositions including a whole cell preparation, where the whole cell expresses one or more of the polypeptides of the present invention. For instance, the whole cell can be a *Staphyloccocus* spp. In some aspects, a composition can include whole preparations from 2, 3, 4, 5, or 6 strains.

Optionally, a polypeptide of the present invention can be covalently bound or conjugated to a carrier polypeptide to improve the immunological properties of the polypeptide. Useful carrier polypeptides are known in the art. The chemical coupling of polypeptides of the present invention can be carried out using known and routine methods. For instance, various homobifunctional and/or heterobifunctional cross-linker reagents such as bis(sulfosuccinimidyl) suberate, bis (diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (I-ethyl-3-(dimethyl-aminopropyl) carbodiimide can be used (see, for instance, Harlow and Lane, Antibodies, A Laboratory Manual, generally and Chapter 5, Cold Spring Harbor Laboratory, Cold Spring Harbor, N.Y., N.Y. (1988)).

The compositions of the present invention optionally further include a pharmaceutically acceptable carrier. "Pharmaceutically acceptable" refers to a diluent, carrier, excipient, salt, etc, that is compatible with the other ingredients of the composition, and not deleterious to the recipient thereof. Typically, the composition includes a pharmaceutically acceptable carrier when the composition is used as described herein. The compositions of the present invention may be formulated in pharmaceutical preparations in a variety of forms adapted to the chosen route of administration, including routes suitable for stimulating an immune response to an antigen. Thus, a composition of the present invention can be administered via known routes including, for example, oral; parental including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. it is foreseen that a composition can be administered to a mucosal surface, such as by administration to the nasal or respiratory mucosa (e.g. spray or aerosol), in order to stimulate mucosal immunity, such as production of secretory IgA antibodies, throughout the animal's body.

A composition of the present invention can also be administered via a sustained or delayed release implant. Implants suitable for use according to the invention are known and include, for example, those disclosed in Emery and Straub (WO 01/37810 (2001)), and Emery et al., (WO 96/01620 (1996)). Implants can be produced at sizes small enough to be administered by aerosol or spray. Implants also include nanospheres and microspheres.

A composition of the present invention may be administered in an amount sufficient to treat certain conditions as described herein. The amount of polypeptides or whole cells present in a composition of the present invention can vary. For instance, the dosage of polypeptides can be between 0.01 micrograms (µg) and 300 mg, typically between 0.1 mg and 10 mg. When the composition is a whole cell preparation, the cells can be present at a concentration of, for instance, $10^2$ bacteria/ml, $10^3$ bacteria/ml, $10^4$ bacteria/ml, 10 bacteria/ml, $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptides may be present in the composition in an amount such that the total volume of the composition administered is 0.5 ml to 5.0 ml, typically 1.0-2.0 mi. When the composition is a whole cell preparation, the cells are preferably present in the composition in an amount that the total volume of the composition administered is 0.5 ml to 5.0 ml, typically 1.0-2.0 mi. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al., (U.S. Pat. No. 6,027,736).

The formulations may be conveniently presented in unit dosage form and may be prepared by methods well known in the art of pharmacy. Methods of preparing a composition with a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyl dioctadecyl ammonium bromide (DDA), avridine, aluminum hydroxide, oils, saponins, alpha-tocopherol, polysaccharides, emulsified paraffins (including, for instance, those available from under the tradename EMULSIGEN from MVP Laboratories, Ralston, Nebr.), ISA-70, RIBI and other substances known in the art. It is expected that polypeptides of the present invention will have immunoregulatory activity and that such polypeptides may be used as adjuvants that directly act as T and/or B cell activators or act on specific cell types that enhance the synthesis of various cytokines or activate intracellular signaling pathways. Such polypeptides are expected to augment the immune response to increase the protective index of the existing composition.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. An immunizing composition can also include other components known in the art such as an antibiotic, a preservative, an anti-oxidant, or a chelating agent.

Methods of Making

The present invention also provides methods for obtaining the polypeptides described herein. The polypeptides and whole cells of the present invention are isolatable from a member of the family Micrococcaceae, preferably, *Staphylococcus* spp., more preferably, *Staphylococcus aureus*. Other gram positive microbes from which polypeptides can be isolated include *Corynebacterium* spp., *Erysipelothrix* spp., *Mycobacterium* spp., and *Erysipelothrix* spp. Microbes useful for obtaining polypeptides of the present invention and making whole cell preparations are commercially available from a depository such as American Type Culture Collection (ATCC). In addition, such microbes are readily obtainable by techniques routine and known to the art. The microbes may be derived from an infected animal as a field isolate, and used to obtain polypeptides and/or whole cell preparations of the present invention, or stored for future use, for example, in a frozen repository at $-20°$ C. to $-95°$ C., or $-40°$ C. to $-50°$ C., in bacteriological media containing 20% glycerol, and other like media.

When a polypeptide of the present invention is to be obtained from a microbe, the microbe can be incubated under low metal conditions. As used herein, the phrase "low metal conditions" refers to an environment, typically bacteriological media, which contains amounts of a free metal that cause a microbe to express metal regulated polypeptides at a detectable level. As used herein, the phrase "high metal conditions" refers to an environment that contains amounts of a free metal that cause a microbe to either not express one or more of the metal regulated polypeptides described herein at a detectable level, or to decrease expression of such a polypeptide. Metals are those present in the periodic table under Groups 1 through 17 (IUPAC notation; also referred to as Groups I-A, II-A, III-B, IV-B, V-B, VI-B, VII-B, VIII, I-B, I-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

Low metal conditions are generally the result of the addition of a metal chelating compound to a bacteriological medium, the use of a bacteriological medium that contains low amounts of a metal, or the combination thereof. High metal conditions are generally present when a chelator is not present in the medium, a metal is added to the medium, or the combination thereof. Examples of metal chelators include natural and synthetic compounds. Examples of natural compounds include plant phenolic compounds, such as flavenoids. Examples of flavenoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis (2-pyridylmethyl)-ethylene diamine. Examples of synthetic iron chelators include 2,2'-dipyridyl (also referred to in the art as $\alpha,\alpha'$-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. An example of a general divalent cation chelator is Chelex® resin. Preferably, 2,2'-dipyridyl is used for the chelation of iron. Typically, 2,2'-dipyridyl is added to the media at a concentration of at least 300 micrograms/milliliter (µg/ml), at least 600 µg/ml, or at least 900 µg/ml. High levels of 2,2'-dipyridyl can be 1200 µg/ml, 1500 µg/ml, or 1800 µg/ml.

The *S. aureus* genome encodes three Fur homologs: Fur, PerR, and Zur. While the Zur and PerR proteins appear to be primarily involved in regulating zinc homeostasis and peroxide stress genes, respectively, the Fur protein has been demonstrated to regulate several iron-siderophore uptake systems in response to iron limitation. The Fur protein also plays a role in oxidative stress resistance and virulence. It is expected that a gram positive organism, preferably, an *S. aureus*, with a mutation in a fur gene will result in the constitutive expression of many, if not all, of the metal regulated polypeptides of the present invention. The production of a fur mutation in a gram positive, preferably, an *S. aureus*, can be produced using routine methods including, for instance, transposon, chemical, or site-directed mutagenesis useful for generating gene knock-out mutations in gram positive bacteria.

The medium used to incubate the microbe and the volume of media used to incubate the microbe can vary. When a microbe is being evaluated for the ability to produce one or more of the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermentor to allow the isolation of larger amounts of polypeptides. Methods for growing microbes in a fermentor are routine and known to the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C.

In some aspects of the invention, a microbe may be harvested after growth. Harvesting includes concentrating the microbe into a smaller volume and suspending in a media different than the growth media. Methods for concentrating a microbe are routine and known in the art, and include, for example, filtration or centrifugation. Typically, the concentrated microbe is suspended in an appropriate buffer. An example of a buffer that can be used contains Tris-base (7.3 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at $-20°$ C. or below until disrupted.

When the microbe is to be used as a whole cell preparation, the harvested cells may be processed using routine and known methods to inactivate the cells. Alternatively, when a microbe is to be used to prepare polypeptides of the present invention, the microbe may be disrupted using chemical, physical, or mechanical methods routine and known to the art, including, for example, boiling, french press, sonication, digestion of peptidoglycan (for instance, by digestion with lysozyme), or homogenization. An example of a suitable device useful for homogenization is a model C500-B Avestin Homogenizer, (Avestin Inc, Ottawa Canada). As used herein, "disruption" refers to the breaking up of the cell. Disruption of a microbe can be measured by methods that are routine and known to the art, including, for instance, changes in optical density. Typically, a microbe is subjected to disruption until the percent transmittance is increased by 20% when a 1:100 dilution is measured. When physical or mechanical methods are used, the temperature during disruption is typically kept low, preferably at 4° C., to further minimize proteolytic degradation. When chemical methods are used the temperature may be increased to optimize for the cell disruption. A combination of chemical, physical, and mechanical methods may also be used to to solubilize the cell wall of microbe. As used herein, the term "solubilize"

refers to dissolving cellular materials (e.g., polypeptides, nucleic acids, carbohydrates) into the aqueous phase of the buffer in which the microbe was disrupted, and the formation of aggregates of insoluble cellular materials. Without intending to be limited by theory, the conditions for solubilization are believed to result in the aggregation of polypeptides of the present invention into insoluble aggregates that are large enough to allow easy isolation by, for instance, centrifugation.

The insoluble aggregates that include one or more of the polypeptides of the present invention may be isolated by methods that are routine and known to the art. Preferably, the insoluble aggregates are isolated by centrifugation. Typically, centrifugation of polypeptides, such as membrane polypeptides, can be accomplished by centrifugal forces of 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of continuous flow centrifuges, for instance T-1 Sharpies (Alfa Laval Separations, Warminster, Pa.), which can be used with a flow rate of 250 ml/minute at 17 psi at a centrifugal force of 46,000×g to 60,000×g. Other large scale centrifuges can be used, such as the tubular bowl, chamber, and disc configurations. Such centrifuges are routinely used and known in the art, and are commercially available from such manufactures as Pennwalt, Westfalia and alpha-Laval.

The final harvested proteins are washed and/or dialyzed against an appropriate buffer using methods known in the art, for instance diafiltration, precipitation, hydrophobic chromatography, ion-exchange chromatography, or affinity chromatography, or ultra filtration and washing the polypeptides, for instance, in alcohol, by diafiltration. After isolation, the polypeptides suspended in buffer and stored at low temperature, for instance, −20° C. or below.

In those aspects of the present invention where a whole cell preparation is to be made, after growth a microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

Methods of Use

An aspect of the present invention is further directed to methods of using the compositions of the present invention. The methods include administering to an animal an effective amount of a composition of the present invention. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, dogs or cats), members of the family Cervidae (including, for instance, deer, elk, noose, caribou and reindeer), or human.

In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that in some aspects of the present invention annual boosters will not be necessary, as an animal will be challenged in the field by exposure to microbes expressing polypeptides present in the compositions having epitopes that are identical to or structurally related to epitopes present on polypeptides of the composition administered to the animal.

In one aspect, the invention is directed to methods for making antibodies, for instance by inducing the production of antibody in an animal, or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein. The present invention further includes antibody that specifically bind to a polypeptide of the present invention, and compositions including such antibodies. The method may be used to produce antibody that specifically binds polypeptides expressed by a microbe other than the microbe from which the polypeptides of the composition were isolated. As used herein, an antibody that can "specifically bind" a polypeptide is an antibody that interacts with the epitope of the antigen that induced the synthesis of the antibody, or interacts with a structurally related epitope. At least some of the polypeptides present in the compositions of the present invention typically include epitopes that are conserved in the polypeptides of different species and different genera of microbes. Accordingly, antibody produced using a composition derived from one microbe is expected to bind to polypeptides expressed by other microbes and provide broad spectrum protection against gram positive organisms. Examples of gram positive microbes to which the antibody may specifically bind are Micrococcaceae, preferably, *Staphylococcus* spp., more preferably, *Staphylococcus aureus*; members of the family Streptococcaceae, preferably, *Streptococcus pyogenes, Streptococcus pneumoniae, Streptococcus agalactiae, Streptococcus uberis, Streptococcus bovis, Streptococcus equi*, or *Streptococcus dysgalactiae*; and *Bacillus* spp., *Clostridium* spp., *Corynebacterium* spp., *Enterococcus* spp., *Erysipelothrix* spp., *Listeria* spp., *Micrococcus* spp., and *Mycobacterium* spp., *Kytococcus* spp., and *Erysipelothrix* spp.

The present invention is also directed to the use of such antibody to target a microbe expressing a polypeptide of the present invention or a polypeptide having an epitope structurally related to an epitope present on a polypeptide of the present invention. A compound can be covalently bound to an antibody, where the compound can be, for instance, a toxin. Likewise, such compounds can be covalently bound to a bacterial siderophore to target the microbe. The chemical coupling or conjugation of an antibody of the present invention, or a portion thereof (such as an Fab fragment), can be carried out using known and routine methods. In one aspect the invention is also directed to treating an infection in an animal, including a human, caused by a gram positive microbe, preferably by a member of the family Micrococcaceae, preferably, *Staphylococcus* spp., more preferably, *S. aureus*; members of the family Streptococcaceae, preferably, *Streptococcus pyogenes, Streptococcus pneumoniae, Streptococcus agalactiae, Streptococcus uberis, Streptococcus bovis, Streptococcus equi*, or *Streptococcus dysgalactiae*; *Bacillus* spp., *Clostridium* spp., *Corynebacterium* spp., *Enterococcus* spp., *Erysipelothrix* spp., *Kytococcus* spp.,

*Listeria* spp., *Micrococcus* spp., *Mycobacterium* spp., and *Erysipelothrix* spp. As used herein, the term "infection" refers to the presence of a gram positive microbe in an animal's body, which may or may not be clinically apparent. An animal with an infection by a member of the genus *Staphylococcus* that is not clinically apparent is often referred to as an asymptomatic carrier. The method includes administering an effective amount of the composition of the present invention to an animal having an infection caused by a gram positive microbe, and determining whether the number of microbes causing the infection has decreased. Methods for determining whether an infection is caused by a gram positive microbe are routine and known in the art, as are methods for determining whether the infection has decreased.

In another aspect, the present invention is directed to methods for treating one or more symptoms of certain conditions in an animal that may be caused by infection by a gram positive microbe, preferably by a member of the family Micrococcaceae, preferably, *Staphylococcus* spp., more preferably, *S. aureus*; members of the family Streptooococcaceae, preferably, *Streptococcus pyogenes, Streptococcus pneumoniae, Streptococcus agalactiae, Streptococcus uberis, Streptococcus bovis, Streptococcus equi*, or *Streptococcus dysgalactiae; Bacillus* spp., *Clostridium* spp., *Corynebacterium* spp., *Enterococcus* spp., *Erysipelothrix* spp., *Kytococcus* spp., *Listeria* spp., *Micrococcus* spp., *Mycobacterium* spp., and *Erysipelothrix* spp. The method includes administering an effective amount of a composition of the present invention to an animal having or at risk of having a condition, or symptoms of a condition, and determining whether at least one symptom of the condition is changed, preferably, reduced. Examples of conditions caused by microbial infections include, for instance, mastitis, septicemia, pneumonia, meningoencephalitis, lymphangitis, dermatitis, genital tract infections, strangles, metritis, perinatal disease, pituitary abscesses, arthritis, bursitis, orchitis, cystitis and pyelonephritis, caseous lymphadenitis, tuberculosis, ulcerative lymphangitis, listeriosis, erysipelas, laminitis, anthrax, tyzzer's disease, tetanus, botulism, enteritis, malignant edema, braxy, bacillary hemoglobinuria, enterotoxemia, necrotic skin lesions, and nosocomial infections. Examples of conditions caused by *S. aureus* also include, for instance, botryomycosis in horses, purulent synovitis and osteomyelitis in poultry, abortions in swine, and tick pyemia in lambs. Examples of conditions caused by *Streptococcus* spp. also include, for instance, sore throat, scarlet fever, impetigo, ulcerative endocarditis, rheumatic fever and post streptococcal glomerulonephritis cervicitis in humans, cervicitis in equine and swine, and meningitis and jowl abscesses in swine.

Treatment of symptoms associated with these conditions can be prophylactic or, alternatively, can be initiated after the development of a condition described herein. As used herein, the term "symptom" refers to objective evidence in a subject of a condition caused by infection by a microbe. Symptoms associated with conditions referred to herein and the evaluations of such symptoms are routine and known in the art. Treatment that is prophylactic, for instance, initiated before a subject manifests symptoms of a condition caused by a microbe, is referred to herein as treatment of a subject that is "at risk" of developing the condition. Typically, an animal "at risk" of developing a condition is an animal present in an area where animals having the condition have been diagnosed and/or is likely to be exposed to a microbe causing the condition. Accordingly, administration of a composition can be performed before, during, or after the occurrence of the conditions described herein. Treatment initiated after the development of a condition may result in decreasing the severity of the symptoms of one of the conditions, or completely removing the symptoms. In this aspect of the invention, an "effective amount" is an amount effective to prevent the manifestation of symptoms of a disease, decrease the severity of the symptoms of a disease, and/or completely remove the symptoms. The successful treatment of a gram positive microbial infection in an animal is disclosed in Example 5, which demonstrates the protection against disease caused by *S. aureus* in mouse models by administering a composition of the present invention. These mouse models are a commonly accepted model for the study of human disease caused by these microbes. The successful treatment of a gram positive microbial infection in an animal is also disclosed in Examples 10-12, which demonstrates the protection against disease caused by *S. aureus* in cows by administering a composition of the present invention.

The present invention also provides methods for decreasing colonization by gram positive microbes, for instance blocking the attachment sites of gram positive microbe, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioceles, alveoli), digestive system (for instance, mouth, salivary glands oesophagus liver stomach large and small intestine), excretory system (for instance, kidneys, ureters, bladder and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, lymphocytes t- and b-cells), and specific cell lineages (for instance, precursor cells, epithelial cells, stem cells), and the like. Preferably, the gram positive microbe is a member of the family Micrococcaceae, preferably, *Staphylococcus* spp., more preferably, *S. aureus*; a member of the family Streptoocccaceae, preferably, *Streptococcus pyogenes, Streptococcus pneumoaniae, Streptococcus agalactiae, Streptococcus uberis, Streptococcus bovis, Streptococcus equi*, or *Streptococcus dysgalactiae; Bacillus* spp., *Clostridium* spp., *Corynebacterium* spp., *Enterococus* spp., *Erysipelothrix* spp., *Kytococcus* spp., *Listeria* spp., *Micrococcus* spp., *Mycobacterium* spp., and *Erysipelothrix* spp. The method includes administering an effective amount of a composition of the present invention to an animal colonized by, or at risk of being colonized by, a gram positive microbe. In this aspect of the invention, an "effective amount" is an amount sufficient to decrease colonization of the animal by the microbe. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to humans.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24): 10029-33; Daugherty et al., Nucleic Acids Res., 1991, 19(9): 2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, F(ab)$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a polypeptide of the present invention or a polypeptide having an epitope structurally related to an epitope present on a polypeptide of the present invention.

Animal models, in particular mouse models, are available for experimentally evaluating the compositions of the present invention. These mouse models are commonly accepted models for the study of human disease caused by members of the genus *Staphylococcus*, and *S. aureus* in particular. In those cases where a members of the genus *Staphylococcus* causes disease in an animal, for instance a cow, the natural host can be used to experimentally evaluate the compositions of the present invention.

Another aspect of the present invention provides methods for detecting antibody that specifically binds polypeptides of the present invention. These methods are useful in, for instance, detecting whether an animal has antibody that specifically binds polypeptides of the present invention, and diagnosing whether an animal may have a condition caused by a microbe expressing polypeptides described herein, or expressing polypeptides that share epitopes with the polypeptides described herein. Such diagnostic systems may be in kit form. The methods include contacting an antibody with a preparation that include a polypeptide of the present invention to result in a mixture. The antibody may be present in a biological sample, for instance, blood, milk, or colostrum. The method further includes incubating the mixture under conditions to allow the antibody to specifically bind the polypeptide to form a polypeptide:antibody complex. As used herein, the term polypeptide:antibody complex refers to the complex that results when an antibody specifically binds to a polypeptide. The preparation that includes the polypeptides of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence or peroxidase. The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The antibody detected may be obtained from an animal suspected to have an infection caused by a gram positive microbe, more preferably, a member of the family Micrococcaceae, preferably, *Staphylococcus* spp., more preferably, *S. aureus*; *Streptococcus* spp., *Bacillus* spp., *Clostridium* spp., *Corynebacterium* spp., *Enterococus* spp., *Erysipelothrix* spp., *Kytococcus* spp., *Listeria* spp., *Micrococcus* spp., *Mycobacterium* spp., and *Erysipelothrix* spp.

The kit includes at least one of the polypeptides of the present invention, or a number of polypeptides that is an integer greater than 1 (e.g., at least 2, at least 3, etc.), in a suitable packaging material in an amount sufficient for at least one assay. Optionally, other reagents such as buffers and solutions needed to practice the invention are also included. For instance, a kit may also include a reagent to permit detection of an antibody that specifically binds to a polypeptide of the present invention, such as a detectably labeled secondary antibody designed to specifically bind to an antibody obtained from an animal. Instructions for use of the packaged polypeptides are also typically included. As used herein, the phrase "packaging material" refers to one or more physical structures used to house the contents of the kit. The packaging material is constructed by well known methods, generally to provide a sterile, contaminant-free environment. The packaging material may have a label which indicates that the polypeptides can be used for detecting antibody that specifically binds polypeptides of the present invention. In addition, the packaging material contains instructions indicating how the materials within the kit are employed to detect the antibody. As used herein, the term "package" refers to a container such as glass, plastic, paper, foil, and the like, capable of holding within fixed limits the polypeptides, and other reagents, for instance a secondary antibody. Thus, for example, a package can be a microtiter plate well to which microgram quantities of polypeptides have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples,

EXAMPLES

Example 1

Preparation of Iron Regulated Proteins Laboratory Scale

Compositions derived from different strains of *Staphylococcus aureus* including novel proteins expressed under iron-restriction and/or other degrees of metal ion chelation were evaluated for efficacy against a virulent challenge in mice. The efficacy of the composition was evaluated by collecting data on the following parameters (1) the efficacy of each composition to provide homologous and heterologous protection against a live virulent challenge in mice, (2) the efficacy of each composition to reduce necrotic skin lesions, and (3) the efficacy of compositions derived from *Staphylococcus* grown in replete and deplete iron conditions to provide protection.

The *Staphylococcus aureus* strains evaluated in this study originated from three animal species; avian, human and bovine. The avian isolate SAAV1 was a field isolate originating from a flock of diseased turkeys having a high degree of osteomyelitis and synovitis. The bovine isolates (strain 1477 and strain 2176) were isolated from two different commercial dairy herds having a high incidence of clinical mastitis. The human isolate was obtained from the ATCC (strain 19636), and originated from a patient having clinical osteomyelitis.

Master seed stocks of each isolate were prepared by inoculating the appropriate isolate into 200 ml of Tryptic Soy Broth (TSB, Difco Laboratories. Detroit, Mich.) containing 300 μM 2,2-dipyridyl (Sigma-Aldrich St. Louis, Mo.). The culture was grown while stirring at 200 rpm for 6 hours at 37'C, and collected by centrifugation at 10,000×g. The bacterial pellet was re-suspended into 100 ml TSB broth containing 20% glycerol, and sterilely dispensed into 2 ml cryogenic vials (1 ml per vial) and stored at −90° C. until use.

Each master seed stock was expanded into a working seed. One vial of each master seed isolate was inoculated into 200 ml of Tryptic Soy Broth (TSB, Difco Laboratories, Detroit, Mich.) containing 1000 μM 2,2-dipyridyl (Sigma-Aldrich St. Louis, Mo.). The culture was grown while stirring at 200 rpm for 6 hours at 37° C. and collected by centrifugation at 10,000×g. The bacterial pellet was resuspended into 100 ml TSB broth containing 20% glycerol, and sterilely dispensed into 2 ml cryogenic vials (1 ml per vial) and stored at −90° C. until use. The working seed was used for the production of compositions enriched with iron-regulated membrane proteins, including iron-regulated membrane proteins.

All strains were adapted to grow in highly iron-depleted media (i.e., media containing very low levels of free iron). This was accomplished by sub-culturing the bacteria in TSB containing increasing concentrations of 2,2-dipyridyl (from 300 to 1600 μM).

Proteins were prepared from bacteria as follows. The bacteria were grown from frozen working seed stocks by subculturing into 25 ml of iron-deplete media (containing 1000 μM 2,2'-dyipyridyl) and iron-replete media, then incubated at 37° C. while shaking at 400 rpm. Following 12 hours of incubation, 5 ml of each culture was transferred into 500 ml of iron-deplete or iron-replete media pre-incubated at 37° C. Cultures were incubated for 8 hours at 37° C. while shaking at 100 rpm, then cells were pelleted by centrifugation at 10,000×g for 20 minutes. Bacterial pellets were resuspended in 100 ml of sterile physiological saline and centrifuged at 10,000×g for 10 minutes. Pellets were then resuspended in 45 ml of Tris-buffered saline, pH 7.2 (TBS; 25 mM Tris, 150 mM NaCl) and the resulting bacterial suspensions were dispensed as 9-ml aliquots into 5 individual tubes. One milliliter of TBS containing 50 units of lysostaphin (Sigma, St. Louis, Mo.) was added to each tube to give a final volume of 5 units/mi. Following incubation at 37° C. for 30 minutes while shaking at 200 rpm, 1 ml of TBS containing 0.1 mg of lysozyme (Sigma) was added to each tube. The bacterial suspensions were then incubated for an additional 45 minutes while shaking at 200 rpm. Next, suspensions were centrifuged at 3050×g for 12 minutes at 4° C. to pellet large cellular debris. The supernatants were collected by aspiration without disturbing the pellet. The supernatant was then centrifuged at 39,000×g for 2.5 hours. The resulting pellets containing the proteins were resuspended into 200 μL Tris buffer, pH 7.2, without saline. The protein solution for each isolate were combined for a total volume of 1 ml and stored at −90° C.

The protein-enriched extracts derived from *S. aureus* were size-fractionated on SDS-PAGE gels using a 4% stacking gel and 10% resolving gel. Samples for electrophoresis were prepared by combining 10 μl of sample with 30 μl of SDS reducing sample buffer (62.5 mM Tris-HCL pH 6.8, 20% glycerol, 2% SDS, 5% β-mercaptoethanol) and boiled for 4 minutes. Samples were electrophoresed at 18 mA constant current for 5 hours at 4° C. using a Protein 11 xi cell power supply (BioRad Laboratories, Richmond, Calif., model 1000/500). The molecular weight of each individual protein as visually seen in the SDS-PAGE gel was estimated using a GS-800 densitometer (BioRad) using a broad range molecular weight marker as a reference standard (BioRad).

The SDS-PAGE patterns of the proteins from each isolate when grown in the presence of 1600 μM dipyridyl showed a very different protein expression pattern compared to the same strain when grown in the presence of 300 μM dipyridyl. For instance, when grown in 300 μM dipyridyl isolate SAAV1 resulted in metal regulated proteins of 90 kDa, 84 kDa, 72 kDa, 66 kDa, 36 kDa, 32 kDa, and 22 kDa, while growth in 1600 μM dipyridyl resulted in metal regulated proteins of 87.73 kDa, 54.53 kDa, 38.42 kDa, 37.37 kDa, 35.70 kDa, 34.91 kDa, and 33.0 kDa. Likewise, when grown in 300 μM dipyridyl isolate 19636 resulted in proteins of 42 kDa and 36 kDa, while growth in 1600 μM dipyridyl resulted in metal regulated proteins of 87.73 kDa, 54.53 kDa, 38.42 kDa, 37.37 kDa, 35.70 kDa, 34.91 kDa, and 33.0 kDa. All conditions, including growth in iron-replete media, resulted in the expression of the following proteins that were presumably not metal regulated: 150 kDa, 132 kDa, 120 kDa, 75 kDa, 58 kDa, 50 kDa, 44 kDa 43 kDa 41 kDa, and 40 kDa.

Furthermore, growth of the different strains of *S. aureus* in 1600 μM dipyridyl resulted in similar protein expression patterns. The compositions enriched in iron-regulated membrane proteins from the avian isolate (SAAV1) included proteins with molecular weights of 87.73 kDa, 54.53 kDa, 38.42 kDa, 37.37 kDa, 35.70 kDa, 34.91 kDa, and 33.0 kDa. The molecular weights of the proteins from the ATCC isolate 19636 were essentially identical to those from the avian isolate. Both bovine isolates, when grown with 1600 μM 2,2-dipyridyl, expressed similar banding profiles as the avian and ATCC isolates for the majority of the proteins (87.73 kDa, 54.53 kDa, 37.7 kDa, 35.70 kDa, 34.91 kDa, and 33.0 kDa). However, neither of the bovine isolates produced the 38.42 kDa protein seen with the avian and ATCC isolates, and the bovine isolates expressed three proteins (80.46 kDa, 65.08 kDa, and 31.83 kDa) not observed with the avian and ATCC strains (see FIG. 1 and Table 10). All conditions resulted in the expression of the following proteins that were not metal regulated: 150 kDa, 132 kDa, 120 kDa, 75 kDa, 58 kDa, 50 kDa, 44 kDa, 43 kDa, 41 kDa, and 40 kDa.

TABLE 10

Molecular weights of metal regulated polypeptides obtained from *Staphylococcus aureus* isolates.

| Avian SAAV1 | Human 19636 | Bovine 1477 | Bovine 2176 |
|---|---|---|---|
| 87.73 | 87.73 | 87.73 | 87.73 |
| — | — | 80.46 | 80.46 |
| — | — | 65.08 | 65.08 |
| 54.53 | 54.53 | 54.53 | 54.53 |
| 38.42 | 38.42 | — | — |
| 37.37 | 37.37 | 37.37 | 37.37 |
| 35.70 | 35.70 | 35.70 | 35.70 |
| 34.91 | 34.91 | 34.91 | 34.91 |
| 33.0 | 33.0 | 33.0 | 33.0 |
| | | 31.83 | 31.83 |

Interestingly, there was no difference in the protein profiles as examined by SDS-PAGE between the clarified supernatant and the bacterial pellet after treating the bacteria with lysostaphin/lysozyme. Both the extracted bacterial pellet and the supernatant had exactly the same protein profiles as examined by SDS-PAGE. This same observation was also seen when disrupting the bacterial cells using an Avestin homogenizer at 30,000 psi. The resultant bacterial pellet, after slow speed centrifugation was identical in its protein profile as compared to the clarified supernatant after high speed centrifugation at 30,000×g for 2.0 hours at 4° C.

Example 2

Preparation of the Immunizing Compositions Derived from *Staphylococcus aureus*

The proteins from the human isolate ATCC 19636 and the bovine isolate 1477, grown in iron-deplete conditions and prepared as described in Example 1, were used to formulate two vaccine compositions. The proteins from the ATCC isolate had molecular weights of 87.73 kDa, 54.53 kDa, 38.42 kDa, 37.37 kDa, 35.70 kDa, 34.91 kDa, and 33.0 kDa, while the bovine isolate expressed proteins having molecular weights 87.73 kDa, 80.46 kDa, 65.08 kDa, 54.53 kDa, 37.37 kDa, 35.70 kDa, 34.91 kDa, 33.0 kDa, and 31.83. Each composition also contained the following proteins that were not metal regulated: 150 kDa, 132 kDa, 120 kDa, 75 kDa, 58 kDa, 50 kDa, 44 kDa, 43 kDa, 41 kDa, and 40 kDa. Stock vaccines were prepared from the two strains by emulsifying each aqueous protein suspension (500 μg total protein/ml) into a commercial adjuvant (EMULSIGEN, MVP Laboratories, Ralston, Nebr.) using an IKA Ultra Turrax T-50 homogenizing vessel (IKA, Cincinnati, Ohio) to give a final dose of 50 μg total protein in a 0.1 ml injectable volume with an adjuvant concentration of 22.5% vol/vol. As a control vaccination, a protein composition was prepared from the bovine isolate 1477 grown under iron-replete conditions (TSB supplemented with 300 μM ferric chloride) as described in Example 1. A placebo vaccine was prepared by substituting physiological saline for the aqueous protein suspension in the above protocol.

Example 3

Mouse Vaccination

Seventy (N=70) female CF-1 mice obtained from Harlan Breeding Laboratories (Indianapolis, Ind.) weighing 16-22 grams were equally distributed into 7 groups (10 mice/group). Mice were housed in polycarbonate mouse cages (Ancore Corporation, Bellmore, N.Y.). A single cage was used for each treatment group and food and water was supplied ad libitum to all mice. All mice were vaccinated intraperitoneally with 0.1 ml of the appropriate composition two times at 14 day intervals as follows:

Group-1: Placebo-Vaccinated

Group-2: Vaccinated with ATCC 19636 proteins expressed under iron-restriction.

Group-3: Placebo-Vaccinated

Group-4: Vaccinated with Bovine 1477 proteins expressed under iron-restriction.

Group-5: Vaccinated with Bovine 1477 proteins expressed under iron-restriction.

Group-6: Vaccinated with ATCC 19636 proteins expressed under iron-restriction.

Group-7: Bovine 1477 FeCl$_3$-Vaccinated, where "Bovine 1477 FeCl$_3$" refers to proteins obtained from Bovine 1477 grown in TSB supplemented with 300 μM ferric chloride.

Example 4

Preparation of Challenge Organism

The previously described *Staphylococcus aureus* strains ATCC 19636 and strain 1477 were used as challenge organisms. Briefly, the isolates from frozen stocks (previously described) were streaked onto blood agar plates and incubated at 37° C. for 18 hours. A single colony of each isolate was subcultured into 50 ml Tryptic Soy Broth (Difco) containing 1600 μM 2,2' dipyridyl. The cultures were incubated at 37° C. for 6 hours while rotating at 200 rpm, then centrifuged at 10,000×g for 10 minutes at 4° C. to pellet the bacteria. The bacterial pellets were washed twice by centrifugation in TBS at 4° C. The final pellets were resuspended in TBS to an optical density of 42% Transmittance (T) at 562 nm in a volume of approximately 25 ml of TBS and used for challenge. Just prior to challenge, 1 ml of these bacterial suspensions was serially diluted and plated on agar to enumerate the number of colony-forming units (CFU) per mouse dose.

Example 5

Challenge

Fourteen days after the second vaccination, mice in all groups (1-7) were subcutaneously challenged in the back of the neck with 0.1 ml of the appropriate organism. The seven groups of mice were challenged as follows:

Group-1 (Placebo-Vaccinated): Challenged with ATCC 19636

Group-2 (Vaccinated with ATCC 19636 proteins expressed under iron-restriction): Challenged with ATCC 19636

Group-3 (Placebo-Vaccinated): Challenged with Bovine 1477

Group-4 (Vaccinated Bovine 1477 proteins expressed under iron-restriction): Challenged with Bovine 1477

Group-5 (Vaccinated Bovine 1477 proteins expressed under iron-restriction): Challenged with ATCC 19636

Group-6 (Vaccinated ATCC 19636 proteins expressed under iron-restriction): Challenged with Bovine 1477

Group-7 (Bovine 1477 FeCl$_3$-Vaccinated): Challenged with Bovine 1477

As determined by the enumeration protocol described in Example 4, the concentration of *S. aureus* 19636 used for challenge was 1.35×10$^8$ CFU per mouse dose, and the concentration of *S. aureus* 1477 used for challenge was 1.65×10' colony CFU per mouse dose. Morbidity, mortality and gross pathology were recorded daily for 7 days after challenge.

Figure 2:
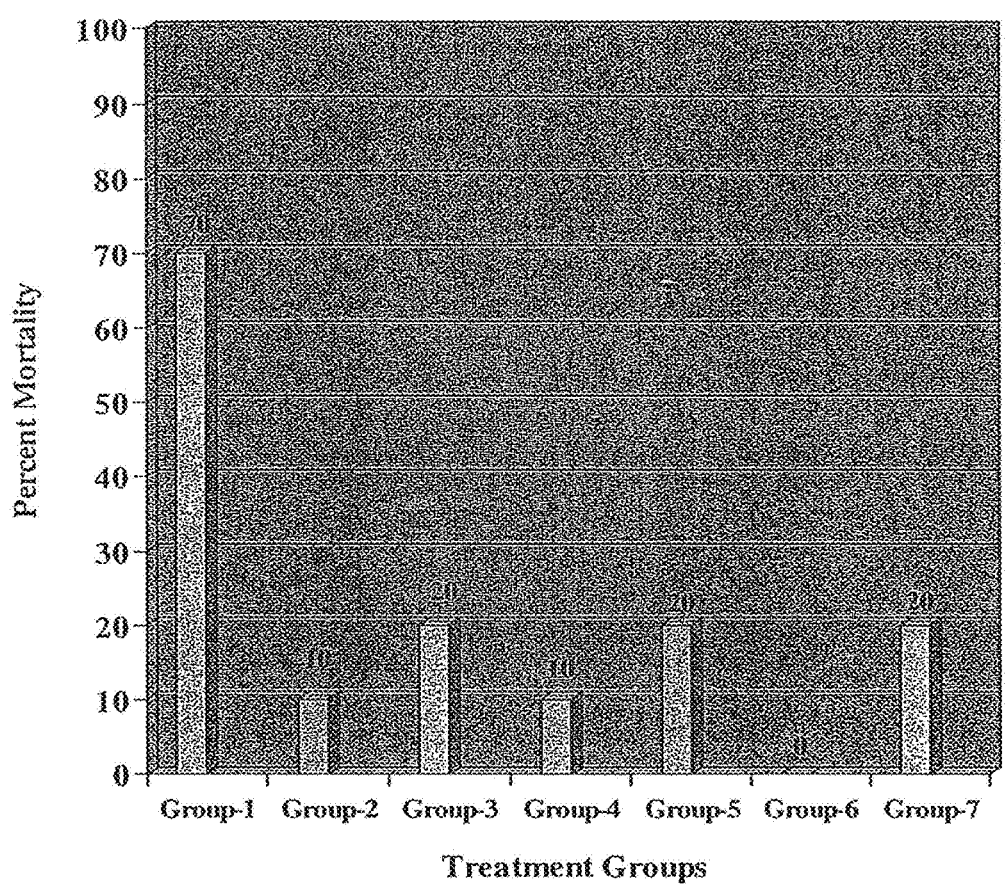
FIG. 2. The difference in mortality between vaccinated and non-vaccinated mice after homologous and heterologous challenge with Staphylococcus aureus.

When comparing the mice challenged with the ATCC 19636 isolate, 70% of the placebo-vaccinated Group 1 mice died within 7 days of challenge (Table 11 and FIG. 2). This demonstrated that strain 19636 caused a high rate of mortality in mice at the dose level administered. In contrast to the mice in Group 1, only 10% of the mice in Group 2 died within 7 days post-challenge. These results illustrated that the mice challenged with strain 19636 were significantly protected by vaccination with the 19636 composition (p=0.020, Fischer's Exact test). Furthermore, a Kaplan-Meier analysis of the time-to-death data indicated that the vaccine afforded significant (p=0.0042, logrank test) protection against homologous challenge (FIG. 3). In addition, only 20% of the mice in Group 5 died within 7 days of challenge, indicating that the bovine 1477 composition offered significant protection against challenge with the ATCC 19636 strain (p=0.015 logrank test for mortality). When the data was analyzed by a Kaplan-Meier survival curve and logrank test (FIG. 4), the protection against mortality was determined to be significant (p=0.015 logrank test for mortality), indicating that the vaccine composition derived from strain 1477 provided heterologous protection against challenge with strain 19636.

TABLE 11

Mortality of Vaccinated and Non-Vaccinated Mice Following Challenge with *Staphylococcus aureus* (human ATCC isolate 19636 and bovine isolate 1477).

| Groups | # Mice | # Dead | Percent mortality (%) |
|---|---|---|---|
| Group-1* (Placebo, ATCC 19636 Chlg) | 10 | 7/10 | 70 |
| Group-2* (ATCC 19636, Homologous Chlg) | 10 | 1/10 | 10 |
| Group-3* (Placebo, Bovine 1477 Chlg) | 10 | 2/10 | 20 |
| Group-4* (Bovine 1477, Homologous Chlg) | 10 | 1/10 | 10 |
| Group-5* (Bovine 1477, Heterologous Chlg) | 10 | 2/10 | 20 |
| Group-6* (ATCC 19636, Heterologous Chlg) | 10 | 0/10 | 0 |
| Group-7* (Bovine 1477 FeCl$_3$, Bovine 1477 Chlg) | 10 | 2/10 | 20 |

Group-1* (Placebo-Vaccinated/Challenged with ATCC 19636)
Group-2* (Vaccinated with ATCC 19636 proteins expressed under iron-restriction/Challenged with ATCC 19636)
Group-3* (Placebo-Vaccinated/Challenged with Bovine 1477)
Group-4* (Vaccinated with Bovine 1477 proteins expressed under iron-restriction/Challenged with Bovine 1477)
Group-5* (Vaccinated with Bovine 1477 proteins expressed under iron-restriction/Challenged with ATCC 19636)
Group-6* (Vaccinated with ATCC 19636 proteins expressed under iron-restriction/Challenged with Bovine 1477)
Group-7* (Bovine 1477 FeCl$_3$ -Vaccinated/Challenged with Bovine 1477)

When comparing the mice challenged with the bovine 1477 isolate, only 20% of the mice in the placebo-vaccinated group (Group 3) died within 7 days of challenge. However, challenge with the bovine 1477 isolate elicited the development of necrotic skin lesions on 6 (75%) of the surviving mice of Group 3. These lesions were measured and the average size of the lesions on the surviving mice was 18.5 mm (Table 12). In contrast, 20% of the Group 4 mice died within 7 days of challenge, but only three (38%) of the surviving mice developed lesions (average diameter, 2.7 mm). These results indicate that the bovine 1477 composition offered significant homologous protection against development of lesions in the mice challenged with the bovine strain 1477 (p=0.009, Student's t-test). In addition, vaccination with the ATCC 19636 composition protected against challenge with strain 1477, since no mice died in Group 6 and only three (30%) of the mice developed skin lesions (average diameter, 3.7 mm). Taken together, the reduced mortality and/or lesion development in the mice in Groups 5 and 6 demonstrate the significant cross-protective nature of the compositions derived from strains 19636 and 1477 (p=0.012, Student's t-test based on lesion size). In demonstration of the efficacy of the composition as compared to the non-iron regulated proteins, 20% of the mice in Group 7 died and 4 of the survivors developed skin lesions (average diameter, 15.8 mm). The mice of Group 7 demonstrated some degree of protection by vaccination with the proteins of the 1477 isolate since fewer mice developed lesions compared to the placebo-vaccinated Group 3. However, the skin lesions observed on the mice in group 7 were more frequent and of a larger diameter than the lesions on the mice of Group 4, indicating that, relative to proteins isolated from cells grown under iron-replete conditions, the proteins isolated from bacteria grown under iron restriction offered superior protection against an identical challenge.

TABLE 12

The Induction of Necrotic Lesions in Mice Seven Days Post-Challenge; with *Staphylococcus aureus* (ATCC Isolate 19636 and/or Bovine Isolate 1477)

| Group-1 | Group-2 | Group-3 | Group-4 | Group-5 | Group-6 | Group-7 |
|---|---|---|---|---|---|---|
| Lesion diameter (millimeter) per mouse | | | | | | |
| No lesion | No lesion | 26 | 5 | 5 | 5 | 25 |
| No lesion | No lesion | 25 | 2 | No lesion | 5 | 25 |
| No lesion | No lesion | 24 | 1 | No lesion | 1 | 10 |
| Dead | No lesion | 24 | No lesion | No lesion | No lesion | 3 |
| Dead | No lesion | 7 | No lesion | No lesion | No lesion | No lesion |
| Dead | No lesion | 5 | No lesion | No lesion | No lesion | No lesion |
| Dead | No lesion | No lesion | No lesion | No lesion | No lesion | No lesion |
| Dead | No lesion | No lesion | No lesion | No lesion | No lesion | No lesion |
| Dead | No lesion | Dead | No lesion | Dead | No lesion | Dead |
| Dead | Dead | Dead | Dead | Dead | No lesion | Dead |
| Average lesion diameter (nm) among surving mice | | | | | | |
| 0 | 0 | 18.5 | 2.7 | 5 | 3.7 | 15.8 |

Group-1, (Placebo-Vaccinated/Challenged ATCC, 19636)
Group-2 (Vaccinated with ATCC 19636 proteins expressed under iron-restriction/Challenged ATCC 19636)
Group-3 (Placebo-Vaccinated/Challenged Bovine 1477)
Group-4 (Vaccinated with Bovine 1477 proteins expressed under iron-restriction/Challenged Bovine 1477)
Group-5 (Vaccinated with Bovine 1477 proteins expressed under iron-restriction/Challenged ATCC 19636)
Group-6 (Vaccinated with ATCC 19636 proteins expressed under iron-restriction/Challenged Bovine 1477)
Group-7 (Bovine 1477 FeCl$_3$ Vaccinated/Challenged Bovine)

The cross-protective nature of the proteins observed in the mouse challenge study is supported by the similar molecular weights of the proteins from the *S. aureus* strains described in Example 1 (FIG. 1). Although there were noticeable differences in the SDS-PAGE profile of the proteins from the bovine-derived isolates, specifically the absence of a 38.4 kDa protein and the presence of 3 additional proteins, the proteins from both strains 1477 and ATCC 19636 elicited heterologous protection. These results indicate that the similar proteins between strains 19636 and 1477 are likely responsible for the cross-protection observed in Groups 5 and 6. By contrast, the protein profiles from strain 1477 grown under iron-deplete and iron-replete conditions are observably different. Those proteins isolated under iron-depleted conditions are more protective when compared to the proteins isolated under iron-replete conditions, demonstrated by the reduction in lesion development among the mice of Group 4 compared to the mice of Group 7.

Example 6

In mammals, it has been shown that the response to tissue injury or bacterial infection results in an acute inflammatory response. This response increases capillary permeability and phagocytic infiltration resulting in the clinical signs recognized as inflammation; swelling, fever, pain and redness; if left uncontrolled, this may lead to death. The activation of humoral factors and the release of cytokines mediate systemic events collectively known as the acute phase protein response which results in a cascade of physiological and biochemical events. The duration of this response is directly related to the severity of the injury and magnitude of the systemic infection. It has been well-documented that during bacterial sepsis, major surgery, burns and other bodily trauma there is an alteration in the concentration of a number of metal ions in serum such as, iron, copper, and zinc. For instance, during the acute phase of an infection there is a decrease in plasma levels of iron and zinc and an increase in copper. The alteration of these trace metal ions in serum may directly affect the severity or progression of any bacterial infection.

In this study we examined the expression of proteins of *Staphylcoccus aureus* under various conditions of metal ion restriction in order to mimic the expression of novel proteins that may be expressed during systemic invasion. The *Staphylococcus aureus* strains evaluated in this study originated from clinical samples of three different species of animal; avian (strain SAAV1), human (strain 19636), and bovine (strains 1477 and 2176). Briefly, cultures of each isolate were prepared from master seed stocks in 200 ml of Tryptic Soy Broth (TSB). Each culture was grown while stirring at 200 rpm for 6 hours at 37° C. Ten ml of each culture were transferred into 500 ml of deplete TSB containing one of four metal ion chelators; 2, 2-dipyridyl (Dp), 2-pyridylmethyl-ethylene diamine (TPEN), catechin, and naringenin (all obtained from Sigma, St. Louis, Mo.). In addition each culture was also grown in cation-replete media containing ferric chloride, zinc chloride and/or copper chloride prepared at 300 µM concentrations. The metal ion chelators were used at the following concentration; 22-dipyridyl (800 µM), catechin and naringenin were used at 300 µM, and 2-pyridylmethyl-ethylene diamine was used at a concentration of 100 µM. Cultures were grown with each chelator for 8 hours, at which point the culture was subcultured a second time for an additional 12 hours. Each culture was subcultured for three consecutive passes at 12-hour intervals. At the end of the third pass, each culture was harvested by centrifugation at 10,000×g for 20 minutes. Each culture was washed twice by centrifugation at 10,000×g and resuspended in 20 ml Tris-buffered saline, pH 7.2 at 4'C.

Each bacterial pellet was resuspended in 45 ml of Tris-buffered saline, pH 7.2 (25 mM Tris and 150 mM NaCl) and the resulting bacterial suspensions were dispensed as 9-ml aliquots into 5 individual tubes, twenty tubes total. One milliliter of TBS containing 50 units of lysostaphin (Sigma, St. Louis, Mo.) was added to each tube to give a final concentration of 5 units/mi. Following incubation at 37° C. for 30 minutes while shaking at 200 rpm, 1 ml of TBS containing 0.1 mg of lysozyme (Sigma) was added to each tube. The bacterial suspensions were then incubated for an additional 45 minutes while shaking at 200 rpm. Next, suspensions were centrifuged at 3050×g for 12 minutes at 4° C. to pellet large cellular debris. The supernatants were collected by aspiration without disturbing the pellet. The supernatant was then centrifuged at 39,000×g for 2.5 hours. The resulting pellets, enriched for metal-regulated membrane proteins, were resuspended in 200 μL Tris buffer, pH 7.2. The protein solutions for each isolate were combined for a total volume of 1 ml and stored at −90° C.

The proteins obtained from the SAAV1, 19636, 1477 and 2176 S. aureus isolates grown under iron, zinc and copper deplete conditions included metal-regulated polypeptides.

Cell extracts, derived from each isolate were size-fractionated on SDS-PAGE gels using a 4% stacking gel and 10% resolving gel. Samples for electrophoresis were prepared by combining 10 μl of sample with 30 μl of SDS reducing sample buffer (62.5 mM Tris-HCL ph 6.8, 20% glycerol, 2% SDS, 5% beta-mercaptoethanol) boiled for 4 minutes. Samples were electrophoresed at 18 mA of constant current for 5 hours at 4° C. using a Protein 11 xi cell power supply (BioRad Laboratories, Richmond, Calif., model 1000/500).

The SDS-PAGE patterns of the proteins grown under zinc and/or copper chelation showed unique banding patterns in all isolates that were different when compared to the same isolates grown under iron-restriction in the presence of 2,2'-dyipyridyl. For example, when the 19636 isolate was grown under iron-restriction or in the presence of the chelator 2,2'-dyipyridyl, unique iron-regulated proteins were expressed at the 87.73 kDa, 54.53 kDa, 38.42 kDa, 37.37 kDa, 35.70 kDa, 34.91 kDa and 33.0 kDa regions. These proteins were downregulated when the isolate was grown in the presence of ferric chloride. However, when the same isolate was grown in the presence of the zinc and or copper chelator, a novel subsets of proteins was expressed relative to the proteins expressed under iron-restriction; the new proteins having molecular weights of approximately 115 kDa, 88 kDa, 80 kDa, 71 kDa, 69 kDa, 35 kDa, 30 kDa, 29, kDa and 27 kDa. In addition, an 87.73 kDa protein was expressed under conditions of iron restriction or copper-restriction but not when cultures were zinc-restricted. The proteins expressed under iron-restriction appeared to be downregulated when growth was under either zinc-restriction and/or copper-restriction, but not completely shut off as seen when the isolate was grown in ferric chloride.

It appears that there are novel proteins expressed when the organism is grown under copper-restriction and/or zinc-restriction that are not expressed when the same isolate is grown under iron-restricted conditions. Since transitional metals are used by organisms to build enzymes that catalyze various biochemical reactions, the metal ions may play a vital role in microbial survival during a systemic infection. It is perhaps for this reason that during sepsis there is a transient decrease in the availability of these transitional metals, making them unavailable for growth of the organism. These novel proteins could very well enhance the protective efficacy of the existing composition grown under iron-restriction because they may also be expressed by the bacteria under the metal ion restriction experienced during systemic invasion.

Example 7

Compositions of the Present Invention can Also be Produced Under Large Scale Commercial Conditions Fermentation A cryogenic vial of the working seed (2 ml at $10^9$ CFU/ml) as described in Example 1 was used to inoculate 500 ml of Tryptic Soy Broth (TSB) without dextrose (Difco) pre-warmed to 37° C. containing 0.125 g/l 2,2-dipyridyl (Sigma), 2.7 grams BiTek yeast extract (Difco) and glycerol (3% vol/vol). The culture was incubated at 37° C. for 12 hours while stirring at 200 rpm at which time it was used to inoculate 2 liters of the above media and allowed to grow for an additional 4 hours at 37° C. This culture was used to inoculate a 20-liter Virtis bench-top fermentor, (Virtis, Gardiner, N.Y.) charged with 13 liters of the above-described media. The pH was held constant between 6.9 and 7.1 by automatic titration with 50% NaOH and 10% HCL. The stirring speed was adjusted at 400 rev/minute, and the culture aerated with 11 liters air/minute at 37° C. Foaming was controlled automatically by the addition of 11 ml defoamer (Mazu DF 204 Chem/Serv, Minneapolis, Minn.). The culture was allowed to grow continuously at these conditions for 4 hours at which time was sterilely pumped into a 150-liter fermentor (W. B. Moore, Easton, Pa.). The fermentor was charged with 120 liters tryptic soy broth without dextrose (3,600.0 grams), BiTek yeast extract (600 grams), glycerol (3,600 ml), 2,2-dypyrdyl (3.0 grams) and Mazu DF 204 defoamer (60 ml). The parameters of the fermentation were as follows: dissolved oxygen (DO) was maintained at 30%+/−10% by increasing agitation to 220 rev/minute sparged with 60 liters of air/minute and 10 pounds per square inch (psi) back pressure. The pH was held constant between 6.9 and 7.1 by automatic titration with 50% NaOH and 10% HCL and the temperature maintained at 37° C. At hour 4.5 ($OD_{500}$ 8-9) of the fermentation the culture was transferred to a 1,500 liter New Brunswick Scientific fermentor IF-15000 charged with 1200 liters tryptic soy broth without dextrose (36,000 grams), BiTek yeast extract (6,000 grams), glycerol (36,000 ml), 22-dypyrdyl (30.0 grams) and Mazu DF 204 defoamer (600 ml). The parameters of the fermentation were as follows: dissolved oxygen (DO) was maintained at 60%+/−10% with supplemental oxygen by increasing agitation to 300 rev/minute sparged with 300 to 1100 liters of air/minute and 5 pounds per square inch (psi) back pressure. As fermentation progressed supplemental oxygen was added from 0-90 liters/minute to assist in the control of dissolved oxygen. The pH was held constant between 6.9 and 7.4 by automatic titration with 50% NaOH and 10% HCL and the temperature was maintained at 37° C.

At approximately 5 hours post inoculation of the large fermentor the culture was supplemented with additional nutrients by feeding 70 liters of media containing 18,000 grams TSB without dextrose, 3.000 grams yeast extract 30.0 grams 2,2-dipyridyl and 18,000 ml of glycerol. The rate of feed was adjusted to approximately 28 liters/hour while increasing agitation. At the end of the feed the fermentation was allowed to continue for an additional 4 hours at which point the fermentation was terminated by lowing the temperature of the fermentor to 18° C. ($OD_{540}$ 35-40 at a 1:100 dilution).

Harvest

The bacterial fermentation was concentrated and washed using a Pall Filtron Tangential Flow Maxiset-25 (Pall Filtron Corporation, Northboro, Mass.) equipped with three 30 ft$^2$ Alpha 300-K open channel filters, catalog No. AS300C5, (Pall Filtron) connected to a Waukesha Model U-60 feed pump (Waukesha Cherry-Burrell, Delevan, Wis.) The original culture volume of 1250 liters was reduced to 50 liters (2.5 liters/minute) using a filter inlet pressure of 30 psi and a retentate pressure of 5-6 psi. The bacterial retentate was adjusted back up to 150 liters using Tris-buffered Saline pH 8.5 and then concentrated again to 50 liters to help remove any contaminating exogenous proteins, such as exoproteins to include secreted toxins and proteases. The elevated pH of the Iris-buffered saline helps prevent much of the proteolytic degradation that can occur during storage of the whole cell suspension. Protease inhibitors may be used instead of, or in addition to, an elevated pH. The retentate was mixed thoroughly while in the 200-liter tank using a bottom mount magnetically driven mixer. The retentate was sterilely dispensed (3.5 liters) into sterile 4 liter Nalgene containers No. 2122 and placed into a −20° C. freezer for storage as a breaking point in the manufacture, or could be further processed. The pellet mass was calculated by centrifuging 30 ml samples of the fermented culture and final harvest. Briefly, pre-weighted 50 ml Nalgene conical tubes were centrifuged at 39,000×g for 90 minutes in a Beckman J2-21 centrifuge using a JA-21 rotor (Beckman Instruments, Palo Alto Calif.). At the end of the run, the supernate was poured off and the tubes were weighed again. The pellet mass was calculated for each stage. The fermentation process yielded a wet pellet mass of approximately 60 kilograms.

Disruption

Eighty kilograms of bacterial cell slurry in Tris-buffered Saline pH 8.5 was aseptically transferred into a steam in place 1000 liter jacketed process tank (Lee, Model 259LU) with a top mounted mixer (Eastern, Model TME-1/2. EMI Incorporated, Clinton, Conn.) containing 900 liters TBS pH 8.5. The bulk bacterial suspension was chilled to 4° C. with continuous mixing for 18 hours at 200 rpm at which time was disrupted by homogenization. Briefly, the 1000 liter tank containing the bacterial suspension was connected to a model C-500-B Avestin Homogenizer, (Avestin Inc. Ottawa Canda). A second 1000 liter jacketed process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of the first pass, fluid was circulated at 70 psi via a Waukesha model 10DO pump (Waukesha) through the homogenizer (500 gallons/hour), while the homogenizer pressure was adjusted to 30,000 psi. Prior to the first pass, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The number of passes through the homogenizer was standardized to give a final percent transmittance between 78-91% T at a 1:100 dilution preferably between 86-91%. After homogenization, the tank was removed from the homogenizer and put onto a chiller loop at 4° C. and mixed at 240 rpm.

Protein Harvest

The disrupted bacterial suspension containing the iron-regulated proteins as illustrated in FIG. 1 were collected by centrifugation using T-1 Sharples, (Alfa Laval Seperations, Warminster, Pa.). Briefly, the 1000 liter jacketed process tank containing the disrupted bacterial homogenate was fed into 12 Sharpies with a feed rate of 250 ml/minute at 17 psi at a centrifugal force of 60,000×g. The effluent was collected into a second 1000 liter jacketed process tank through a closed sterile loop allowing for multiple passes through the centrifuges while maintaining a closed system. The temperature during centrifugation was kept at 4° C. The homogentae was passed 8 times across the centrifuges. Approximately 50% of the protein was collected after the second pass, at which point, the homogenate fluid was concentrated to ⅓ of its original volume, which shortened the process time for the next 6 passes. The homogenate tank was aseptically disconnected from the centrifuges and connected to a Millipore Pellicon Tangential Flow Filter assembly (Millipore Corporation, Bedford, Mass.), equipped with a 25 ft$^2$ screen-channel series Alpha 30K Centrasette filter (Pall Filtron) connected to a Waukesha Model U30 feed pump for concentration. After concentration, centrifugation was continued until the process was completed. Protein was collected after each pass. The protein was collected, resuspended and dispensed in 50 liters Tris-buffered saline pH 8.5 containing 0.15% formulin (Sigma) as preservative.

Diafiltration

The protein suspension was washed by diafiltration at 4° C. to remove any exogenous proteins (proteases, toxins, cytoplasmic and metabolic enzymes etc). Briefly, the 50 liters of protein was sterilely transferred into a 200 liter process tank containing 150 liters sterile Tris-buffer saline, pH 8.5 equipped with a bottom mount Dayton mixer, Model 2Z846 (Dayton Electric, Chicago, Ill.) rotating at 125 rev/minute. The process tank was sterilely connected to a Millipore Pellicon Tangential Flow Filter assembly (Millipore Corporation), equipped with a 25 ft$^2$ screen-channel series Alpha 30K Centrasette filter (Pall Filtron) connected to a Waukesha Model U30 feed pump. The 200 liter protein solution was concentrated by filtration to a target volume 50 liters at which point 150 liters of sterile saline was added. The protein suspension was then concentrated to approximately 50 liters. The protein concentrate was stored in a 50 liter jacketed process tank equipped with a top mounted mixer and stored at 4° C.

It is interesting to note that the composition derived from the large scale process using homogenization as a means of disruption generated identical banding profiles as examined by SDS-PAGE as compared to the smaller scale process described in Example 1. These results show that lysostaphin could be replaced as the bacterial lysis agent using the Avestin homogenizer C500-B. This discovery allows for the low cost generation of large volumes of iron-regulated proteins from staphlylococci.

Example 8

Hyper-Immunization of Mice and Preparation of Polyclonal Antibody

Passive immunization with purified antibody isolated from mice vaccinated with proteins derived from S. aureus strains 19636 grown under iron-limiting conditions was protective against a homologous and heterologous S. aureus challenge. Fifteen adult CD1 mice were vaccinated as described in Example 3 with the protein composition derived from S. aureus strain ATCC19636 grown under iron-deplete conditions as described in Examples 1 and 2. Mice were vaccinated intraperitoneally 3 times at 7 day intervals with 50 μg of protein composition at each vaccination. Seven days after the third immunization, mice were bled completely by cardiac puncture. Serum was pooled and antibody purified using standard ammonium sulfate precipitation. Exogenous serum proteins were removed first prior to antibody precipitation by adding 0.5 volumes of saturated ammonium sulfate pH 7.2. The solution was stirred at 100 rpm for 24 hours at 4° C. The solution was again centrifuged at 3000×g for 30 minutes. The supernatant was collected and precipitated again by adding enough saturated ammonium sulfate to bring the final concentration to 55% saturation. The solution was stirred at 100 rpm for 24 hours at 4° C. The precipitate was centrifuged at 3000×g for 30 minutes. The final pellet from each sample was resuspended into 2 ml PBS pH 7.2. The precipitated antibodies were then dialyzed using a 50,000 molecular cut off dialysis tubing (Pierce, Rockford Ill.) for 30 hours against three 1 liter changes of phosphate-buffered saline to remove ammonium sulfate. The first two liter changes were preserved with 0.02% sodium azide. The final 1 liter buffer change contained no preservative. The dialysate was collected and centrifuged again to remove any remaining debris at 3000×g for 30 minutes. The antibody solution was stored at 4° C. for less then 48 hours prior to use. Each sample was plated on blood agar to verify sterility prior to infusion.

Example 9

Passive Immunization and Challenge

In order to evaluate the protective effect of infused antibody raised against S. aureus proteins expressed during iron-limitation, two groups of 15 mice each were infused intraperitoneally with either the purified antibody preparation (Group 1) or physiological saline (Group 2) in a 200 μL infusion. An additional two groups of 15 mice each were infused subcutaneously with either the purified antibody preparation (Group 3) or physiological saline (Group 4). After 60 minutes, the 2 groups of 15 mice receiving an intraperitoneal infusion were challenged intraperitoneally with $1.3 \times 10^0$ cfu of S. aureus strain 19636. Similarly, the 2 groups of 15 mice receiving a subcutaneous infusion were challenged subcutaneously with $1.3 \times 10^8$ cfu of S. aureus strain 1477 to test for cross-protection against challenge by a different S. aureus strain. Mortality and/or lesion size was recorded for 5 days and the livers of all mice were removed post-mortem, homogenized and plated to determine the number of S. aureus present as a measure of systemic infection. The Kaplan-Meier survival curves (FIGS. 5 and 6) show the protective effect afforded by the infusion of antibodies from mice vaccinated with the S. aureus proteins expressed during iron restriction. Although the difference between the infused and control groups for the ATCC 19636-challenge groups was not significant ($p=0.076$, log-rank test), the liver of the single mouse that died within the antibody-infused group at Day 1 was cultured on blood agar to determine the absence and/or presence of the challenge organism (S. aureus). The culture derived from this mouse was negative for Staphylococcus and showed no growth on the blood agar plate or culture medium. In contrast, the livers of the mice that died within the placebo group, were all positive for the presence of Staphylococcus, in fact, pure cultures were obtained on each blood agar plate derived from the livers of these mice. While the liver data do not preclude the possibility that the mouse that died within the antibody-infused group died of S. aureus infection, the infection was not systemic, as it was in the placebo group, and the mouse may have died for other reasons. Censoring of this antibody-infused mouse death results in a significant difference between antibody-infused and placebo treatments ($p=0.015$, log-rank test). The data for the cross-challenge, where mice were infused with antibody generated after vaccination with ATCC 19636-derived proteins and challenged by S. aureus strain 1477, also showed a protective trend. Between 7 and 14 days post challenge, all mice in the infused and non-infused groups began to develop necrotic skin lesions. However, gross examination of mice clearly revealed a visible delay in the formation of an observable lesion as well as the severity of the lesion between the groups. Infused mice developed lesions more slowly as compared to non-infused control mice which developed lesion faster then infused mice and at a greater degree of severity. The infused mice healed faster then non-infused mice. This was clearly evident between 21 and 35 days post challenge. Gross examination of mice at 35 days post challenge showed that non-infused mice were severely disfigured and revealed a greater degree of scarring. In fact, many of these mice lost normal posture, in that they appeared twisted in appearance, in contrast to infused mice that did not develop nearly the extensive scar tissue and/or disfigurement as illustrated by the twisted appearance that the non-infused mice developed. Overall, these data suggest that interperitoneal infusion of antibodies raised against S. aureus iron-induced proteins can both protect against and limit the severity of S. aureus infection.

Example 10

Evaluation of a Vaccine Composition Derived from Staphylococcus aureus in a Chronically Infected Dairy Herd A commercial Dairy herd having a history of chronically high somatic cell counts attributable to Staphylococcus aureus was chosen for the evaluation of a vaccine composition as described in Example 1. The criterion for establishing vaccine efficacy of this experimental study was: 1) decreased incidence of clinical mastitis caused by Staphylococcus aureus among vaccinates compared to non-vaccinated controls, 2) improvement (i.e., a decrease) in somatic cell count among vaccinates compared to controls and 3) decrease in culture positive isolation rates of S. aureus between vaccinated and non-vaccinated controls. Blood will be taken at the time of the first vaccination (day 0) and again at 3 and 6 weeks post initial immunization. Injection site reactions or systemic reactions following vaccinations were monitored throughout the study. In addition, bulk tank milk samples were cultured and quantitatively enumerated to determine if there was a decrease in the number of CFU of Staphylococcus aureus cultured after vaccination.

Three of the Staphylococcus isolates derived from the chronically infected lactating cows within the herd were grown under conditions of iron-restriction and non-iron restricted conditions as described in Example 1. The three isolates were designated TTX101, TTX102, and TTX103. Extracted samples were examined by SDS-PAGE to compare banding profiles between isolates. Identical banding profiles were observed among isolates examined; the compositions made from each isolate included proteins having molecular weights of 87.73 kDa, 80.46 kDa, 65.08 kDa, 54.53 kDa, 37.37 kDa, 35.70 kDa, 34.91 kDa, 33.0 kDa and 31.83 kDa. These proteins are the same molecular weights as previously described in Table 10. In addition, when comparing the isolates identical banding profiles were seen with those proteins that were expressed in all conditions that were not regulated by iron: 150 kDa, 132 kDa, 120 kDa, 75 kDa, 58 kDa, 50 kDa, 44 kDa, 43 kDa, 41 kDa, and 40 kDa.

Example 11

Vaccine Preparation of *Staphylococcus aureus* (TTX101)

A composition was prepared as described in Example 1 using the isolate TTX101. The composition included proteins expressed under iron deplete conditions having molecular weights of 87.73 kDa, 80.46 kDa, 65.08 kDa, 54.53 kDa, 37.37 kDa, 35.70 kDa, 34.91 kDa, 33.0 kDa, and 31.83 kDa as well as non-metal regulated proteins having molecular weights of 150 kDa, 132 kDa, 120 kDa, 75 kDa, 58 kDa, 50 kDa, 44 kDa 43 kDa 41 kDa, and 40 kDa. The immunizing composition derived from strain TTX101 was used to prepare the experimental vaccine by emulsifying the extracted protein suspension (400 µg total protein per milliliter) into a commercial adjuvant (EMULSIGEN. MVP Laboratories, Ralston Nebr.) using an IKA Ultra Turrax T-50 homogenizing vessel (IKA, Cincinnati, Ohio) to give a final dose of 800 µg total protein in a 2.0 ml injectable volume with an adjuvant concentration of 22.5% vol/vol. The vaccine was administered subcutaneously 2 times at 21 day intervals.

Example 12

Experimental Design and Herd Vaccination

Eighteen days before the first vaccination all lactating cows enrolled in the study (N=80) were tested for *S. aureus* by standardized aerobic bacteriological culture methods by culturing individual milk samples derived from each lactating cow. In addition, the Somatic Cell Counts (SCC) were enumerated by the Dairy Herd Improvement Association using standard methods. Fourteen of the 80 cows were clinically diagnosed with mastitis and were culture positive for *S. aureus*. The remaining cows (N=66) tested negative for *S. aureus*. The eighty cows were equally divided into two groups designated as group 1, vaccinated (N=40) and group-2, non-vaccinated (N=40). The fourteen clinically diagnosed *Staphylococcus* positive cows were equally distributed between both groups so that each study group contained 7 cows with clinical mastitis. The average SCC between groups prior to the first vaccination was 203,219 in the non-vaccinated controls compared to 240,443 in vaccinates (not statistically different p=0.7).

Eighteen days after the first sampling all cows in group 1 were vaccinated subcutaneously in the upper right shoulder with 2 ml of vaccine as described in Example 11. Ten days after the first vaccination milk samples were taken at this time period by the DHIA for the enumeration of somatic cells from each individual cow. Milk samples were not bacteriologically tested at this time period for determining the presence of *Staphylococcus*. The difference in the SCC between groups at this time period was 125,241 (vaccinates) compared to 196,297 (controls). This was a 36% difference in the number of somatic cells between vaccinates as compared to non-vaccinated controls. The difference in the SCC between the controls and vaccinates at this sampling period was not statistically different (p=0.5). The lack of statistical difference in the SCC between groups at both sampling periods was due to the large variation in individual SCC between cows. The injection site of each vaccinated cow was also examined at this same time period. None of the cows examined showed any adverse tissue reaction at the site of injection by physical examination. In addition, there was no measurable loss in milk production due to vaccination.

Twenty one days after the first vaccination all cows in group-1 (vaccinates) were given their second vaccination or booster. During the time period between first and second vaccination, cows in both groups (vaccinates and controls) developed teat damage due to a dramatic drop in the environmental temperature resulting in the formation of lesions at the end of the teat, resulting in the development of infected teats and potentially increasing the isolation of *Staphylococcus* during sampling, which was observed at the third sampling period. Twenty three days after the second vaccination milk samples were taken by the DHIA for the enumeration of Somatic Cells from each individual cow. Milk samples were also bacteriologically tested for the presence of *Staphylococcus aureus*. There was a dramatic increase in isolation rate of *S. aureus* at this time period in the cows that tested negative at the first sampling period. In the non-vaccinated controls 42.9% of these cows now tested positive for *S. aureus*, in contrast to the vaccinates, which only showed and increase of 35.5%. This was a 7.4% difference between vaccinates as compared to the non vaccinated controls. It's difficult to say that the improvement in the isolation rate of *S. aureus* in the vaccinated group was due to the effect of the vaccine alone. One cannot overlook the difficulty in obtaining clean milk samples from cows that had teat damage which could increase the potential contamination of the milk by *S. aureus* when obtaining the sample. Nevertheless, there was a significant difference in the average SCC between vaccinates compared to controls. The average SCC of the vaccinated group was 222,679 compared to 404,278 somatic cells as measured in the control group. This was a 44.9% difference between vaccinates when compared to the non vaccinated controls. It's interesting to speculate that the difference seen in the SCC between these groups also coincides with the difference in the isolation rate of *S. aureus* between groups. However, due to the large variation in SCC between individual animals and the small sample size of the experimental trial in the number of animals the difference was not statistically different (p=0.28).

At this same time period the injection site of each vaccinated cow was examined for any adverse tissue reaction that may have been caused by the vaccine composition. None of the cows examined showed any adverse reaction at the site of injection by physical examination. The vaccine compositions appeared to be highly tissue compatible and caused no measurable loss in milk production after each vaccination.

Monitoring of the cows is continued by measuring SCC and milk samples for the presence or absence of *Staphylococcus aureus*. Some of the cows of each group are vaccinated a third time at 42 days after the second vaccination. There appears to be a difference favoring the use of the vaccine composition for decreasing somatic cell counts and controlling infection caused by *Staphylococcus aureus*. Further monitoring includes serology based on antibody titers to the vaccine composition, changes in milk production in vaccinated cows due the improvement in health, and decreased SCC of vaccinated animals compared to non-vaccinated cohorts. In addition, other experiments are conducted to investigate the protective index of the vaccine based on dose response following challenge with a virulent *S. aureus*.

Example 13

Since the molecular weights of the proteins among the different *S. aureus* strains have been demonstrated to be similar and since heterologous protection was observed in the mouse challenge study, we sought to determine if the proteins sharing similar molecular weights in FIG. 1 were similar proteins. The technique chosen to characterize the proteins was matrix-assisted laser desorption/ionization mass spectrometry (MALDI-MS). A portion of the composition was resolved using SDS-PAGE as described in Example 1, and the gel was stained with Coomassie Brilliant blue to visualize the proteins.

Materials and Methods

Excision and Washing.

The gel was washed for 10 minutes with water twice. Each protein band of interest was excised by cutting as close to the protein band as possible to reduce the amount of gel present in the sample.

Each gel slice was cut into 1×1 mm cubes and placed in 1.5 ml tube. The gel pieces were washed with water for 15 minutes. All the solvent volumes used in the wash steps were approximately equal to twice the volume of the gel slice. The gel slice was next washed with water/acetonitrile (1:1) for 15 minutes. When the proteins had been stained with silver, the water/acetonitrile mixture was removed, the gel pieces dried in a SpeedVac (ThermoSavant, Holbrook, N.Y.) and then reduced and alkylated as described below. When the gel pieces were not silver-stained, the water/acetonitrile mixture was removed, and acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for 15 minutes, the liquid removed, and the gel pieces dried in a SpeedVac.

Reduction & Alkylation.

The dried gel pieces were rehydrated in 10 mM DTT and 100 mM $NH_4HCO_3$ and incubated for 45 minutes at 56° C. After allowing the tubes to cool to room temperature, the liquid was removed and the same volume of a mixture of 55 mM iodoacetamide and 100 mM $NH_4HCO_3$ was immediately added. This was incubated for 30 minutes at room temperature in the dark. The liquid was removed, acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for 15 minutes, the liquid removed, and the gel pieces dried in a Speed vac. If the gel was stained with coomasie blue, and residual coomassie still remained, the wash with 100 mM $NH_4HCO_3$/acetonitrile was repeated.

In-Gel Digestion.

Gel pieces were completely dried down in a Speed Vac. The pieces were rehydrated in digestion buffer (50 mM $NH_4HCO_3$, 5 mM $CaCl_2$, 12.5 nanograms per microliter (ng/µl) trypsin) at 4° C. Enough buffer was added to cover the gel pieces, and more was added as needed. The gel pieces were incubated on ice for 45 minutes, and the supernatant removed and replaced with 5-2 µl of same buffer without trypsin. This was incubated at 37° C. overnight in an air incubator.

Extraction of Peptides.

A sufficient volume of 25 mM $NH_4HCO_3$ was added to cover gel pieces, and incubated for 15 minutes (typically in a bath sonicator). The same volume of acetonitrile was added and incubated for 15 minutes (in a bath sonicator if possible), and the supernatant was recovered. The extraction was repeated twice, using 5% formic acid instead of $NH_4HCO_3$. A sufficient volume of 5% formic acid was added to cover gel pieces, and incubated for 15 minutes (typically in a bath sonicator). The same volume of acetonitrile was added and incubated for 15 minutes (typically in a bath sonicator), and the supernatant was recovered. The extracts were pooled, and 10 mM DTT was added to a final concentration of 1 mM DTT. The sample was dried in a SpeedVac to a final volume of approximately 5 µl.

Desalting of Peptides.

The samples were desalted using a ZIPTIP pipette tips (C18, Millipore. Billerica, Mass.) as suggested by the manufacturer. Briefly, a sample was reconstituted in reconstitution solution (5:95 acetonitrile:$H_2O$, 0.1%-0.5% trifluoroacetic acid), centrifuged, and the pH checked to verify that it was less than 3. A ZIPTIP was hydrated by aspirating 10 µl of solution 1 (50:50 acetonitrile:$H_2O$, 0.1% trifluoroacetic acid) and discarding the aspirated aliquots. This was followed by aspirating 10 µl of solution 2 (0.1% trifluoroacetic acid in deionized $H_2O$) and discarding the aspirated aliquots. The sample was loaded into the tip by aspirating 10 µl of the sample slowly into the tip, expelling it into the sample tube, and repeating this 5 to 6 times. Ten microliters of solution 2 was aspirated into the tip, the solution discarded by expelling, and this process was repeated 5-7 times to wash. The peptides were eluted by aspirating 2.5 µl of ice cold solution 3 (60:40, acetonitrile:$H_2O$, 0.1% trofluoroacetic acid), expelling, and then re-aspirating the same aliquot in and out of the tip 3 times. After the solution has been expelled from the tip, the tube is capped and stored on ice.

Mass Spectrometric Peptide Mapping.

The peptides were suspended in 10 µl to 30 µl of 5% formic acid, and analyzed by MALDI-TOF MS (Bruker Daltonics Inc., Billerica, Mass.). The mass spectrum of the peptide fragments was determined as suggested by the manufacturer. Briefly, a sample containing the peptides resulting from a tryptic digest were mixed with matrix cyano-4-hydroxycinnamic acid, transferred to a target, and allowed to dry. The dried sample was placed in the mass spectrometer, irradiated, and the time of flight of each ion detected and used to determine a peptide mass fingerprint for each protein present in the composition. Known polypeptides were used to standardize the machine.

Data Analysis.

The experimentally observed masses for the peptides in each mass spectrum were compared to the expected masses of proteins using the Peptide Mass Fingerprint search method of the Mascot search engine (Matrix Science Ltd., London, UK, and www.matrixscience.com, see Perkins et al., Electrophoresis 20, 3551-3567 (1999)). The search parameters included: database, MSDB or NCBInr, taxonomy, bacteria (eubacteria) or Firmicutes (gram-positive bacteria); type of search, peptide mass fingerprint; enzyme, trypsin; fixed modifications, carbamidomethyl (C) or none; variable modifications, oxidation (M), carbamidomethyl (C), the combination, or none; mass values, monoisotopic; protein mass, unrestricted; peptide mass tolerance, between ±150 ppm and ±430 ppm, or t 1 Da; peptide charge state, Mr; max missed cleavages, 0 or 1; number of queries, 20.

Results

The result of this search was a mass fingerprint for each protein present in the composition is shown in Tables 2, 3, 4, and 5.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:

whole cells that express at least five polypeptides, each polypeptide having a molecular weight of 88 kDa, 55 kDa, 38 kDa, 37 kDa, 36 kDa, 35 kDa, or 33 kDa as determined by sodium dodecyl sulfate-polyacrylamide gel electrophoresis;

wherein the polypeptide having a molecular weight of 88 kDa comprises an amino acid sequence having at least 95% identity to the amino acid sequence of a reference polypeptide, wherein the reference polypeptide has a molecular weight of 88 kDa as determined by sodium dodecyl sulfate-polyacrylamide gel electrophoresis, comprises the amino acid sequences depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, and SEQ ID NO:33, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 55 kDa comprises an amino acid sequence having at least 95% identity to the amino acid sequence of a reference polypeptide, wherein the reference polypeptide has a molecular weight of 55 kDa as determined by sodium dodecyl sulfate-polyacrylamide gel electrophoresis, comprises the amino acid sequences depicted in SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:49, SEQ ID NO:51, SEQ ID NO:52, SEQ ID NO:53, SEQ ID NO:54, SEQ ID NO:57, SEQ ID NO:58, and SEQ ID NO:59, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 38 kDa comprises an amino acid sequence having at least 95% identity to the amino acid sequence of a reference polypeptide, wherein the reference polypeptide has a molecular weight of 38 kDa as determined by sodium dodecyl sulfate-polyacrylamide gel electrophoresis, comprises the amino acid sequences depicted in SEQ ID NO:64, SEQ ID NO:65, SEQ ID NO:66, SEQ ID NO:68, SEQ ID NO:69, SEQ ID NO:70, SEQ ID NO:72, SEQ ID NO:75, SEQ ID NO:76, and SEQ ID NO:77, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 37 kDa comprises an amino acid sequence having at least 95% identity to the amino acid sequence of a reference polypeptide, wherein the reference polypeptide has a molecular weight of 37 kDa as determined by sodium dodecyl sulfate-polyacrylamide gel electrophoresis, comprises the amino acid sequences depicted in SEQ ID NO:80, SEQ ID NO:82, SEQ ID NO:84, SEQ ID NO:85, SEQ ID NO:86, SEQ ID NO:87, SEQ ID NO:89, SEQ ID NO:90, SEQ ID NO:91, SEQ ID NO:94, SEQ ID NO:95, SEQ ID NO:96, SEQ ID NO:97, SEQ ID NO:99, SEQ ID NO:100, and SEQ ID NO:101, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 36 kDa comprises an amino acid sequence having at least 95% identity to the amino acid sequence of a reference polypeptide, wherein the reference polypeptide has a molecular weight of 36 kDa as determined by sodium dodecyl sulfate-polyacrylamide gel electrophoresis, comprises the amino acid sequences depicted in SEQ ID NO:103, SEQ ID NO:104, SEQ ID NO:105, SEQ ID NO:106, SEQ ID NO:107, SEQ ID NO:108, SEQ ID NO:109, and SEQ ID NO:110, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 35 kDa comprises an amino acid sequence having at least 95% identity to the amino acid sequence of a reference polypeptide, wherein the reference polypeptide has a molecular weight of 35 kDa as determined by sodium dodecyl sulfate-polyacrylamide gel electrophoresis, comprises the amino acid sequences depicted in SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, and SEQ ID NO:124, and is expressed by *Staphylococcus aureus* ATCC strain 19636 at a greater level when grown in medium comprising 1600 µM 2,2-dipyridyl compared to when grown in the medium without the 2,2-dipyridyl; and wherein the polypeptide having a molecular weight of 33 kDa comprises an amino acid sequence having at least 95% identity to the amino acid sequence of a reference polypeptide, wherein the reference polypeptide has a molecular weight of 33 kDa as determined by sodium dodecyl sulfate-polyacrylamide gel electrophoresis, comprises the amino acid sequences depicted in SEQ ID NO:126, SEQ ID NO:127, SEQ ID NO:128, SEQ ID NO:129, SEQ ID NO:130, SEQ ID NO:131, SEQ ID NO:132, SEQ ID NO:134, SEQ ID NO:135, SEQ ID NO:136, SEQ ID NO:137, SEQ ID NO:138, SEQ ID NO:140, SEQ ID NO:142, and SEQ ID NO:143, and is expressed by *Staphylococcus aureus* ATCC strain 19636 at a greater level when grown in medium comprising 1600 µM 2,2-dipyridyl compared to when grown in the medium without the 2,2-dipyridyl; and an adjuvant.

2. The composition of claim 1 further comprising a pharmaceutically acceptable carrier.

3. The composition of claim 1 wherein the whole cell is a *Staphylococcus aureus* cell.

4. The composition of claim 1 wherein the whole cell comprises a recombinant host cell genetically modified to express the polypeptides.

5. The composition of claim 1 wherein the whole cell expresses the 88 kDa polypeptide, the 55 kDa polypeptide, the 38 kDa polypeptide, the 37 kDa polypeptide, the 36 kDa polypeptide, the 35 kDa polypeptide, and the 33 kDa polypeptide.

6. The composition of claim 5 further comprising a pharmaceutically acceptable carrier.

7. The composition of claim 5 wherein the whole cell is a *Staphylococcus aureus* cell.

8. The composition of claim 5 wherein the whole cell comprises a recombinant host cell genetically modified to express the polypeptides.

9. A method for treating an infection in a subject, the method comprising administering an effective amount of a composition to a subject having or at risk of an infection caused by a *Staphylococcus* spp., the composition comprising:

whole cells that express at least five polypeptides, each polypeptide having a molecular weight of 88 kDa, 55 kDa, 38 kDa, 37 kDa, 36 kDa, 35 kDa, or 33 kDa as determined by sodium dodecyl sulfate-polyacrylamide gel electrophoresis;

wherein the polypeptide having a molecular weight of 88 kDa comprises an amino acid sequence having at least 95% identity to the amino acid sequence of a reference polypeptide, wherein the reference polypeptide has a molecular weight of 88 kDa as determined by sodium dodecyl sulfate-polyacrylamide gel electrophoresis, comprises the amino acid sequences depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, and SEQ ID NO:33, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 55 kDa comprises an amino acid sequence having at least 95% identity to the amino acid sequence of a reference polypeptide, wherein the reference polypeptide has a molecular weight of 55 kDa as determined by sodium dodecyl sulfate-polyacrylamide gel electrophoresis, comprises the amino acid sequences depicted in SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:49, SEQ ID NO:51, SEQ ID NO:52, SEQ ID NO:53, SEQ ID NO:54, SEQ ID NO:57, SEQ ID NO:58, and SEQ ID NO:59, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 38 kDa comprises an amino acid sequence having at least 95% identity to the amino acid sequence of a reference polypeptide, wherein the reference polypeptide has a molecular weight of 38 kDa as determined by sodium dodecyl sulfate-polyacrylamide gel electrophoresis, comprises the amino acid sequences depicted in SEQ ID NO:64, SEQ ID NO:65, SEQ ID NO:66, SEQ ID NO:68, SEQ ID NO:69, SEQ ID NO:70, SEQ ID NO:72, SEQ ID NO:75, SEQ ID NO:76, and SEQ ID NO:77, and is expressed by *Staphylococcus aureus* ATCC strain 19636 at a greater level when grown in medium comprising 1600 μM 2,2-dipyridyl compared to when grown in the medium without the 2,2-dipyridyl;

wherein the polypeptide having a molecular weight of 37 kDa comprises an amino acid sequence having at least 95% identity to the amino acid sequence of a reference polypeptide, wherein the reference polypeptide has a molecular weight of 37 kDa as determined by sodium dodecyl sulfate-polyacrylamide gel electrophoresis, comprises the amino acid sequences depicted in SEQ ID NO:80, SEQ ID NO:82, SEQ ID NO:84, SEQ ID NO:85, SEQ ID NO:86, SEQ ID NO:87, SEQ ID NO:89, SEQ ID NO:90, SEQ ID NO:91, SEQ ID NO:94, SEQ ID NO:95, SEQ ID NO:96, SEQ ID NO:97, SEQ ID NO:99, SEQ ID NO:100, and SEQ ID NO:101, and is expressed by *Staphylococcus aureus* ATCC strain 19636 at a greater level when grown in medium comprising 1600 μM 2,2-dipyridyl compared to when grown in the medium without the 2,2-dipyridyl;

wherein the polypeptide having a molecular weight of 36 kDa comprises an amino acid sequence having at least 95% identity to the amino acid sequence of a reference polypeptide, wherein the reference polypeptide has a molecular weight of 36 kDa as determined by sodium dodecyl sulfate-polyacrylamide gel electrophoresis, comprises the amino acid sequences depicted in SEQ ID NO:103, SEQ ID NO:104, SEQ ID NO:105, SEQ ID NO:106, SEQ ID NO:107, SEQ ID NO:108, SEQ ID NO:109, and SEQ ID NO:110, and is expressed by *Staphylococcus aureus* ATCC strain 19636 at a greater level when grown in medium comprising 1600 μM 2,2-dipyridyl compared to when grown in the medium without the 2,2-dipyridyl;

wherein the polypeptide having a molecular weight of 35 kDa comprises an amino acid sequence having at least 95% identity to the amino acid sequence of a reference polypeptide, wherein the reference polypeptide has a molecular weight of 35 kDa as determined by sodium dodecyl sulfate-polyacrylamide gel electrophoresis, comprises the amino acid sequences depicted in SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, and SEQ ID NO:124, and is expressed by *Staphylococcus aureus* ATCC strain 19636 at a greater level when grown in medium comprising 1600 μM 2,2-dipyridyl compared to when grown in the medium without the 2,2-dipyridyl; and wherein the polypeptide having a molecular weight of 33 kDa comprises an amino acid sequence having at least 95% identity to the amino acid sequence of a reference polypeptide, wherein the reference polypeptide has a molecular weight of 33 kDa as determined by sodium dodecyl sulfate-polyacrylamide gel electrophoresis, comprises the amino acid sequences depicted in SEQ ID NO:126, SEQ ID NO:127, SEQ ID NO:128, SEQ ID NO:129, SEQ ID NO:130, SEQ ID NO:131, SEQ ID NO:132, SEQ ID NO:134, SEQ ID NO:135, SEQ ID NO:136, SEQ ID NO:137, SEQ ID NO:138, SEQ ID NO:140, SEQ ID NO:142, and SEQ ID NO:143, and is expressed by *Staphylococcus aureus* ATCC strain 19636 at a greater level when grown in medium comprising 1600 μM 2,2-dipyridyl compared to when grown in the medium without the 2,2-dipyridyl; and an adjuvant.

10. The method of claim 9 wherein the subject is a mammal.

11. The method of claim 10 wherein the mammal is a human.

12. The method of claim 10 wherein the mammal is bovine, ovine, porcine, caprine, cervine, bisontine, or equine.

13. The method of claim 9 wherein the subject is avian.

14. The method of claim 9 wherein the subject is a companion animal.

15. The method of claim 9 wherein the composition is administered prophylactically.

16. The method of claim 9 wherein the *Staphylococcus* spp. is *S. aureus*.

17. The method of claim 9 wherein the whole cell expresses the 88 kDa polypeptide, the 55 kDa polypeptide, the 38 kDa polypeptide, the 37 kDa polypeptide, the 36 kDa polypeptide, the 35 kDa polypeptide, and the 33 kDa polypeptide.

18. A method of treating a symptom in a subject, the method comprising administering an effective amount of a composition to a subject having or at risk of an infection caused by a *Staphylococcus* spp., the composition comprising:

whole cells that express at least five polypeptides, each polypeptide having a molecular weight of 88 kDa, 55 kDa, 38 kDa, 37 kDa, 36 kDa, 35 kDa, or 33 kDa as determined by sodium dodecyl sulfate-polyacrylamide gel electrophoresis;

wherein the polypeptide having a molecular weight of 88 kDa comprises an amino acid sequence having at least 95% identity to the amino acid sequence of a reference polypeptide, wherein the reference polypeptide has a molecular weight of 88 kDa as determined by sodium dodecyl sulfate-polyacrylamide gel electrophoresis, comprises the amino acid sequences depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, and SEQ ID NO:33, and is expressed by *Staphylococcus aureus* ATCC strain 19636 at a greater level when grown in medium comprising 1600 μM 2,2-dipyridyl compared to when grown in the medium without the 2,2-dipyridyl;

wherein the polypeptide having a molecular weight of 55 kDa comprises an amino acid sequence having at least 95% identity to the amino acid sequence of a reference polypeptide, wherein the reference polypeptide has a molecular weight of 55 kDa as determined by sodium dodecyl sulfate-polyacrylamide gel electrophoresis, comprises the amino acid sequences depicted in SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:49, SEQ ID NO:51, SEQ ID NO:52, SEQ ID NO:53, SEQ ID NO:54, SEQ ID NO:57, SEQ ID NO:58, and SEQ ID NO:59, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 38 kDa comprises an amino acid sequence having at least 95% identity to the amino acid sequence of a reference polypeptide, wherein the reference polypeptide has a molecular weight of 38 kDa as determined by sodium dodecyl sulfate-polyacrylamide gel electrophoresis, comprises the amino acid sequences depicted in SEQ ID NO:64, SEQ ID NO:65, SEQ ID NO:66, SEQ ID NO:68, SEQ ID NO:69, SEQ ID NO:70, SEQ ID NO:72, SEQ ID NO:75, SEQ ID NO:76, and SEQ ID NO:77, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 37 kDa comprises an amino acid sequence having at least 95% identity to the amino acid sequence of a reference polypeptide, wherein the reference polypeptide has a molecular weight of 37 kDa as determined by sodium dodecyl sulfate-polyacrylamide gel electrophoresis, comprises the amino acid sequences depicted in SEQ ID NO:80, SEQ ID NO:82, SEQ ID NO:84, SEQ ID NO:85, SEQ ID NO:86, SEQ ID NO:87, SEQ ID NO:89, SEQ ID NO:90, SEQ ID NO:91, SEQ ID NO:94, SEQ ID NO:95, SEQ ID NO:96, SEQ ID NO:97, SEQ ID NO:99, SEQ ID NO:100, and SEQ ID NO:101, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 36 kDa comprises an amino acid sequence having at least 95% identity to the amino acid sequence of a reference polypeptide, wherein the reference polypeptide has a molecular weight of 36 kDa as determined by sodium dodecyl sulfate-polyacrylamide gel electrophoresis, comprises the amino acid sequences depicted in SEQ ID NO:103, SEQ ID NO:104, SEQ ID NO:105, SEQ ID NO:106, SEQ ID NO:107, SEQ ID NO:108, SEQ ID NO:109, and SEQ ID NO:110, and is expressed by *Staphylococcus aureus* ATCC strain 19636 at a greater level when grown in medium comprising 1600 µM 2,2-dipyridyl compared to when grown in the medium without the 2,2-dipyridyl;

wherein the polypeptide having a molecular weight of 35 kDa comprises an amino acid sequence having at least 95% identity to the amino acid sequence of a reference polypeptide, wherein the reference polypeptide has a molecular weight of 35 kDa as determined by sodium dodecyl sulfate-polyacrylamide gel electrophoresis, comprises the amino acid sequences depicted in SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, and SEQ ID NO:124, and is expressed by *Staphylococcus aureus* ATCC strain 19636 at a greater level when grown in medium comprising 1600 µM 2,2-dipyridyl compared to when grown in the medium without the 2,2-dipyridyl; and wherein the polypeptide having a molecular weight of 33 kDa comprises an amino acid sequence having at least 95% identity to the amino acid sequence of a reference polypeptide, wherein the reference polypeptide has a molecular weight of 33 kDa as determined by sodium dodecyl sulfate-polyacrylamide gel electrophoresis, comprises the amino acid sequences depicted in SEQ ID NO:126, SEQ ID NO:127, SEQ ID NO:128, SEQ ID NO:129, SEQ ID NO:130, SEQ ID NO:131, SEQ ID NO:132, SEQ ID NO:134, SEQ ID NO:135, SEQ ID NO:136, SEQ ID NO:137, SEQ ID NO:138, SEQ ID NO:140, SEQ ID NO:142, and SEQ ID NO:143, and is expressed by *Staphylococcus aureus* ATCC strain 19636 at a greater level when grown in medium comprising 1600 µM 2,2-dipyridyl compared to when grown in the medium without the 2,2-dipyridyl; and an adjuvant.

19. The method of claim 18 wherein the subject is a mammal.

20. The method of claim 19 wherein the mammal is a human.

21. The method of claim 19 wherein the mammal is bovine, ovine, porcine, caprine, cervine, bisontine, or equine.

22. The method of claim 18 wherein the subject is avian.

23. The method of claim 18 wherein the subject is a companion animal.

24. The method of claim 18 wherein the composition is administered prophylactically.

25. The method of claim 18 wherein the *Staphylococcus* spp. is *S. aureus*.

26. The method of claim 18 wherein the whole cell expresses the 88 kDa polypeptide, the 55 kDa polypeptide, the 38 kDa polypeptide, the 37 kDa polypeptide, the 36 kDa polypeptide, the 35 kDa polypeptide, and the 33 kDa polypeptide.

* * * * *

```
                        SEQUENCE LISTING

<160> NUMBER OF SEQ ID NOS: 417

<210> SEQ ID NO 1
<211> LENGTH: 5
<212> TYPE: PRT
<213> ORGANISM: Staphylococcus aureus

<400> SEQUENCE: 1

His Val Asp Val Arg
1               5

<210> SEQ ID NO 2
<211> LENGTH: 5
<212> TYPE: PRT
<213> ORGANISM: Staphylococcus aureus

<400> SEQUENCE: 2

Tyr Ser Tyr Glu Arg
1               5

<210> SEQ ID NO 3
<211> LENGTH: 7
<212> TYPE: PRT
<213> ORGANISM: Staphylococcus aureus

<400> SEQUENCE: 3

Ile Ile Gly Asp Tyr Arg Arg
1               5

<210> SEQ ID NO 4
<211> LENGTH: 7
<212> TYPE: PRT
<213> ORGANISM: Staphylococcus aureus

<400> SEQUENCE: 4

Ile Phe Thr Asp Tyr Arg Lys
1               5

<210> SEQ ID NO 5
<211> LENGTH: 8
<212> TYPE: PRT
<213> ORGANISM: Staphylococcus aureus

<400> SEQUENCE: 5

Glu Leu Lys Glu Leu Gly Gln Lys
1               5
```

```
<210> SEQ ID NO 6
<211> LENGTH: 8
<212> TYPE: PRT
<213> ORGANISM: Staphylococcus aureus

<400> SEQUENCE: 6

Tyr Ala Gln Val Lys Pro Ile Arg
1               5

<210> SEQ ID NO 7
<211> LENGTH: 8
<212> TYPE: PRT
<213> ORGANISM: Staphylococcus aureus

<400> SEQUENCE: 7

Gln Met Gln Phe Phe Gly Ala Arg
1               5

<210> SEQ ID NO 8
<211> LENGTH: 9
<212> TYPE: PRT
<213> ORGANISM: Staphylococcus aureus

<400> SEQUENCE: 8

Ser Met Gln Pro Phe Gly Gly Ile Arg
1               5

<210> SEQ ID NO 9
<211> LENGTH: 10
<212> TYPE: PRT
<213> ORGANISM: Staphylococcus aureus

<400> SEQUENCE: 9

Val Ser Gly Tyr Ala Val Asn Phe Ile Lys
1               5                   10

<210> SEQ ID NO 10
<211> LENGTH: 10
<212> TYPE: PRT
<213> ORGANISM: Staphylococcus aureus

<400> SEQUENCE: 10

Asn His Ala Thr Ala Trp Gln Gly Phe Lys
1               5                   10

<210> SEQ ID NO 11
<211> LENGTH: 10
<212> TYPE: PRT
<213> ORGANISM: Staphylococcus aureus

<400> SEQUENCE: 11

Leu Trp Glu Gln Val Met Gln Leu Ser Lys
1               5                   10

<210> SEQ ID NO 12
<211> LENGTH: 11
<212> TYPE: PRT
<213> ORGANISM: Staphylococcus aureus

<400> SEQUENCE: 12

Ser Leu Gly Lys Glu Pro Glu Asp Gln Asn Arg
1               5                   10

<210> SEQ ID NO 13
```

```
<211> LENGTH: 12
<212> TYPE: PRT
<213> ORGANISM: Staphylococcus aureus

<400> SEQUENCE: 13

Asp Gly Ile Ser Asn Thr Phe Ser Ile Val Pro Lys
1               5                   10

<210> SEQ ID NO 14
<211> LENGTH: 13
<212> TYPE: PRT
<213> ORGANISM: Staphylococcus aureus

<400> SEQUENCE: 14

Ala Gly Val Ile Thr Gly Leu Pro Asp Ala Tyr Gly Arg
1               5                   10

<210> SEQ ID NO 15
<211> LENGTH: 11
<212> TYPE: PRT
<213> ORGANISM: Staphylococcus aureus

<400> SEQUENCE: 15

Thr Ser Thr Phe Leu Asp Ile Tyr Ala Glu Arg
1               5                   10

<210> SEQ ID NO 16
<211> LENGTH: 12
<212> TYPE: PRT
<213> ORGANISM: Staphylococcus aureus

<400> SEQUENCE: 16

Ser Met Gln Pro Phe Gly Gly Ile Arg Met Ala Lys
1               5                   10

<210> SEQ ID NO 17
<211> LENGTH: 12
<212> TYPE: PRT
<213> ORGANISM: Staphylococcus aureus

<400> SEQUENCE: 17

Thr His Asn Gln Gly Val Phe Asp Ala Tyr Ser Arg
1               5                   10

<210> SEQ ID NO 18
<211> LENGTH: 14
<212> TYPE: PRT
<213> ORGANISM: Staphylococcus aureus

<400> SEQUENCE: 18

Lys Ala Gly Val Ile Thr Gly Leu Pro Asp Ala Tyr Gly Arg
1               5                   10

<210> SEQ ID NO 19
<211> LENGTH: 13
<212> TYPE: PRT
<213> ORGANISM: Staphylococcus aureus

<400> SEQUENCE: 19

Thr Leu Leu Tyr Ala Ile Asn Gly Gly Lys Asp Glu Lys
1               5                   10

<210> SEQ ID NO 20
<211> LENGTH: 12
<212> TYPE: PRT
```

<213> ORGANISM: Staphylococcus aureus

<400> SEQUENCE: 20

Ile Glu Met Ala Leu His Asp Thr Glu Ile Val Arg
1               5                   10

<210> SEQ ID NO 21
<211> LENGTH: 15
<212> TYPE: PRT
<213> ORGANISM: Staphylococcus aureus

<400> SEQUENCE: 21

Ala Gly Glu Pro Phe Ala Pro Gly Ala Asn Pro Met His Gly Arg
1               5                   10                  15

<210> SEQ ID NO 22
<211> LENGTH: 13
<212> TYPE: PRT
<213> ORGANISM: Staphylococcus aureus

<400> SEQUENCE: 22

Val Ala Leu Tyr Gly Val Asp Phe Leu Met Glu Glu Lys
1               5                   10

<210> SEQ ID NO 23
<211> LENGTH: 13
<212> TYPE: PRT
<213> ORGANISM: Staphylococcus aureus

<400> SEQUENCE: 23

Lys Thr His Asn Gln Gly Val Phe Asp Ala Tyr Ser Arg
1               5                   10

<210> SEQ ID NO 24
<211> LENGTH: 13
<212> TYPE: PRT
<213> ORGANISM: Staphylococcus aureus

<400> SEQUENCE: 24

Tyr Gly Phe Asp Leu Ser Arg Pro Ala Glu Asn Phe Lys
1               5                   10

<210> SEQ ID NO 25
<211> LENGTH: 13
<212> TYPE: PRT
<213> ORGANISM: Staphylococcus aureus

<400> SEQUENCE: 25

Thr Ser Ser Ile Gln Tyr Glu Asn Asp Asp Ile Met Arg
1               5                   10

<210> SEQ ID NO 26
<211> LENGTH: 16
<212> TYPE: PRT
<213> ORGANISM: Staphylococcus aureus

<400> SEQUENCE: 26

Lys Ala Gly Glu Pro Phe Ala Pro Gly Ala Asn Pro Met His Gly Arg
1               5                   10                  15

<210> SEQ ID NO 27
<211> LENGTH: 14
<212> TYPE: PRT
<213> ORGANISM: Staphylococcus aureus

```
<400> SEQUENCE: 27

Arg Val Ala Leu Tyr Gly Val Asp Phe Leu Met Glu Glu Lys
1               5                   10

<210> SEQ ID NO 28
<211> LENGTH: 13
<212> TYPE: PRT
<213> ORGANISM: Staphylococcus aureus

<400> SEQUENCE: 28

Leu Trp Glu Gln Val Met Gln Leu Ser Lys Glu Glu Arg
1               5                   10

<210> SEQ ID NO 29
<211> LENGTH: 16
<212> TYPE: PRT
<213> ORGANISM: Staphylococcus aureus

<400> SEQUENCE: 29

Met Leu Glu Thr Asn Lys Asn His Ala Thr Ala Trp Gln Gly Phe Lys
1               5                   10                  15

<210> SEQ ID NO 30
<211> LENGTH: 17
<212> TYPE: PRT
<213> ORGANISM: Staphylococcus aureus

<400> SEQUENCE: 30

Met His Asp Phe Asn Thr Met Ser Thr Glu Met Ser Glu Asp Val Ile
1               5                   10                  15

Arg

<210> SEQ ID NO 31
<211> LENGTH: 18
<212> TYPE: PRT
<213> ORGANISM: Staphylococcus aureus

<400> SEQUENCE: 31

Tyr Gly Asn Asn Asp Asp Arg Val Asp Asp Ile Ala Val Asp Leu Val
1               5                   10                  15

Glu Arg

<210> SEQ ID NO 32
<211> LENGTH: 19
<212> TYPE: PRT
<213> ORGANISM: Staphylococcus aureus

<400> SEQUENCE: 32

Glu Thr Leu Ile Asp Ala Met Glu His Pro Glu Glu Tyr Pro Gln Leu
1               5                   10                  15

Thr Ile Arg

<210> SEQ ID NO 33
<211> LENGTH: 25
<212> TYPE: PRT
<213> ORGANISM: Staphylococcus aureus

<400> SEQUENCE: 33

Tyr Ala Gln Val Lys Pro Ile Arg Asn Glu Glu Gly Leu Val Val Asp
1               5                   10                  15

Phe Glu Ile Glu Gly Asp Phe Pro Lys
                20                  25
```

<210> SEQ ID NO 34
<211> LENGTH: 6
<212> TYPE: PRT
<213> ORGANISM: Staphylococcus aureus

<400> SEQUENCE: 34

Leu His Ser Trp Leu Lys
1               5

<210> SEQ ID NO 35
<211> LENGTH: 7
<212> TYPE: PRT
<213> ORGANISM: Staphylococcus aureus

<400> SEQUENCE: 35

Lys Leu His Ser Trp Leu Lys
1               5

<210> SEQ ID NO 36
<211> LENGTH: 7
<212> TYPE: PRT
<213> ORGANISM: Staphylococcus aureus

<400> SEQUENCE: 36

Thr Tyr Thr Phe His Leu Arg
1               5

<210> SEQ ID NO 37
<211> LENGTH: 9
<212> TYPE: PRT
<213> ORGANISM: Staphylococcus aureus

<400> SEQUENCE: 37

Lys Phe Asp Gly Thr Gly Pro Phe Lys
1               5

<210> SEQ ID NO 38
<211> LENGTH: 9
<212> TYPE: PRT
<213> ORGANISM: Staphylococcus aureus

<400> SEQUENCE: 38

Gln Ala Ile Gly His Met Val Asn Arg
1               5

<210> SEQ ID NO 39
<211> LENGTH: 9
<212> TYPE: PRT
<213> ORGANISM: Staphylococcus aureus

<400> SEQUENCE: 39

Lys Trp Asp Val Ser Glu Asp Gly Lys
1               5

<210> SEQ ID NO 40
<211> LENGTH: 10
<212> TYPE: PRT
<213> ORGANISM: Staphylococcus aureus

<400> SEQUENCE: 40

Ile Tyr Asn Ser Ile Asp Asp Ala Phe Lys
1               5                   10

<210> SEQ ID NO 41
<211> LENGTH: 10
<212> TYPE: PRT
<213> ORGANISM: Staphylococcus aureus

<400> SEQUENCE: 41

Asn Leu Glu Met Ala Met Tyr Tyr Asp Lys
1               5                   10

<210> SEQ ID NO 42
<211> LENGTH: 11
<212> TYPE: PRT
<213> ORGANISM: Staphylococcus aureus

<400> SEQUENCE: 42

Glu Asn Lys Gln Leu Thr Tyr Thr Thr Val Lys
1               5                   10

<210> SEQ ID NO 43
<211> LENGTH: 12
<212> TYPE: PRT
<213> ORGANISM: Staphylococcus aureus

<400> SEQUENCE: 43

Ala Glu Ser Leu Leu Asp Glu Ala Gly Trp Lys Lys
1               5                   10

<210> SEQ ID NO 44
<211> LENGTH: 12
<212> TYPE: PRT
<213> ORGANISM: Staphylococcus aureus

<400> SEQUENCE: 44

Thr Val Arg Gln Ala Ile Gly His Met Val Asn Arg
1               5                   10

<210> SEQ ID NO 45
<211> LENGTH: 11
<212> TYPE: PRT
<213> ORGANISM: Staphylococcus aureus

<400> SEQUENCE: 45

Thr Tyr Thr Phe His Leu Arg Asp Asp Val Lys
1               5                   10

<210> SEQ ID NO 46
<211> LENGTH: 12
<212> TYPE: PRT
<213> ORGANISM: Staphylococcus aureus

<400> SEQUENCE: 46

Lys Gly Glu Thr Asn Phe Ala Phe Thr Asp Asp Arg
1               5                   10

<210> SEQ ID NO 47
<211> LENGTH: 13
<212> TYPE: PRT
<213> ORGANISM: Staphylococcus aureus

<400> SEQUENCE: 47

Phe His Asp Gly Thr Pro Phe Asp Ala Asp Ala Val Lys
1               5                   10

<210> SEQ ID NO 48
<211> LENGTH: 12

```
<212> TYPE: PRT
<213> ORGANISM: Staphylococcus aureus

<400> SEQUENCE: 48

Asn Val Thr Asp Ile Asn Phe Asp Met Pro Thr Arg
1               5                   10

<210> SEQ ID NO 49
<211> LENGTH: 12
<212> TYPE: PRT
<213> ORGANISM: Staphylococcus aureus

<400> SEQUENCE: 49

Asp Lys Ile Tyr Asn Ser Ile Asp Asp Ala Phe Lys
1               5                   10

<210> SEQ ID NO 50
<211> LENGTH: 12
<212> TYPE: PRT
<213> ORGANISM: Staphylococcus aureus

<400> SEQUENCE: 50

Glu Gln Ala Glu Tyr Leu Gln Ala Glu Phe Lys Lys
1               5                   10

<210> SEQ ID NO 51
<211> LENGTH: 14
<212> TYPE: PRT
<213> ORGANISM: Staphylococcus aureus

<400> SEQUENCE: 51

Val Met Pro Ala Gly Glu Thr Ala Phe Leu Ser Met Lys Lys
1               5                   10

<210> SEQ ID NO 52
<211> LENGTH: 14
<212> TYPE: PRT
<213> ORGANISM: Staphylococcus aureus

<400> SEQUENCE: 52

Phe His Asp Gly Thr Pro Phe Asp Ala Asp Ala Val Lys Lys
1               5                   10

<210> SEQ ID NO 53
<211> LENGTH: 13
<212> TYPE: PRT
<213> ORGANISM: Staphylococcus aureus

<400> SEQUENCE: 53

Asn Val Thr Asp Ile Asn Phe Asp Met Pro Thr Arg Lys
1               5                   10

<210> SEQ ID NO 54
<211> LENGTH: 14
<212> TYPE: PRT
<213> ORGANISM: Staphylococcus aureus

<400> SEQUENCE: 54

Leu Asn Ile Asn Gly Glu Thr Ser Asp Lys Ile Ala Glu Arg
1               5                   10

<210> SEQ ID NO 55
<211> LENGTH: 16
<212> TYPE: PRT
<213> ORGANISM: Staphylococcus aureus
```

-continued

<400> SEQUENCE: 55

Glu Ile Leu Asp Gly Gln Glu Lys Pro Ala Thr Gln Leu Phe Ala Lys
1               5                   10                  15

<210> SEQ ID NO 56
<211> LENGTH: 17
<212> TYPE: PRT
<213> ORGANISM: Staphylococcus aureus

<400> SEQUENCE: 56

Gly Ser Ser Ser Gln Lys Glu Gln Ala Glu Tyr Leu Gln Ala Glu Phe
1               5                   10                  15

Lys

<210> SEQ ID NO 57
<211> LENGTH: 16
<212> TYPE: PRT
<213> ORGANISM: Staphylococcus aureus

<400> SEQUENCE: 57

Asp Glu Ser Ala Asp Phe Asn Lys Asn Asp Gln Tyr Trp Gly Glu Lys
1               5                   10                  15

<210> SEQ ID NO 58
<211> LENGTH: 19
<212> TYPE: PRT
<213> ORGANISM: Staphylococcus aureus

<400> SEQUENCE: 58

Ile Ala Lys Glu Ile Leu Asp Gly Gln Glu Lys Pro Ala Thr Gln Leu
1               5                   10                  15

Phe Ala Lys

<210> SEQ ID NO 59
<211> LENGTH: 18
<212> TYPE: PRT
<213> ORGANISM: Staphylococcus aureus

<400> SEQUENCE: 59

Val Ser Phe Thr Gln Ser Gln Tyr Glu Leu Pro Phe Asn Glu Met Gln
1               5                   10                  15

Tyr Lys

<210> SEQ ID NO 60
<211> LENGTH: 22
<212> TYPE: PRT
<213> ORGANISM: Staphylococcus aureus
<220> FEATURE:
<221> NAME/KEY: MOD_RES
<222> LOCATION: (12)..(12)
<223> OTHER INFORMATION: Oxidized Met

<400> SEQUENCE: 60

Glu Ala Tyr Gln Pro Ala Leu Ala Glu Leu Ala Met Pro Arg Pro Tyr
1               5                   10                  15

Val Phe Val Ser Pro Lys
                20

<210> SEQ ID NO 61
<211> LENGTH: 26
<212> TYPE: PRT
<213> ORGANISM: Staphylococcus aureus
<220> FEATURE:
<221> NAME/KEY: MISC_FEATURE
<223> OTHER INFORMATION: Any two fo the three Mets in this sequence are
      oxidized
<220> FEATURE:
<221> NAME/KEY: MOD_RES
<222> LOCATION: (5)..(5)
<223> OTHER INFORMATION: This residue may or may not be oxidized
<220> FEATURE:
<221> NAME/KEY: MOD_RES
<222> LOCATION: (14)..(14)
<223> OTHER INFORMATION: This residue may or may not be oxidized
<220> FEATURE:
<221> NAME/KEY: MOD_RES
<222> LOCATION: (19)..(19)
<223> OTHER INFORMATION: This residue may or may not be oxidized

<400> SEQUENCE: 61

Asp Ile Gly Asp Met Asn Pro His Val Tyr Gly Gly Ser Met Ser Ala
1               5                   10                  15

Glu Ser Met Ile Tyr Glu Pro Leu Val Arg
            20                  25

<210> SEQ ID NO 62
<211> LENGTH: 26
<212> TYPE: PRT
<213> ORGANISM: Staphylococcus aureus
<220> FEATURE:
<221> NAME/KEY: MOD_RES
<222> LOCATION: (5)..(5)
<223> OTHER INFORMATION: Oxidized Met
<220> FEATURE:
<221> NAME/KEY: MOD_RES
<222> LOCATION: (14)..(14)
<223> OTHER INFORMATION: Oxidized Met
<220> FEATURE:
<221> NAME/KEY: MOD_RES
<222> LOCATION: (19)..(19)
<223> OTHER INFORMATION: Oxidized Met

<400> SEQUENCE: 62

Asp Ile Gly Asp Met Asn Pro His Val Tyr Gly Gly Ser Met Ser Ala
1               5                   10                  15

Glu Ser Met Ile Tyr Glu Pro Leu Val Arg
            20                  25

<210> SEQ ID NO 63
<211> LENGTH: 9
<212> TYPE: PRT
<213> ORGANISM: Staphylococcus aureus

<400> SEQUENCE: 63

Ile Val Tyr Val Gly Ala Asp Glu Lys
1               5

<210> SEQ ID NO 64
<211> LENGTH: 9
<212> TYPE: PRT
<213> ORGANISM: Staphylococcus aureus

<400> SEQUENCE: 64

Gln Ala Leu Asn Asn Pro Val Leu Lys
1               5

<210> SEQ ID NO 65
<211> LENGTH: 10
<212> TYPE: PRT
<213> ORGANISM: Staphylococcus aureus

```
<400> SEQUENCE: 65

Glu Thr Val Lys Ile Glu Asn Asn Tyr Lys
1               5                  10

<210> SEQ ID NO 66
<211> LENGTH: 11
<212> TYPE: PRT
<213> ORGANISM: Staphylococcus aureus

<400> SEQUENCE: 66

Glu Asn Pro Asp Val Ile Leu Ala Met Asp Arg
1               5                  10

<210> SEQ ID NO 67
<211> LENGTH: 14
<212> TYPE: PRT
<213> ORGANISM: Staphylococcus aureus

<400> SEQUENCE: 67

Ile Ala Ala Thr Lys Pro Glu Val Ile Phe Ile Ser Gly Arg
1               5                  10

<210> SEQ ID NO 68
<211> LENGTH: 14
<212> TYPE: PRT
<213> ORGANISM: Staphylococcus aureus

<400> SEQUENCE: 68

Asn Ala Val Val Leu Asp Tyr Gly Ala Leu Asp Val Met Lys
1               5                  10

<210> SEQ ID NO 69
<211> LENGTH: 13
<212> TYPE: PRT
<213> ORGANISM: Staphylococcus aureus

<400> SEQUENCE: 69

Ala Leu Pro Asn Phe Leu Glu Ser Phe Lys Asp Asp Lys
1               5                  10

<210> SEQ ID NO 70
<211> LENGTH: 14
<212> TYPE: PRT
<213> ORGANISM: Staphylococcus aureus

<400> SEQUENCE: 70

Leu Trp Tyr Phe Ala Ala Gly Ser Thr Thr Thr Thr Ile Lys
1               5                  10

<210> SEQ ID NO 71
<211> LENGTH: 16
<212> TYPE: PRT
<213> ORGANISM: Staphylococcus aureus

<400> SEQUENCE: 71

Phe Gly Gly Leu Val Tyr Asp Thr Leu Gly Phe Asn Ala Val Asp Lys
1               5                  10                  15

<210> SEQ ID NO 72
<211> LENGTH: 16
<212> TYPE: PRT
<213> ORGANISM: Staphylococcus aureus

<400> SEQUENCE: 72
```

Ile Val Tyr Val Gly Ala Asp Glu Lys Asn Leu Ile Gly Ser Met Lys
1               5                   10                  15

<210> SEQ ID NO 73
<211> LENGTH: 17
<212> TYPE: PRT
<213> ORGANISM: Staphylococcus aureus

<400> SEQUENCE: 73

Phe Gly Gly Leu Val Tyr Asp Thr Leu Gly Phe Asn Ala Val Asp Lys
1               5                   10                  15
Lys

<210> SEQ ID NO 74
<211> LENGTH: 18
<212> TYPE: PRT
<213> ORGANISM: Staphylococcus aureus

<400> SEQUENCE: 74

Gly Arg Phe Gly Gly Leu Val Tyr Asp Thr Leu Gly Phe Asn Ala Val
1               5                   10                  15
Asp Lys

<210> SEQ ID NO 75
<211> LENGTH: 18
<212> TYPE: PRT
<213> ORGANISM: Staphylococcus aureus

<400> SEQUENCE: 75

Thr Val Met Tyr Leu Leu Val Asn Glu Gly Leu Ser Thr Phe Gly
1               5                   10                  15
Pro Lys

<210> SEQ ID NO 76
<211> LENGTH: 20
<212> TYPE: PRT
<213> ORGANISM: Staphylococcus aureus

<400> SEQUENCE: 76

Glu Val Asn Phe Asp Lys Ile Ala Ala Thr Lys Pro Glu Val Ile Phe
1               5                   10                  15
Ile Ser Gly Arg
            20

<210> SEQ ID NO 77
<211> LENGTH: 28
<212> TYPE: PRT
<213> ORGANISM: Staphylococcus aureus

<400> SEQUENCE: 77

Val Ser Asn Ser Asn His Gly Gln Asn Val Ser Asn Glu Tyr Val Asn
1               5                   10                  15
Lys Glu Asn Pro Asp Val Ile Leu Ala Met Asp Arg
            20                  25

<210> SEQ ID NO 78
<211> LENGTH: 5
<212> TYPE: PRT
<213> ORGANISM: Staphylococcus aureus

<400> SEQUENCE: 78

Phe Glu Tyr Ile Lys

```
1               5
```

<210> SEQ ID NO 79
<211> LENGTH: 6
<212> TYPE: PRT
<213> ORGANISM: Staphylococcus aureus

<400> SEQUENCE: 79

```
Asp Ala Trp Pro Leu Lys
1               5
```

<210> SEQ ID NO 80
<211> LENGTH: 7
<212> TYPE: PRT
<213> ORGANISM: Staphylococcus aureus

<400> SEQUENCE: 80

```
Ala Ser Val Val Asn Phe Arg
1               5
```

<210> SEQ ID NO 81
<211> LENGTH: 7
<212> TYPE: PRT
<213> ORGANISM: Staphylococcus aureus

<400> SEQUENCE: 81

```
Val Tyr Asp Gln Leu Ser Lys
1               5
```

<210> SEQ ID NO 82
<211> LENGTH: 9
<212> TYPE: PRT
<213> ORGANISM: Staphylococcus aureus

<400> SEQUENCE: 82

```
His Ala Met Gly Thr Thr Glu Ile Lys
1               5
```

<210> SEQ ID NO 83
<211> LENGTH: 8
<212> TYPE: PRT
<213> ORGANISM: Staphylococcus aureus

<400> SEQUENCE: 83

```
Leu Ile Asp Asp Leu Tyr Glu Lys
1               5
```

<210> SEQ ID NO 84
<211> LENGTH: 8
<212> TYPE: PRT
<213> ORGANISM: Staphylococcus aureus

<400> SEQUENCE: 84

```
Tyr Lys Asp Ala Trp Pro Leu Lys
1               5
```

<210> SEQ ID NO 85
<211> LENGTH: 9
<212> TYPE: PRT
<213> ORGANISM: Staphylococcus aureus

<400> SEQUENCE: 85

```
Glu Lys Glu Ala Glu Asp Leu Leu Lys
1               5
```

<210> SEQ ID NO 86
<211> LENGTH: 10
<212> TYPE: PRT
<213> ORGANISM: Staphylococcus aureus

<400> SEQUENCE: 86

Leu Lys Pro Asp Leu Ile Val Ala Ser Lys
1               5                   10

<210> SEQ ID NO 87
<211> LENGTH: 9
<212> TYPE: PRT
<213> ORGANISM: Staphylococcus aureus

<400> SEQUENCE: 87

Phe Glu Tyr Ile Lys Asn Asp Leu Lys
1               5

<210> SEQ ID NO 88
<211> LENGTH: 10
<212> TYPE: PRT
<213> ORGANISM: Staphylococcus aureus

<400> SEQUENCE: 88

Lys Thr Glu Ser Glu Trp Thr Ser Ser Lys
1               5                   10

<210> SEQ ID NO 89
<211> LENGTH: 10
<212> TYPE: PRT
<213> ORGANISM: Staphylococcus aureus

<400> SEQUENCE: 89

Tyr Asp Asp Lys Val Ala Ala Phe Gln Lys
1               5                   10

<210> SEQ ID NO 90
<211> LENGTH: 10
<212> TYPE: PRT
<213> ORGANISM: Staphylococcus aureus

<400> SEQUENCE: 90

Asn Glu Lys Val Tyr Asp Gln Leu Ser Lys
1               5                   10

<210> SEQ ID NO 91
<211> LENGTH: 12
<212> TYPE: PRT
<213> ORGANISM: Staphylococcus aureus

<400> SEQUENCE: 91

Ile Ala Pro Thr Val Ser Thr Asp Thr Val Phe Lys
1               5                   10

<210> SEQ ID NO 92
<211> LENGTH: 12
<212> TYPE: PRT
<213> ORGANISM: Staphylococcus aureus

<400> SEQUENCE: 92

Thr Glu Ser Glu Trp Thr Ser Ser Lys Glu Trp Lys
1               5                   10

<210> SEQ ID NO 93

```
<211> LENGTH: 13
<212> TYPE: PRT
<213> ORGANISM: Staphylococcus aureus

<400> SEQUENCE: 93

Asp Ala Trp Pro Leu Lys Ala Ser Val Val Asn Phe Arg
1               5                   10

<210> SEQ ID NO 94
<211> LENGTH: 14
<212> TYPE: PRT
<213> ORGANISM: Staphylococcus aureus

<400> SEQUENCE: 94

Gln Val Asp Asn Gly Lys Asp Ile Ile Gln Leu Thr Ser Lys
1               5                   10

<210> SEQ ID NO 95
<211> LENGTH: 13
<212> TYPE: PRT
<213> ORGANISM: Staphylococcus aureus

<400> SEQUENCE: 95

Leu Ile Asp Asp Leu Tyr Glu Lys Leu Asn Ile Glu Lys
1               5                   10

<210> SEQ ID NO 96
<211> LENGTH: 15
<212> TYPE: PRT
<213> ORGANISM: Staphylococcus aureus

<400> SEQUENCE: 96

Ile Val Gly Gln Glu Pro Ala Pro Asn Leu Glu Glu Ile Ser Lys
1               5                   10                  15

<210> SEQ ID NO 97
<211> LENGTH: 15
<212> TYPE: PRT
<213> ORGANISM: Staphylococcus aureus

<400> SEQUENCE: 97

Glu Ser Ile Pro Leu Met Asn Ala Asp His Ile Phe Val Val Lys
1               5                   10                  15

<210> SEQ ID NO 98
<211> LENGTH: 17
<212> TYPE: PRT
<213> ORGANISM: Staphylococcus aureus

<400> SEQUENCE: 98

Ile Tyr Ala Gly Gly Tyr Ala Gly Glu Ile Leu Asn Asp Leu Gly Phe
1               5                   10                  15

Lys

<210> SEQ ID NO 99
<211> LENGTH: 18
<212> TYPE: PRT
<213> ORGANISM: Staphylococcus aureus

<400> SEQUENCE: 99

Ile Tyr Ala Gly Gly Tyr Ala Gly Glu Ile Leu Asn Asp Leu Gly Phe
1               5                   10                  15

Lys Arg
```

<210> SEQ ID NO 100
<211> LENGTH: 20
<212> TYPE: PRT
<213> ORGANISM: Staphylococcus aureus

<400> SEQUENCE: 100

Asn Asn Gln Val Ser Asp Asp Leu Asp Glu Ile Thr Trp Asn Leu Ala
1               5                   10                  15

Gly Gly Tyr Lys
            20

<210> SEQ ID NO 101
<211> LENGTH: 32
<212> TYPE: PRT
<213> ORGANISM: Staphylococcus aureus

<400> SEQUENCE: 101

Arg Val Val Thr Leu Tyr Gln Gly Ala Thr Asp Val Ala Val Ser Leu
1               5                   10                  15

Gly Val Lys Pro Val Gly Ala Val Glu Ser Trp Thr Gln Lys Pro Lys
            20                  25                  30

<210> SEQ ID NO 102
<211> LENGTH: 5
<212> TYPE: PRT
<213> ORGANISM: Staphylococcus aureus

<400> SEQUENCE: 102

Asp Val Trp Ala Arg
1               5

<210> SEQ ID NO 103
<211> LENGTH: 6
<212> TYPE: PRT
<213> ORGANISM: Staphylococcus aureus

<400> SEQUENCE: 103

Ile Ile Lys Pro Val Arg
1               5

<210> SEQ ID NO 104
<211> LENGTH: 10
<212> TYPE: PRT
<213> ORGANISM: Staphylococcus aureus

<400> SEQUENCE: 104

Ile Gly Asp Tyr Thr Ser Val Gly Thr Arg
1               5                   10

<210> SEQ ID NO 105
<211> LENGTH: 10
<212> TYPE: PRT
<213> ORGANISM: Staphylococcus aureus

<400> SEQUENCE: 105

Lys Gln Pro Asn Leu Glu Glu Ile Ser Lys
1               5                   10

<210> SEQ ID NO 106
<211> LENGTH: 12
<212> TYPE: PRT
<213> ORGANISM: Staphylococcus aureus

<400> SEQUENCE: 106

```
Leu Lys Pro Asp Leu Ile Ile Ala Asp Ser Ser Arg
1               5                   10

<210> SEQ ID NO 107
<211> LENGTH: 11
<212> TYPE: PRT
<213> ORGANISM: Staphylococcus aureus

<400> SEQUENCE: 107

Val Asp Ile Val Asp Arg Asp Val Trp Ala Arg
1               5                   10

<210> SEQ ID NO 108
<211> LENGTH: 18
<212> TYPE: PRT
<213> ORGANISM: Staphylococcus aureus

<400> SEQUENCE: 108

Gly Pro Tyr Leu Gln Leu Asp Thr Glu His Leu Ala Asp Leu Asn Pro
1               5                   10                  15

Glu Arg

<210> SEQ ID NO 109
<211> LENGTH: 22
<212> TYPE: PRT
<213> ORGANISM: Staphylococcus aureus

<400> SEQUENCE: 109

Ala Gly Leu Leu Ala His Pro Asn Tyr Ser Tyr Val Gly Gln Phe Leu
1               5                   10                  15

Asn Glu Leu Gly Phe Lys
            20

<210> SEQ ID NO 110
<211> LENGTH: 27
<212> TYPE: PRT
<213> ORGANISM: Staphylococcus aureus

<400> SEQUENCE: 110

Ile Val Val Leu Glu Tyr Ser Phe Ala Asp Ala Leu Ala Ala Leu Asp
1               5                   10                  15

Val Lys Pro Val Gly Ile Ala Asp Asp Gly Lys
            20                  25

<210> SEQ ID NO 111
<211> LENGTH: 7
<212> TYPE: PRT
<213> ORGANISM: Staphylococcus aureus

<400> SEQUENCE: 111

Ala Gly Trp Ala Glu Val Lys
1               5

<210> SEQ ID NO 112
<211> LENGTH: 9
<212> TYPE: PRT
<213> ORGANISM: Staphylococcus aureus

<400> SEQUENCE: 112

Thr Val Asp Ile Pro Lys Asp Pro Lys
1               5
```

```
<210> SEQ ID NO 113
<211> LENGTH: 9
<212> TYPE: PRT
<213> ORGANISM: Staphylococcus aureus

<400> SEQUENCE: 113

Lys Asp Trp Glu Glu Thr Thr Ala Lys
1               5

<210> SEQ ID NO 114
<211> LENGTH: 11
<212> TYPE: PRT
<213> ORGANISM: Staphylococcus aureus

<400> SEQUENCE: 114

Val Ala Pro Thr Val Val Asp Tyr Asn Lys
1               5                   10

<210> SEQ ID NO 115
<211> LENGTH: 10
<212> TYPE: PRT
<213> ORGANISM: Staphylococcus aureus

<400> SEQUENCE: 115

Tyr Leu Glu Gln Gln Glu Met Leu Gly Lys
1               5                   10

<210> SEQ ID NO 116
<211> LENGTH: 10
<212> TYPE: PRT
<213> ORGANISM: Staphylococcus aureus

<400> SEQUENCE: 116

Leu Tyr Thr Tyr Gly Asp Asn Trp Gly Arg
1               5                   10

<210> SEQ ID NO 117
<211> LENGTH: 13
<212> TYPE: PRT
<213> ORGANISM: Staphylococcus aureus

<400> SEQUENCE: 117

Ile Ala Val Val Ala Pro Thr Tyr Ala Gly Gly Leu Lys
1               5                   10

<210> SEQ ID NO 118
<211> LENGTH: 12
<212> TYPE: PRT
<213> ORGANISM: Staphylococcus aureus

<400> SEQUENCE: 118

Gly Gly Glu Val Leu Tyr Gln Ala Phe Gly Leu Lys
1               5                   10

<210> SEQ ID NO 119
<211> LENGTH: 13
<212> TYPE: PRT
<213> ORGANISM: Staphylococcus aureus

<400> SEQUENCE: 119

Ala Gly Trp Ala Glu Val Lys Gln Glu Glu Ile Glu Lys
1               5                   10

<210> SEQ ID NO 120
<211> LENGTH: 16
```

-continued

```
<212> TYPE: PRT
<213> ORGANISM: Staphylococcus aureus

<400> SEQUENCE: 120

Leu Gly Ala Asn Ile Val Ala Val Asn Gln Gln Val Asp Gln Ser Lys
1               5                   10                  15

<210> SEQ ID NO 121
<211> LENGTH: 16
<212> TYPE: PRT
<213> ORGANISM: Staphylococcus aureus

<400> SEQUENCE: 121

Glu Lys Pro Asp Leu Ile Ile Val Tyr Ser Thr Asp Lys Asp Ile Lys
1               5                   10                  15

<210> SEQ ID NO 122
<211> LENGTH: 17
<212> TYPE: PRT
<213> ORGANISM: Staphylococcus aureus

<400> SEQUENCE: 122

Ala Ile Gly Gln Asp Ala Thr Val Ser Leu Phe Asp Glu Phe Asp Lys
1               5                   10                  15

Lys

<210> SEQ ID NO 123
<211> LENGTH: 18
<212> TYPE: PRT
<213> ORGANISM: Staphylococcus aureus

<400> SEQUENCE: 123

Val Asp Ala Gly Thr Tyr Trp Tyr Asn Asp Pro Tyr Thr Leu Asp Phe
1               5                   10                  15

Met Arg

<210> SEQ ID NO 124
<211> LENGTH: 25
<212> TYPE: PRT
<213> ORGANISM: Staphylococcus aureus

<400> SEQUENCE: 124

Tyr Ala Gly Asp Tyr Ile Val Ser Thr Ser Glu Gly Lys Pro Thr Pro
1               5                   10                  15

Gly Tyr Glu Ser Thr Asn Met Trp Lys
            20                  25

<210> SEQ ID NO 125
<211> LENGTH: 7
<212> TYPE: PRT
<213> ORGANISM: Staphylococcus aureus

<400> SEQUENCE: 125

Gln Ala Ile Glu Phe Val Lys
1               5

<210> SEQ ID NO 126
<211> LENGTH: 7
<212> TYPE: PRT
<213> ORGANISM: Staphylococcus aureus

<400> SEQUENCE: 126

Tyr Ile Ala Gln Leu Glu Lys
```

```
1               5

<210> SEQ ID NO 127
<211> LENGTH: 8
<212> TYPE: PRT
<213> ORGANISM: Staphylococcus aureus

<400> SEQUENCE: 127

Gln Gly Thr Pro Glu Gln Met Arg
1               5

<210> SEQ ID NO 128
<211> LENGTH: 8
<212> TYPE: PRT
<213> ORGANISM: Staphylococcus aureus

<400> SEQUENCE: 128

Gln Ala Ile Glu Phe Val Lys Lys
1               5

<210> SEQ ID NO 129
<211> LENGTH: 8
<212> TYPE: PRT
<213> ORGANISM: Staphylococcus aureus

<400> SEQUENCE: 129

Asp Lys Phe Asn Asp Ile Pro Lys
1               5

<210> SEQ ID NO 130
<211> LENGTH: 10
<212> TYPE: PRT
<213> ORGANISM: Staphylococcus aureus

<400> SEQUENCE: 130

Ala Met Ile Thr Ser Glu Gly Ala Phe Lys
1               5                   10

<210> SEQ ID NO 131
<211> LENGTH: 11
<212> TYPE: PRT
<213> ORGANISM: Staphylococcus aureus

<400> SEQUENCE: 131

Ser Asn Ile Glu Thr Val His Gly Ser Met Lys
1               5                   10

<210> SEQ ID NO 132
<211> LENGTH: 11
<212> TYPE: PRT
<213> ORGANISM: Staphylococcus aureus

<400> SEQUENCE: 132

His Leu Leu Val Glu Thr Ser Val Asp Lys Lys
1               5                   10

<210> SEQ ID NO 133
<211> LENGTH: 13
<212> TYPE: PRT
<213> ORGANISM: Staphylococcus aureus

<400> SEQUENCE: 133

Asp Ile Phe Gly Glu Val Tyr Thr Asp Ser Ile Gly Lys
1               5                   10
```

<210> SEQ ID NO 134
<211> LENGTH: 12
<212> TYPE: PRT
<213> ORGANISM: Staphylococcus aureus

<400> SEQUENCE: 134

Thr Ile Gln Gln Thr Phe Ile Asp Asn Asp Lys Lys
1               5                   10

<210> SEQ ID NO 135
<211> LENGTH: 13
<212> TYPE: PRT
<213> ORGANISM: Staphylococcus aureus

<400> SEQUENCE: 135

Val Val Thr Thr Asn Ser Ile Leu Tyr Asp Met Ala Lys
1               5                   10

<210> SEQ ID NO 136
<211> LENGTH: 14
<212> TYPE: PRT
<213> ORGANISM: Staphylococcus aureus

<400> SEQUENCE: 136

Lys Asp Ile Phe Gly Glu Val Tyr Thr Asp Ser Ile Gly Lys
1               5                   10

<210> SEQ ID NO 137
<211> LENGTH: 14
<212> TYPE: PRT
<213> ORGANISM: Staphylococcus aureus

<400> SEQUENCE: 137

Gln Asp Pro His Ala Trp Leu Ser Leu Asp Asn Gly Ile Lys
1               5                   10

<210> SEQ ID NO 138
<211> LENGTH: 16
<212> TYPE: PRT
<213> ORGANISM: Staphylococcus aureus

<400> SEQUENCE: 138

Asp Val Lys Pro Ile Tyr Leu Asn Gly Glu Glu Gly Asn Lys Asp Lys
1               5                   10                  15

<210> SEQ ID NO 139
<211> LENGTH: 16
<212> TYPE: PRT
<213> ORGANISM: Staphylococcus aureus

<400> SEQUENCE: 139

Asp Lys Gln Asp Pro His Ala Trp Leu Ser Leu Asp Asn Gly Ile Lys
1               5                   10                  15

<210> SEQ ID NO 140
<211> LENGTH: 16
<212> TYPE: PRT
<213> ORGANISM: Staphylococcus aureus

<400> SEQUENCE: 140

Gln Tyr Gly Ile Thr Pro Gly Tyr Ile Trp Glu Ile Asn Thr Glu Lys
1               5                   10                  15

<210> SEQ ID NO 141

```
<211> LENGTH: 23
<212> TYPE: PRT
<213> ORGANISM: Staphylococcus aureus

<400> SEQUENCE: 141

Leu Thr Asp Ala Asp Val Ile Leu Tyr Asn Gly Leu Asn Leu Glu Thr
1               5                   10                  15

Gly Asn Gly Trp Phe Glu Lys
            20

<210> SEQ ID NO 142
<211> LENGTH: 24
<212> TYPE: PRT
<213> ORGANISM: Staphylococcus aureus

<400> SEQUENCE: 142

Lys Leu Thr Asp Ala Asp Val Ile Leu Tyr Asn Gly Leu Asn Leu Glu
1               5                   10                  15

Thr Gly Asn Gly Trp Phe Glu Lys
            20

<210> SEQ ID NO 143
<211> LENGTH: 27
<212> TYPE: PRT
<213> ORGANISM: Staphylococcus aureus

<400> SEQUENCE: 143

Asn Val Gly Gly Asp Asn Val Asp Ile His Ser Ile Val Pro Val Gly
1               5                   10                  15

Gln Asp Pro His Glu Tyr Glu Val Lys Pro Lys
            20                  25

<210> SEQ ID NO 144
<211> LENGTH: 6
<212> TYPE: PRT
<213> ORGANISM: Staphylococcus aureus

<400> SEQUENCE: 144

Leu His Ser Trp Leu Lys
1               5

<210> SEQ ID NO 145
<211> LENGTH: 7
<212> TYPE: PRT
<213> ORGANISM: Staphylococcus aureus

<400> SEQUENCE: 145

Lys Leu His Ser Trp Leu Lys
1               5

<210> SEQ ID NO 146
<211> LENGTH: 7
<212> TYPE: PRT
<213> ORGANISM: Staphylococcus aureus

<400> SEQUENCE: 146

Thr Tyr Thr Phe His Leu Arg
1               5

<210> SEQ ID NO 147
<211> LENGTH: 9
<212> TYPE: PRT
<213> ORGANISM: Staphylococcus aureus
```

```
<400> SEQUENCE: 147

Lys Phe Asp Gly Thr Gly Pro Phe Lys
1               5

<210> SEQ ID NO 148
<211> LENGTH: 9
<212> TYPE: PRT
<213> ORGANISM: Staphylococcus aureus

<400> SEQUENCE: 148

Gln Ala Ile Gly His Met Val Asn Arg
1               5

<210> SEQ ID NO 149
<211> LENGTH: 8
<212> TYPE: PRT
<213> ORGANISM: Staphylococcus aureus

<400> SEQUENCE: 149

Asn Asp Gln Tyr Trp Gly Glu Lys
1               5

<210> SEQ ID NO 150
<211> LENGTH: 11
<212> TYPE: PRT
<213> ORGANISM: Staphylococcus aureus

<400> SEQUENCE: 150

Gly Thr Asp Ser Leu Asp Lys Asp Ser Leu Lys
1               5                   10

<210> SEQ ID NO 151
<211> LENGTH: 10
<212> TYPE: PRT
<213> ORGANISM: Staphylococcus aureus

<400> SEQUENCE: 151

Ile Tyr Asn Ser Ile Asp Asp Ala Phe Lys
1               5                   10

<210> SEQ ID NO 152
<211> LENGTH: 10
<212> TYPE: PRT
<213> ORGANISM: Staphylococcus aureus

<400> SEQUENCE: 152

Asp Lys Tyr Thr Val Glu Leu Asn Leu Lys
1               5                   10

<210> SEQ ID NO 153
<211> LENGTH: 11
<212> TYPE: PRT
<213> ORGANISM: Staphylococcus aureus

<400> SEQUENCE: 153

Ile Ser Thr Leu Ile Asp Asn Val Lys Val Lys
1               5                   10

<210> SEQ ID NO 154
<211> LENGTH: 12
<212> TYPE: PRT
<213> ORGANISM: Staphylococcus aureus

<400> SEQUENCE: 154
```

```
Ala Glu Ser Leu Leu Asp Glu Ala Gly Trp Lys Lys
1               5                   10
```

<210> SEQ ID NO 155
<211> LENGTH: 11
<212> TYPE: PRT
<213> ORGANISM: Staphylococcus aureus

<400> SEQUENCE: 155

```
Glu Gln Ala Glu Tyr Leu Gln Ala Glu Phe Lys
1               5                   10
```

<210> SEQ ID NO 156
<211> LENGTH: 13
<212> TYPE: PRT
<213> ORGANISM: Staphylococcus aureus

<400> SEQUENCE: 156

```
Val Met Pro Ala Gly Glu Thr Ala Phe Leu Ser Met Lys
1               5                   10
```

<210> SEQ ID NO 157
<211> LENGTH: 12
<212> TYPE: PRT
<213> ORGANISM: Staphylococcus aureus

<400> SEQUENCE: 157

```
Lys Gly Glu Thr Asn Phe Ala Phe Thr Asp Asp Arg
1               5                   10
```

<210> SEQ ID NO 158
<211> LENGTH: 13
<212> TYPE: PRT
<213> ORGANISM: Staphylococcus aureus

<400> SEQUENCE: 158

```
Phe His Asp Gly Thr Pro Phe Asp Ala Asp Ala Val Lys
1               5                   10
```

<210> SEQ ID NO 159
<211> LENGTH: 12
<212> TYPE: PRT
<213> ORGANISM: Staphylococcus aureus

<400> SEQUENCE: 159

```
Asn Val Thr Asp Ile Asn Phe Asp Met Pro Thr Arg
1               5                   10
```

<210> SEQ ID NO 160
<211> LENGTH: 12
<212> TYPE: PRT
<213> ORGANISM: Staphylococcus aureus

<400> SEQUENCE: 160

```
Glu Gln Ala Glu Tyr Leu Gln Ala Glu Phe Lys Lys
1               5                   10
```

<210> SEQ ID NO 161
<211> LENGTH: 14
<212> TYPE: PRT
<213> ORGANISM: Staphylococcus aureus

<400> SEQUENCE: 161

```
Phe His Asp Gly Thr Pro Phe Asp Ala Asp Ala Val Lys Lys
1               5                   10
```

<210> SEQ ID NO 162
<211> LENGTH: 13
<212> TYPE: PRT
<213> ORGANISM: Staphylococcus aureus

<400> SEQUENCE: 162

Asn Val Thr Asp Ile Asn Phe Asp Met Pro Thr Arg Lys
1               5                   10

<210> SEQ ID NO 163
<211> LENGTH: 14
<212> TYPE: PRT
<213> ORGANISM: Staphylococcus aureus

<400> SEQUENCE: 163

Leu Asn Ile Asn Gly Glu Thr Ser Asp Lys Ile Ala Glu Arg
1               5                   10

<210> SEQ ID NO 164
<211> LENGTH: 16
<212> TYPE: PRT
<213> ORGANISM: Staphylococcus aureus

<400> SEQUENCE: 164

Glu Ile Leu Asp Gly Gln Glu Lys Pro Ala Thr Gln Leu Phe Ala Lys
1               5                   10                  15

<210> SEQ ID NO 165
<211> LENGTH: 16
<212> TYPE: PRT
<213> ORGANISM: Staphylococcus aureus

<400> SEQUENCE: 165

Asp Glu Ser Ala Asp Phe Asn Lys Asn Asp Gln Tyr Trp Gly Glu Lys
1               5                   10                  15

<210> SEQ ID NO 166
<211> LENGTH: 18
<212> TYPE: PRT
<213> ORGANISM: Staphylococcus aureus

<400> SEQUENCE: 166

Val Ser Phe Thr Gln Ser Gln Tyr Glu Leu Pro Phe Asn Glu Met Gln
1               5                   10                  15

Tyr Lys

<210> SEQ ID NO 167
<211> LENGTH: 22
<212> TYPE: PRT
<213> ORGANISM: Staphylococcus aureus

<400> SEQUENCE: 167

Gln Ile Asp Asp Glu Gly Ile Phe Ile Pro Ile Ser His Gly Ser Met
1               5                   10                  15

Thr Val Val Ala Pro Lys
            20

<210> SEQ ID NO 168
<211> LENGTH: 26
<212> TYPE: PRT
<213> ORGANISM: Staphylococcus aureus

<400> SEQUENCE: 168

```
Asp Ile Gly Asp Met Asn Pro His Val Tyr Gly Gly Ser Met Ser Ala
1               5                   10                  15

Glu Ser Met Ile Tyr Glu Pro Leu Val Arg
            20                  25

<210> SEQ ID NO 169
<211> LENGTH: 8
<212> TYPE: PRT
<213> ORGANISM: Staphylococcus aureus

<400> SEQUENCE: 169

Phe Pro Tyr Ala Ala Asn Gly Arg
1               5

<210> SEQ ID NO 170
<211> LENGTH: 8
<212> TYPE: PRT
<213> ORGANISM: Staphylococcus aureus

<400> SEQUENCE: 170

Ala Leu Leu His Ala Ser His Arg
1               5

<210> SEQ ID NO 171
<211> LENGTH: 10
<212> TYPE: PRT
<213> ORGANISM: Staphylococcus aureus

<400> SEQUENCE: 171

Glu Glu Gly Leu Ala Ile Lys Ala Ser Lys
1               5                   10

<210> SEQ ID NO 172
<211> LENGTH: 12
<212> TYPE: PRT
<213> ORGANISM: Staphylococcus aureus

<400> SEQUENCE: 172

Gly Glu Ala Tyr Phe Val Asp Asn Ser Leu Arg
1               5                   10

<210> SEQ ID NO 173
<211> LENGTH: 13
<212> TYPE: PRT
<213> ORGANISM: Staphylococcus aureus

<400> SEQUENCE: 173

Thr Ile Glu Ala Asp Tyr Val Leu Val Thr Val Gly Arg
1               5                   10

<210> SEQ ID NO 174
<211> LENGTH: 15
<212> TYPE: PRT
<213> ORGANISM: Staphylococcus aureus

<400> SEQUENCE: 174

Arg Pro Asn Thr Asp Glu Leu Gly Leu Glu Glu Leu Gly Val Lys
1               5                   10                  15

<210> SEQ ID NO 175
<211> LENGTH: 17
<212> TYPE: PRT
<213> ORGANISM: Staphylococcus aureus
```

<400> SEQUENCE: 175

Asn Ala Ile Ile Ala Thr Gly Ser Arg Pro Ile Glu Ile Pro Asn Phe
1               5                   10                  15

Lys

<210> SEQ ID NO 176
<211> LENGTH: 21
<212> TYPE: PRT
<213> ORGANISM: Staphylococcus aureus

<400> SEQUENCE: 176

Thr Ser Ile Ser Asn Ile Tyr Ala Ile Gly Asp Ile Val Pro Gly Leu
1               5                   10                  15

Pro Leu Ala His Lys
            20

<210> SEQ ID NO 177
<211> LENGTH: 23
<212> TYPE: PRT
<213> ORGANISM: Staphylococcus aureus

<400> SEQUENCE: 177

Phe Val Glu Ala Gln His Ser Glu Asn Leu Gly Val Ile Ala Glu Ser
1               5                   10                  15

Val Ser Leu Asn Phe Gln Lys
            20

<210> SEQ ID NO 178
<211> LENGTH: 26
<212> TYPE: PRT
<213> ORGANISM: Staphylococcus aureus

<400> SEQUENCE: 178

Val Val Gly Asp Phe Pro Ile Glu Thr Asp Thr Ile Val Ile Gly Ala
1               5                   10                  15

Gly Pro Gly Gly Tyr Val Ala Ala Ile Arg
            20                  25

<210> SEQ ID NO 179
<211> LENGTH: 5
<212> TYPE: PRT
<213> ORGANISM: Staphylococcus aureus

<400> SEQUENCE: 179

Phe Glu Tyr Ile Lys
1               5

<210> SEQ ID NO 180
<211> LENGTH: 6
<212> TYPE: PRT
<213> ORGANISM: Staphylococcus aureus

<400> SEQUENCE: 180

Asp Ala Trp Pro Leu Lys
1               5

<210> SEQ ID NO 181
<211> LENGTH: 7
<212> TYPE: PRT
<213> ORGANISM: Staphylococcus aureus

<400> SEQUENCE: 181

Ala Ser Val Val Asn Phe Arg
1               5

<210> SEQ ID NO 182
<211> LENGTH: 7
<212> TYPE: PRT
<213> ORGANISM: Staphylococcus aureus

<400> SEQUENCE: 182

Val Tyr Asp Gln Leu Ser Lys
1               5

<210> SEQ ID NO 183
<211> LENGTH: 8
<212> TYPE: PRT
<213> ORGANISM: Staphylococcus aureus

<400> SEQUENCE: 183

Leu Ile Asp Asp Leu Tyr Glu Lys
1               5

<210> SEQ ID NO 184
<211> LENGTH: 8
<212> TYPE: PRT
<213> ORGANISM: Staphylococcus aureus

<400> SEQUENCE: 184

Tyr Lys Asp Ala Trp Pro Leu Lys
1               5

<210> SEQ ID NO 185
<211> LENGTH: 9
<212> TYPE: PRT
<213> ORGANISM: Staphylococcus aureus

<400> SEQUENCE: 185

Glu Lys Glu Ala Glu Asp Leu Leu Lys
1               5

<210> SEQ ID NO 186
<211> LENGTH: 10
<212> TYPE: PRT
<213> ORGANISM: Staphylococcus aureus

<400> SEQUENCE: 186

Leu Lys Pro Asp Leu Ile Val Ala Ser Lys
1               5                   10

<210> SEQ ID NO 187
<211> LENGTH: 9
<212> TYPE: PRT
<213> ORGANISM: Staphylococcus aureus

<400> SEQUENCE: 187

Phe Glu Tyr Ile Lys Asn Asp Leu Lys
1               5

<210> SEQ ID NO 188
<211> LENGTH: 10
<212> TYPE: PRT
<213> ORGANISM: Staphylococcus aureus

<400> SEQUENCE: 188

Lys Thr Glu Ser Glu Trp Thr Ser Ser Lys
1               5                   10

<210> SEQ ID NO 189
<211> LENGTH: 10
<212> TYPE: PRT
<213> ORGANISM: Staphylococcus aureus

<400> SEQUENCE: 189

Tyr Asp Asp Lys Val Ala Ala Phe Gln Lys
1               5                   10

<210> SEQ ID NO 190
<211> LENGTH: 12
<212> TYPE: PRT
<213> ORGANISM: Staphylococcus aureus

<400> SEQUENCE: 190

Ile Ala Pro Thr Val Ser Thr Asp Thr Val Phe Lys
1               5                   10

<210> SEQ ID NO 191
<211> LENGTH: 14
<212> TYPE: PRT
<213> ORGANISM: Staphylococcus aureus

<400> SEQUENCE: 191

Gln Val Asp Asn Gly Lys Asp Ile Ile Gln Leu Thr Ser Lys
1               5                   10

<210> SEQ ID NO 192
<211> LENGTH: 15
<212> TYPE: PRT
<213> ORGANISM: Staphylococcus aureus

<400> SEQUENCE: 192

Ile Val Gly Gln Glu Pro Ala Pro Asn Leu Glu Glu Ile Ser Lys
1               5                   10                  15

<210> SEQ ID NO 193
<211> LENGTH: 15
<212> TYPE: PRT
<213> ORGANISM: Staphylococcus aureus

<400> SEQUENCE: 193

Glu Ser Ile Pro Leu Met Asn Ala Asp His Ile Phe Val Val Lys
1               5                   10                  15

<210> SEQ ID NO 194
<211> LENGTH: 17
<212> TYPE: PRT
<213> ORGANISM: Staphylococcus aureus

<400> SEQUENCE: 194

Ile Tyr Ala Gly Gly Tyr Ala Gly Glu Ile Leu Asn Asp Leu Gly Phe
1               5                   10                  15

Lys

<210> SEQ ID NO 195
<211> LENGTH: 18
<212> TYPE: PRT
<213> ORGANISM: Staphylococcus aureus

<400> SEQUENCE: 195

Ile Tyr Ala Gly Gly Tyr Ala Gly Glu Ile Leu Asn Asp Leu Gly Phe
1               5                   10                  15

-continued

Lys Arg

<210> SEQ ID NO 196
<211> LENGTH: 20
<212> TYPE: PRT
<213> ORGANISM: Staphylococcus aureus

<400> SEQUENCE: 196

Asn Asn Gln Val Ser Asp Asp Leu Asp Glu Ile Thr Trp Asn Leu Ala
1               5                   10                  15

Gly Gly Tyr Lys
            20

<210> SEQ ID NO 197
<211> LENGTH: 31
<212> TYPE: PRT
<213> ORGANISM: Staphylococcus aureus

<400> SEQUENCE: 197

Val Val Thr Leu Tyr Gln Gly Ala Thr Asp Val Ala Val Ser Leu Gly
1               5                   10                  15

Val Lys Pro Val Gly Ala Val Glu Ser Trp Thr Gln Lys Pro Lys
            20                  25                  30

<210> SEQ ID NO 198
<211> LENGTH: 7
<212> TYPE: PRT
<213> ORGANISM: Staphylococcus aureus

<400> SEQUENCE: 198

Tyr Ile Ala Gln Leu Glu Lys
1               5

<210> SEQ ID NO 199
<211> LENGTH: 8
<212> TYPE: PRT
<213> ORGANISM: Staphylococcus aureus

<400> SEQUENCE: 199

Gln Gly Thr Pro Glu Gln Met Arg
1               5

<210> SEQ ID NO 200
<211> LENGTH: 8
<212> TYPE: PRT
<213> ORGANISM: Staphylococcus aureus

<400> SEQUENCE: 200

Asp Lys Phe Asn Asp Ile Pro Lys
1               5

<210> SEQ ID NO 201
<211> LENGTH: 10
<212> TYPE: PRT
<213> ORGANISM: Staphylococcus aureus

<400> SEQUENCE: 201

Ala Met Ile Thr Ser Glu Gly Ala Phe Lys
1               5                   10

<210> SEQ ID NO 202
<211> LENGTH: 9
<212> TYPE: PRT

<213> ORGANISM: Staphylococcus aureus

<400> SEQUENCE: 202

Phe Asn Asp Ile Pro Lys Glu Gln Arg
1               5

<210> SEQ ID NO 203
<211> LENGTH: 11
<212> TYPE: PRT
<213> ORGANISM: Staphylococcus aureus

<400> SEQUENCE: 203

His Leu Leu Val Glu Thr Ser Val Asp Lys Lys
1               5                   10

<210> SEQ ID NO 204
<211> LENGTH: 11
<212> TYPE: PRT
<213> ORGANISM: Staphylococcus aureus

<400> SEQUENCE: 204

Thr Ile Gln Gln Thr Phe Ile Asp Asn Asp Lys
1               5                   10

<210> SEQ ID NO 205
<211> LENGTH: 13
<212> TYPE: PRT
<213> ORGANISM: Staphylococcus aureus

<400> SEQUENCE: 205

Asp Ile Phe Gly Glu Val Tyr Thr Asp Ser Ile Gly Lys
1               5                   10

<210> SEQ ID NO 206
<211> LENGTH: 12
<212> TYPE: PRT
<213> ORGANISM: Staphylococcus aureus

<400> SEQUENCE: 206

Thr Ile Gln Gln Thr Phe Ile Asp Asn Asp Lys Lys
1               5                   10

<210> SEQ ID NO 207
<211> LENGTH: 13
<212> TYPE: PRT
<213> ORGANISM: Staphylococcus aureus

<400> SEQUENCE: 207

Val Val Thr Thr Asn Ser Ile Leu Tyr Asp Met Ala Lys
1               5                   10

<210> SEQ ID NO 208
<211> LENGTH: 14
<212> TYPE: PRT
<213> ORGANISM: Staphylococcus aureus

<400> SEQUENCE: 208

Gln Asp Pro His Ala Trp Leu Ser Leu Asp Asn Gly Ile Lys
1               5                   10

<210> SEQ ID NO 209
<211> LENGTH: 16
<212> TYPE: PRT
<213> ORGANISM: Staphylococcus aureus

```
<400> SEQUENCE: 209

Asp Val Lys Pro Ile Tyr Leu Asn Gly Glu Glu Gly Asn Lys Asp Lys
1               5                   10                  15

<210> SEQ ID NO 210
<211> LENGTH: 16
<212> TYPE: PRT
<213> ORGANISM: Staphylococcus aureus

<400> SEQUENCE: 210

Asp Lys Gln Asp Pro His Ala Trp Leu Ser Leu Asp Asn Gly Ile Lys
1               5                   10                  15

<210> SEQ ID NO 211
<211> LENGTH: 16
<212> TYPE: PRT
<213> ORGANISM: Staphylococcus aureus

<400> SEQUENCE: 211

Gln Tyr Gly Ile Thr Pro Gly Tyr Ile Trp Glu Ile Asn Thr Glu Lys
1               5                   10                  15

<210> SEQ ID NO 212
<211> LENGTH: 27
<212> TYPE: PRT
<213> ORGANISM: Staphylococcus aureus

<400> SEQUENCE: 212

Asn Val Gly Gly Asp Asn Val Asp Ile His Ser Ile Val Pro Val Gly
1               5                   10                  15

Gln Asp Pro His Glu Tyr Glu Val Lys Pro Lys
            20                  25

<210> SEQ ID NO 213
<211> LENGTH: 6
<212> TYPE: PRT
<213> ORGANISM: Staphylococcus aureus

<400> SEQUENCE: 213

Ile Ile Gly Asp Tyr Arg
1               5

<210> SEQ ID NO 214
<211> LENGTH: 6
<212> TYPE: PRT
<213> ORGANISM: Staphylococcus aureus

<400> SEQUENCE: 214

Ile Phe Thr Asp Tyr Arg
1               5

<210> SEQ ID NO 215
<211> LENGTH: 9
<212> TYPE: PRT
<213> ORGANISM: Staphylococcus aureus

<400> SEQUENCE: 215

Thr Gly Asn Thr Pro Asp Gly Arg Lys
1               5

<210> SEQ ID NO 216
<211> LENGTH: 9
<212> TYPE: PRT
<213> ORGANISM: Staphylococcus aureus
```

```
<400> SEQUENCE: 216

Glu Gln Gln Leu Asp Val Ile Ser Arg
1               5

<210> SEQ ID NO 217
<211> LENGTH: 10
<212> TYPE: PRT
<213> ORGANISM: Staphylococcus aureus

<400> SEQUENCE: 217

Leu Arg Glu Glu Leu Ser Glu Gln Tyr Arg
1               5                   10

<210> SEQ ID NO 218
<211> LENGTH: 13
<212> TYPE: PRT
<213> ORGANISM: Staphylococcus aureus

<400> SEQUENCE: 218

Asn His Ala Thr Ala Trp Gln Gly Phe Lys Asn Gly Arg
1               5                   10

<210> SEQ ID NO 219
<211> LENGTH: 16
<212> TYPE: PRT
<213> ORGANISM: Staphylococcus aureus

<400> SEQUENCE: 219

Asp Leu Glu Thr Ile Val Gly Val Gln Thr Glu Lys Pro Phe Lys Arg
1               5                   10                  15

<210> SEQ ID NO 220
<211> LENGTH: 20
<212> TYPE: PRT
<213> ORGANISM: Staphylococcus aureus

<400> SEQUENCE: 220

Thr Met Ala Thr Gly Ile Ala Gly Leu Ser Val Ala Ala Asp Ser Leu
1               5                   10                  15

Ser Ala Ile Lys
            20

<210> SEQ ID NO 221
<211> LENGTH: 19
<212> TYPE: PRT
<213> ORGANISM: Staphylococcus aureus

<400> SEQUENCE: 221

Ala Gly Val Ile Thr Glu Ser Glu Val Gln Glu Ile Ile Asp His Phe
1               5                   10                  15

Ile Met Lys

<210> SEQ ID NO 222
<211> LENGTH: 23
<212> TYPE: PRT
<213> ORGANISM: Staphylococcus aureus

<400> SEQUENCE: 222

Phe Leu His Ser Leu Asp Asn Leu Gly Pro Ala Pro Glu Pro Asn Leu
1               5                   10                  15

Thr Val Leu Trp Ser Val Arg
            20
```

<210> SEQ ID NO 223
<211> LENGTH: 24
<212> TYPE: PRT
<213> ORGANISM: Staphylococcus aureus

<400> SEQUENCE: 223

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 224
<211> LENGTH: 25
<212> TYPE: PRT
<213> ORGANISM: Staphylococcus aureus

<400> SEQUENCE: 224

Ser Gly Ala Gln Val Gly Pro Asn Phe Glu Gly Ile Asn Ser Glu Val
1               5                   10                  15

Leu Glu Tyr Asp Glu Val Phe Lys Lys
            20                  25

<210> SEQ ID NO 225
<211> LENGTH: 30
<212> TYPE: PRT
<213> ORGANISM: Staphylococcus aureus

<400> SEQUENCE: 225

Val Ala Ser Thr Ile Thr Ser His Asp Ala Gly Tyr Leu Asp Lys Asp
1               5                   10                  15

Leu Glu Thr Ile Val Gly Val Gln Thr Glu Lys Pro Phe Lys
            20                  25                  30

<210> SEQ ID NO 226
<211> LENGTH: 6
<212> TYPE: PRT
<213> ORGANISM: Staphylococcus aureus

<400> SEQUENCE: 226

Ile Ile Gly Asp Tyr Arg
1               5

<210> SEQ ID NO 227
<211> LENGTH: 6
<212> TYPE: PRT
<213> ORGANISM: Staphylococcus aureus

<400> SEQUENCE: 227

Ile Phe Thr Asp Tyr Arg
1               5

<210> SEQ ID NO 228
<211> LENGTH: 9
<212> TYPE: PRT
<213> ORGANISM: Staphylococcus aureus

<400> SEQUENCE: 228

Glu Gln Gln Leu Asp Val Ile Ser Arg
1               5

<210> SEQ ID NO 229
<211> LENGTH: 11

```
<212> TYPE: PRT
<213> ORGANISM: Staphylococcus aureus

<400> SEQUENCE: 229

Val Asp Asp Ile Ala Val Asp Leu Val Glu Arg
1               5                   10

<210> SEQ ID NO 230
<211> LENGTH: 10
<212> TYPE: PRT
<213> ORGANISM: Staphylococcus aureus

<400> SEQUENCE: 230

Leu Arg Glu Glu Leu Ser Glu Gln Tyr Arg
1               5                   10

<210> SEQ ID NO 231
<211> LENGTH: 13
<212> TYPE: PRT
<213> ORGANISM: Staphylococcus aureus

<400> SEQUENCE: 231

Asn His Ala Thr Ala Trp Gln Gly Phe Lys Asn Gly Arg
1               5                   10

<210> SEQ ID NO 232
<211> LENGTH: 15
<212> TYPE: PRT
<213> ORGANISM: Staphylococcus aureus

<400> SEQUENCE: 232

Asp Leu Glu Thr Ile Val Gly Val Gln Thr Glu Lys Pro Phe Lys
1               5                   10                  15

<210> SEQ ID NO 233
<211> LENGTH: 15
<212> TYPE: PRT
<213> ORGANISM: Staphylococcus aureus

<400> SEQUENCE: 233

Glu Ala Val Gln Trp Leu Tyr Leu Ala Tyr Leu Ala Ala Ile Lys
1               5                   10                  15

<210> SEQ ID NO 234
<211> LENGTH: 16
<212> TYPE: PRT
<213> ORGANISM: Staphylococcus aureus

<400> SEQUENCE: 234

Asp Leu Glu Thr Ile Val Gly Val Gln Thr Glu Lys Pro Phe Lys Arg
1               5                   10                  15

<210> SEQ ID NO 235
<211> LENGTH: 20
<212> TYPE: PRT
<213> ORGANISM: Staphylococcus aureus

<400> SEQUENCE: 235

Thr Met Ala Thr Gly Ile Ala Gly Leu Ser Val Ala Ala Asp Ser Leu
1               5                   10                  15

Ser Ala Ile Lys
            20

<210> SEQ ID NO 236
```

```
<211> LENGTH: 17
<212> TYPE: PRT
<213> ORGANISM: Staphylococcus aureus

<400> SEQUENCE: 236

Asn Glu Glu Gly Leu Val Val Asp Phe Glu Ile Glu Gly Asp Phe Pro
1               5                   10                  15

Lys

<210> SEQ ID NO 237
<211> LENGTH: 19
<212> TYPE: PRT
<213> ORGANISM: Staphylococcus aureus

<400> SEQUENCE: 237

Ala Gly Val Ile Thr Glu Ser Glu Val Gln Glu Ile Ile Asp His Phe
1               5                   10                  15

Ile Met Lys

<210> SEQ ID NO 238
<211> LENGTH: 23
<212> TYPE: PRT
<213> ORGANISM: Staphylococcus aureus

<400> SEQUENCE: 238

Phe Leu His Ser Leu Asp Asn Leu Gly Pro Ala Pro Glu Pro Asn Leu
1               5                   10                  15

Thr Val Leu Trp Ser Val Arg
            20

<210> SEQ ID NO 239
<211> LENGTH: 24
<212> TYPE: PRT
<213> ORGANISM: Staphylococcus aureus

<400> SEQUENCE: 239

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 240
<211> LENGTH: 25
<212> TYPE: PRT
<213> ORGANISM: Staphylococcus aureus

<400> SEQUENCE: 240

Ser Gly Ala Gln Val Gly Pro Asn Phe Glu Gly Ile Asn Ser Glu Val
1               5                   10                  15

Leu Glu Tyr Asp Glu Val Phe Lys Lys
            20                  25

<210> SEQ ID NO 241
<211> LENGTH: 26
<212> TYPE: PRT
<213> ORGANISM: Staphylococcus aureus

<400> SEQUENCE: 241

Glu Phe Ile Gln Leu Asn Tyr Thr Leu Tyr Glu Gly Asn Asp Ser Phe
1               5                   10                  15

Leu Ala Gly Pro Thr Glu Ala Thr Ser Lys
            20                  25
```

<210> SEQ ID NO 242
<211> LENGTH: 30
<212> TYPE: PRT
<213> ORGANISM: Staphylococcus aureus

<400> SEQUENCE: 242

Val Ala Ser Thr Ile Thr Ser His Asp Ala Gly Tyr Leu Asp Lys Asp
1               5                   10                  15

Leu Glu Thr Ile Val Gly Val Gln Thr Glu Lys Pro Phe Lys
            20                  25                  30

<210> SEQ ID NO 243
<211> LENGTH: 32
<212> TYPE: PRT
<213> ORGANISM: Staphylococcus aureus

<400> SEQUENCE: 243

Thr Pro Asp Tyr Asn Glu Leu Phe Ser Gly Asp Pro Thr Trp Val Thr
1               5                   10                  15

Glu Ser Ile Gly Gly Val Gly Ile Asp Gly Arg Pro Leu Val Thr Lys
            20                  25                  30

<210> SEQ ID NO 244
<211> LENGTH: 6
<212> TYPE: PRT
<213> ORGANISM: Staphylococcus aureus

<400> SEQUENCE: 244

Leu Pro Asp Asn Phe Lys
1               5

<210> SEQ ID NO 245
<211> LENGTH: 6
<212> TYPE: PRT
<213> ORGANISM: Staphylococcus aureus

<400> SEQUENCE: 245

Ile Ile Gly Asp Tyr Arg
1               5

<210> SEQ ID NO 246
<211> LENGTH: 6
<212> TYPE: PRT
<213> ORGANISM: Staphylococcus aureus

<400> SEQUENCE: 246

Ile Phe Thr Asp Tyr Arg
1               5

<210> SEQ ID NO 247
<211> LENGTH: 7
<212> TYPE: PRT
<213> ORGANISM: Staphylococcus aureus

<400> SEQUENCE: 247

Tyr Gly Asn Asn Asp Asp Arg
1               5

<210> SEQ ID NO 248
<211> LENGTH: 10
<212> TYPE: PRT
<213> ORGANISM: Staphylococcus aureus

<400> SEQUENCE: 248

Thr Leu Leu Tyr Ala Ile Asn Gly Gly Lys
1               5                   10

<210> SEQ ID NO 249
<211> LENGTH: 9
<212> TYPE: PRT
<213> ORGANISM: Staphylococcus aureus

<400> SEQUENCE: 249

Glu Gln Gln Leu Asp Val Ile Ser Arg
1               5

<210> SEQ ID NO 250
<211> LENGTH: 10
<212> TYPE: PRT
<213> ORGANISM: Staphylococcus aureus

<400> SEQUENCE: 250

Leu Arg Glu Glu Leu Ser Glu Gln Tyr Arg
1               5                   10

<210> SEQ ID NO 251
<211> LENGTH: 12
<212> TYPE: PRT
<213> ORGANISM: Staphylococcus aureus
<220> FEATURE:
<221> NAME/KEY: MOD_RES
<222> LOCATION: (3)..(3)
<223> OTHER INFORMATION: Oxidized Met

<400> SEQUENCE: 251

Ile Glu Met Ala Leu His Asp Thr Glu Ile Val Arg
1               5                   10

<210> SEQ ID NO 252
<211> LENGTH: 13
<212> TYPE: PRT
<213> ORGANISM: Staphylococcus aureus

<400> SEQUENCE: 252

Val Ser Gly Tyr Ala Val Asn Phe Ile Lys Leu Thr Arg
1               5                   10

<210> SEQ ID NO 253
<211> LENGTH: 15
<212> TYPE: PRT
<213> ORGANISM: Staphylococcus aureus
<220> FEATURE:
<221> NAME/KEY: MOD_RES
<222> LOCATION: (12)..(12)
<223> OTHER INFORMATION: Oxidized Met

<400> SEQUENCE: 253

Ala Gly Glu Pro Phe Ala Pro Gly Ala Asn Pro Met His Gly Arg
1               5                   10                  15

<210> SEQ ID NO 254
<211> LENGTH: 13
<212> TYPE: PRT
<213> ORGANISM: Staphylococcus aureus
<220> FEATURE:
<221> NAME/KEY: MOD_RES
<222> LOCATION: (10)..(10)
<223> OTHER INFORMATION: Oxidized Met

<400> SEQUENCE: 254

Val Ala Leu Tyr Gly Val Asp Phe Leu Met Glu Glu Lys
1               5                   10

<210> SEQ ID NO 255
<211> LENGTH: 16
<212> TYPE: PRT
<213> ORGANISM: Staphylococcus aureus
<220> FEATURE:
<221> NAME/KEY: MOD_RES
<222> LOCATION: (13)..(13)
<223> OTHER INFORMATION: Oxidized Met

<400> SEQUENCE: 255

Lys Ala Gly Glu Pro Phe Ala Pro Gly Ala Asn Pro Met His Gly Arg
1               5                   10                  15

<210> SEQ ID NO 256
<211> LENGTH: 14
<212> TYPE: PRT
<213> ORGANISM: Staphylococcus aureus

<400> SEQUENCE: 256

Thr Ser Thr Phe Leu Asp Ile Tyr Ala Glu Arg Asp Leu Lys
1               5                   10

<210> SEQ ID NO 257
<211> LENGTH: 15
<212> TYPE: PRT
<213> ORGANISM: Staphylococcus aureus
<220> FEATURE:
<221> NAME/KEY: MOD_RES
<222> LOCATION: (13)..(13)
<223> OTHER INFORMATION: Oxidized Met

<400> SEQUENCE: 257

Val Asp Asp Ile Ala Val Asp Leu Val Glu Arg Phe Met Thr Lys
1               5                   10                  15

<210> SEQ ID NO 258
<211> LENGTH: 20
<212> TYPE: PRT
<213> ORGANISM: Staphylococcus aureus

<400> SEQUENCE: 258

Thr Met Ala Thr Gly Ile Ala Gly Leu Ser Val Ala Ala Asp Ser Leu
1               5                   10                  15

Ser Ala Ile Lys
            20

<210> SEQ ID NO 259
<211> LENGTH: 20
<212> TYPE: PRT
<213> ORGANISM: Staphylococcus aureus
<220> FEATURE:
<221> NAME/KEY: MOD_RES
<222> LOCATION: (6)..(6)
<223> OTHER INFORMATION: Oxidized Met

<400> SEQUENCE: 259

Asp Ser Glu His Thr Met Ser Val Leu Thr Ile Thr Ser Asn Val Val
1               5                   10                  15

Tyr Gly Lys Lys
            20

<210> SEQ ID NO 260

```
<211> LENGTH: 23
<212> TYPE: PRT
<213> ORGANISM: Staphylococcus aureus

<400> SEQUENCE: 260

Phe Leu His Ser Leu Asp Asn Leu Gly Pro Ala Pro Glu Pro Asn Leu
1               5                   10                  15

Thr Val Leu Trp Ser Val Arg
            20

<210> SEQ ID NO 261
<211> LENGTH: 24
<212> TYPE: PRT
<213> ORGANISM: Staphylococcus aureus

<400> SEQUENCE: 261

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 262
<211> LENGTH: 24
<212> TYPE: PRT
<213> ORGANISM: Staphylococcus aureus

<400> SEQUENCE: 262

Asn Leu Thr Ser Met Leu Asp Gly Tyr Ala Met Gln Cys Gly His His
1               5                   10                  15

Leu Asn Ile Asn Val Phe Asn Arg
            20

<210> SEQ ID NO 263
<211> LENGTH: 25
<212> TYPE: PRT
<213> ORGANISM: Staphylococcus aureus

<400> SEQUENCE: 263

Ser Gly Ala Gln Val Gly Pro Asn Phe Glu Gly Ile Asn Ser Glu Val
1               5                   10                  15

Leu Glu Tyr Asp Glu Val Phe Lys Lys
            20                  25

<210> SEQ ID NO 264
<211> LENGTH: 27
<212> TYPE: PRT
<213> ORGANISM: Staphylococcus aureus

<400> SEQUENCE: 264

Asp Glu Lys Ser Gly Ala Gln Val Gly Pro Asn Phe Glu Gly Ile Asn
1               5                   10                  15

Ser Glu Val Leu Glu Tyr Asp Glu Val Phe Lys
            20                  25

<210> SEQ ID NO 265
<211> LENGTH: 32
<212> TYPE: PRT
<213> ORGANISM: Staphylococcus aureus

<400> SEQUENCE: 265

Thr Pro Asp Tyr Asn Glu Leu Phe Ser Gly Asp Pro Thr Trp Val Thr
1               5                   10                  15
```

```
Glu Ser Ile Gly Gly Val Gly Ile Asp Gly Arg Pro Leu Val Thr Lys
        20                  25                  30
```

<210> SEQ ID NO 266
<211> LENGTH: 6
<212> TYPE: PRT
<213> ORGANISM: Staphylococcus aureus

<400> SEQUENCE: 266

```
Ala Lys Ser Asn Ser Lys
1               5
```

<210> SEQ ID NO 267
<211> LENGTH: 7
<212> TYPE: PRT
<213> ORGANISM: Staphylococcus aureus

<400> SEQUENCE: 267

```
Thr Phe Tyr Pro Glu Ala Arg
1               5
```

<210> SEQ ID NO 268
<211> LENGTH: 8
<212> TYPE: PRT
<213> ORGANISM: Staphylococcus aureus

<400> SEQUENCE: 268

```
Gln Phe Trp Gly His Leu Val Lys
1               5
```

<210> SEQ ID NO 269
<211> LENGTH: 9
<212> TYPE: PRT
<213> ORGANISM: Staphylococcus aureus

<400> SEQUENCE: 269

```
Trp Ile Pro Leu Met Met Lys Gly Arg
1               5
```

<210> SEQ ID NO 270
<211> LENGTH: 10
<212> TYPE: PRT
<213> ORGANISM: Staphylococcus aureus

<400> SEQUENCE: 270

```
Val Ile Asn Glu Glu Phe Glu Ile Ser Lys
1               5                   10
```

<210> SEQ ID NO 271
<211> LENGTH: 11
<212> TYPE: PRT
<213> ORGANISM: Staphylococcus aureus

<400> SEQUENCE: 271

```
Asn Glu Asp Trp Gln Leu Tyr Thr Ala Gly Lys
1               5                   10
```

<210> SEQ ID NO 272
<211> LENGTH: 13
<212> TYPE: PRT
<213> ORGANISM: Staphylococcus aureus

<400> SEQUENCE: 272

```
Thr Leu Leu Phe Gly Pro Phe Ala Asn Val Gly Pro Lys
1               5                   10
```

```
<210> SEQ ID NO 273
<211> LENGTH: 12
<212> TYPE: PRT
<213> ORGANISM: Staphylococcus aureus

<400> SEQUENCE: 273

Leu Asp Arg Pro Ala Ile Glu Ser Ser Asn Glu Arg
1               5                   10

<210> SEQ ID NO 274
<211> LENGTH: 14
<212> TYPE: PRT
<213> ORGANISM: Staphylococcus aureus

<400> SEQUENCE: 274

Ile Asp Glu Gly Thr Asp Val Asn Phe Gly Glu Leu Thr Arg
1               5                   10

<210> SEQ ID NO 275
<211> LENGTH: 13
<212> TYPE: PRT
<213> ORGANISM: Staphylococcus aureus

<400> SEQUENCE: 275

Glu Phe Ile Asn Pro Leu Pro His Ile Ser Tyr Val Arg
1               5                   10

<210> SEQ ID NO 276
<211> LENGTH: 13
<212> TYPE: PRT
<213> ORGANISM: Staphylococcus aureus

<400> SEQUENCE: 276

Glu Ile Glu Pro Asp Trp Asn Ile His Val Tyr Glu Arg
1               5                   10

<210> SEQ ID NO 277
<211> LENGTH: 16
<212> TYPE: PRT
<213> ORGANISM: Staphylococcus aureus

<400> SEQUENCE: 277

Glu Pro Pro Gly Thr Pro Pro Met Thr Val Pro His Leu Asp Thr Arg
1               5                   10                  15

<210> SEQ ID NO 278
<211> LENGTH: 20
<212> TYPE: PRT
<213> ORGANISM: Staphylococcus aureus

<400> SEQUENCE: 278

Gln Val Thr Asp Tyr Val Phe Ile Gly Ala Gly Gly Gly Ala Ile Pro
1               5                   10                  15

Leu Leu Gln Lys
            20

<210> SEQ ID NO 279
<211> LENGTH: 18
<212> TYPE: PRT
<213> ORGANISM: Staphylococcus aureus

<400> SEQUENCE: 279

Thr Phe Tyr Pro Glu Ala Arg Asn Glu Asp Trp Gln Leu Tyr Thr Ala
```

<210> SEQ ID NO 280
<211> LENGTH: 26
<212> TYPE: PRT
<213> ORGANISM: Staphylococcus aureus

<400> SEQUENCE: 280

His Leu Gly Gly Phe Pro Ile Ser Gly Gln Phe Leu Ala Cys Thr Asn
1               5                   10                  15

Pro Gln Val Ile Glu Gln His Asp Ala Lys
            20                  25

<210> SEQ ID NO 281
<211> LENGTH: 5
<212> TYPE: PRT
<213> ORGANISM: Staphylococcus aureus

<400> SEQUENCE: 281

Phe Glu Tyr Ile Lys
1               5

<210> SEQ ID NO 282
<211> LENGTH: 6
<212> TYPE: PRT
<213> ORGANISM: Staphylococcus aureus

<400> SEQUENCE: 282

Asp Ala Trp Pro Leu Lys
1               5

<210> SEQ ID NO 283
<211> LENGTH: 7
<212> TYPE: PRT
<213> ORGANISM: Staphylococcus aureus

<400> SEQUENCE: 283

Ala Ser Val Val Asn Phe Arg
1               5

<210> SEQ ID NO 284
<211> LENGTH: 7
<212> TYPE: PRT
<213> ORGANISM: Staphylococcus aureus

<400> SEQUENCE: 284

Val Tyr Asp Gln Leu Ser Lys
1               5

<210> SEQ ID NO 285
<211> LENGTH: 8
<212> TYPE: PRT
<213> ORGANISM: Staphylococcus aureus

<400> SEQUENCE: 285

Leu Ile Asp Asp Leu Tyr Glu Lys
1               5

<210> SEQ ID NO 286
<211> LENGTH: 8
<212> TYPE: PRT
<213> ORGANISM: Staphylococcus aureus

<400> SEQUENCE: 286

Tyr Lys Asp Ala Trp Pro Leu Lys
1               5

<210> SEQ ID NO 287
<211> LENGTH: 10
<212> TYPE: PRT
<213> ORGANISM: Staphylococcus aureus

<400> SEQUENCE: 287

Leu Lys Pro Asp Leu Ile Val Ala Ser Lys
1               5                   10

<210> SEQ ID NO 288
<211> LENGTH: 12
<212> TYPE: PRT
<213> ORGANISM: Staphylococcus aureus

<400> SEQUENCE: 288

Ile Ala Pro Thr Val Ser Thr Asp Thr Val Phe Lys
1               5                   10

<210> SEQ ID NO 289
<211> LENGTH: 15
<212> TYPE: PRT
<213> ORGANISM: Staphylococcus aureus

<400> SEQUENCE: 289

Ile Val Gly Gln Glu Pro Ala Pro Asn Leu Glu Glu Ile Ser Lys
1               5                   10                  15

<210> SEQ ID NO 290
<211> LENGTH: 15
<212> TYPE: PRT
<213> ORGANISM: Staphylococcus aureus

<400> SEQUENCE: 290

Glu Ser Ile Pro Leu Met Asn Ala Asp His Ile Phe Val Val Lys
1               5                   10                  15

<210> SEQ ID NO 291
<211> LENGTH: 17
<212> TYPE: PRT
<213> ORGANISM: Staphylococcus aureus

<400> SEQUENCE: 291

Ile Tyr Ala Gly Gly Tyr Ala Gly Glu Ile Leu Asn Asp Leu Gly Phe
1               5                   10                  15

Lys

<210> SEQ ID NO 292
<211> LENGTH: 18
<212> TYPE: PRT
<213> ORGANISM: Staphylococcus aureus

<400> SEQUENCE: 292

Ile Tyr Ala Gly Gly Tyr Ala Gly Glu Ile Leu Asn Asp Leu Gly Phe
1               5                   10                  15

Lys Arg

<210> SEQ ID NO 293
<211> LENGTH: 20
<212> TYPE: PRT

<213> ORGANISM: Staphylococcus aureus

<400> SEQUENCE: 293

Asn Asn Gln Val Ser Asp Asp Leu Asp Glu Ile Thr Trp Asn Leu Ala
1               5                   10                  15
Gly Gly Tyr Lys
            20

<210> SEQ ID NO 294
<211> LENGTH: 31
<212> TYPE: PRT
<213> ORGANISM: Staphylococcus aureus

<400> SEQUENCE: 294

Val Val Thr Leu Tyr Gln Gly Ala Thr Asp Val Ala Val Ser Leu Gly
1               5                   10                  15
Val Lys Pro Val Gly Ala Val Glu Ser Trp Thr Gln Lys Pro Lys
            20                  25                  30

<210> SEQ ID NO 295
<211> LENGTH: 5
<212> TYPE: PRT
<213> ORGANISM: Staphylococcus aureus

<400> SEQUENCE: 295

Asp Val Trp Ala Arg
1               5

<210> SEQ ID NO 296
<211> LENGTH: 6
<212> TYPE: PRT
<213> ORGANISM: Staphylococcus aureus

<400> SEQUENCE: 296

Lys Leu Asn Ala Val Lys
1               5

<210> SEQ ID NO 297
<211> LENGTH: 6
<212> TYPE: PRT
<213> ORGANISM: Staphylococcus aureus

<400> SEQUENCE: 297

Val Asp Ile Val Asp Arg
1               5

<210> SEQ ID NO 298
<211> LENGTH: 6
<212> TYPE: PRT
<213> ORGANISM: Staphylococcus aureus

<400> SEQUENCE: 298

Ile Ile Lys Pro Val Arg
1               5

<210> SEQ ID NO 299
<211> LENGTH: 8
<212> TYPE: PRT
<213> ORGANISM: Staphylococcus aureus

<400> SEQUENCE: 299

Ile Ala Pro Thr Leu Ser Leu Lys
1               5

```
<210> SEQ ID NO 300
<211> LENGTH: 7
<212> TYPE: PRT
<213> ORGANISM: Staphylococcus aureus

<400> SEQUENCE: 300

Gln Asn Ile Asn Ser Phe Lys
1               5

<210> SEQ ID NO 301
<211> LENGTH: 10
<212> TYPE: PRT
<213> ORGANISM: Staphylococcus aureus

<400> SEQUENCE: 301

Ile Gly Asp Tyr Thr Ser Val Gly Thr Arg
1               5                   10

<210> SEQ ID NO 302
<211> LENGTH: 9
<212> TYPE: PRT
<213> ORGANISM: Staphylococcus aureus
<220> FEATURE:
<221> NAME/KEY: MISC_FEATURE
<223> OTHER INFORMATION: One of the two Mets in this sequence is
      oxidized.
<220> FEATURE:
<221> NAME/KEY: MOD_RES
<222> LOCATION: (1)..(1)
<223> OTHER INFORMATION: This residue may or may not be oxidized
<220> FEATURE:
<221> NAME/KEY: MOD_RES
<222> LOCATION: (4)..(4)
<223> OTHER INFORMATION: This residue may or may not be oxidized

<400> SEQUENCE: 302

Met Ile Ile Met Thr Asp His Ala Lys
1               5

<210> SEQ ID NO 303
<211> LENGTH: 10
<212> TYPE: PRT
<213> ORGANISM: Staphylococcus aureus

<400> SEQUENCE: 303

Lys Gln Pro Asn Leu Glu Glu Ile Ser Lys
1               5                   10

<210> SEQ ID NO 304
<211> LENGTH: 12
<212> TYPE: PRT
<213> ORGANISM: Staphylococcus aureus

<400> SEQUENCE: 304

Leu Lys Pro Asp Leu Ile Ile Ala Asp Ser Ser Arg
1               5                   10

<210> SEQ ID NO 305
<211> LENGTH: 11
<212> TYPE: PRT
<213> ORGANISM: Staphylococcus aureus

<400> SEQUENCE: 305

Val Asp Ile Val Asp Arg Asp Val Trp Ala Arg
1               5                   10
```

```
<210> SEQ ID NO 306
<211> LENGTH: 14
<212> TYPE: PRT
<213> ORGANISM: Staphylococcus aureus

<400> SEQUENCE: 306

Leu Lys Pro Asp Leu Ile Ile Ala Asp Ser Ser Arg His Lys
1               5                   10

<210> SEQ ID NO 307
<211> LENGTH: 18
<212> TYPE: PRT
<213> ORGANISM: Staphylococcus aureus

<400> SEQUENCE: 307

Gly Pro Tyr Leu Gln Leu Asp Thr Glu His Leu Ala Asp Leu Asn Pro
1               5                   10                  15

Glu Arg

<210> SEQ ID NO 308
<211> LENGTH: 22
<212> TYPE: PRT
<213> ORGANISM: Staphylococcus aureus

<400> SEQUENCE: 308

Ala Gly Leu Leu Ala His Pro Asn Tyr Ser Tyr Val Gly Gln Phe Leu
1               5                   10                  15

Asn Glu Leu Gly Phe Lys
            20

<210> SEQ ID NO 309
<211> LENGTH: 27
<212> TYPE: PRT
<213> ORGANISM: Staphylococcus aureus

<400> SEQUENCE: 309

Ile Val Val Leu Glu Tyr Ser Phe Ala Asp Ala Leu Ala Ala Leu Asp
1               5                   10                  15

Val Lys Pro Val Gly Ile Ala Asp Asp Gly Lys
            20                  25

<210> SEQ ID NO 310
<211> LENGTH: 28
<212> TYPE: PRT
<213> ORGANISM: Staphylococcus aureus

<400> SEQUENCE: 310

Ile Val Val Leu Glu Tyr Ser Phe Ala Asp Ala Leu Ala Ala Leu Asp
1               5                   10                  15

Val Lys Pro Val Gly Ile Ala Asp Asp Gly Lys Lys
            20                  25

<210> SEQ ID NO 311
<211> LENGTH: 9
<212> TYPE: PRT
<213> ORGANISM: Staphylococcus aureus

<400> SEQUENCE: 311

Ala Ala Ala Ile Asp Leu Ala Gly Arg
1               5

<210> SEQ ID NO 312
<211> LENGTH: 9
```

```
<212> TYPE: PRT
<213> ORGANISM: Staphylococcus aureus
<220> FEATURE:
<221> NAME/KEY: MOD_RES
<222> LOCATION: (8)..(8)
<223> OTHER INFORMATION: Oxidized Met

<400> SEQUENCE: 312

Asn Ile Glu Ala Asp Thr Gly Met Arg
1               5

<210> SEQ ID NO 313
<211> LENGTH: 10
<212> TYPE: PRT
<213> ORGANISM: Staphylococcus aureus

<400> SEQUENCE: 313

Val Val Asp Ala Asn Ile Ala Ala Gln Arg
1               5                   10

<210> SEQ ID NO 314
<211> LENGTH: 9
<212> TYPE: PRT
<213> ORGANISM: Staphylococcus aureus

<400> SEQUENCE: 314

Ala Asp Ile Asp Leu Pro Phe Glu Arg
1               5

<210> SEQ ID NO 315
<211> LENGTH: 13
<212> TYPE: PRT
<213> ORGANISM: Staphylococcus aureus

<400> SEQUENCE: 315

Leu Val Gly Gly Ala Gly Glu Glu Thr Ile Ile Ala Arg
1               5                   10

<210> SEQ ID NO 316
<211> LENGTH: 13
<212> TYPE: PRT
<213> ORGANISM: Staphylococcus aureus

<400> SEQUENCE: 316

Ala Met Ala Val Ala Thr Glu Gln Glu Met Lys Ala Arg
1               5                   10

<210> SEQ ID NO 317
<211> LENGTH: 14
<212> TYPE: PRT
<213> ORGANISM: Staphylococcus aureus

<400> SEQUENCE: 317

His His Thr Glu Val Leu Glu Asn Pro Asp Asn Ile Ser Lys
1               5                   10

<210> SEQ ID NO 318
<211> LENGTH: 17
<212> TYPE: PRT
<213> ORGANISM: Staphylococcus aureus

<400> SEQUENCE: 318

Val Val Glu Ala Glu Ser Glu Val Pro Leu Ala Met Ala Glu Ala Leu
1               5                   10                  15

Arg
```

```
<210> SEQ ID NO 319
<211> LENGTH: 18
<212> TYPE: PRT
<213> ORGANISM: Staphylococcus aureus

<400> SEQUENCE: 319

Val Ile Glu Thr Pro Phe Ile Ala Gly Val Ala Met Asn Gly Ile Glu
1               5                   10                  15

Val Lys

<210> SEQ ID NO 320
<211> LENGTH: 22
<212> TYPE: PRT
<213> ORGANISM: Staphylococcus aureus

<400> SEQUENCE: 320

Ala Gly Leu Ala Leu Thr Thr Asn Gln Leu Glu Ser His Tyr Leu Ala
1               5                   10                  15

Gly Gly Asn Val Asp Arg
            20

<210> SEQ ID NO 321
<211> LENGTH: 27
<212> TYPE: PRT
<213> ORGANISM: Staphylococcus aureus

<400> SEQUENCE: 321

Thr Val Leu Ser Lys Gly Leu Asp Ser Gly Thr Ala Phe Glu Ile Leu
1               5                   10                  15

Ser Ile Asp Ile Ala Asp Val Asp Ile Ser Lys
            20                  25

<210> SEQ ID NO 322
<211> LENGTH: 32
<212> TYPE: PRT
<213> ORGANISM: Staphylococcus aureus

<400> SEQUENCE: 322

Ala Gly Leu Ala Leu Thr Thr Asn Gln Leu Glu Ser His Tyr Leu Ala
1               5                   10                  15

Gly Gly Asn Val Asp Arg Val Val Asp Ala Asn Ile Ala Ala Gln Arg
            20                  25                  30

<210> SEQ ID NO 323
<211> LENGTH: 5
<212> TYPE: PRT
<213> ORGANISM: Staphylococcus aureus

<400> SEQUENCE: 323

Ala Asp Tyr Glu Lys
1               5

<210> SEQ ID NO 324
<211> LENGTH: 7
<212> TYPE: PRT
<213> ORGANISM: Staphylococcus aureus

<400> SEQUENCE: 324

Tyr Ile Ala Gln Leu Glu Lys
1               5
```

```
<210> SEQ ID NO 325
<211> LENGTH: 8
<212> TYPE: PRT
<213> ORGANISM: Staphylococcus aureus

<400> SEQUENCE: 325

Gln Gly Thr Pro Glu Gln Met Arg
1               5

<210> SEQ ID NO 326
<211> LENGTH: 10
<212> TYPE: PRT
<213> ORGANISM: Staphylococcus aureus

<400> SEQUENCE: 326

Ala Leu Glu Gln Ala Gly Lys Ser Leu Lys
1               5                   10

<210> SEQ ID NO 327
<211> LENGTH: 11
<212> TYPE: PRT
<213> ORGANISM: Staphylococcus aureus

<400> SEQUENCE: 327

His Leu Leu Val Glu Thr Ser Val Asp Lys Lys
1               5                   10

<210> SEQ ID NO 328
<211> LENGTH: 13
<212> TYPE: PRT
<213> ORGANISM: Staphylococcus aureus

<400> SEQUENCE: 328

Asp Ile Phe Gly Glu Val Tyr Thr Asp Ser Ile Gly Lys
1               5                   10

<210> SEQ ID NO 329
<211> LENGTH: 12
<212> TYPE: PRT
<213> ORGANISM: Staphylococcus aureus

<400> SEQUENCE: 329

Thr Ile Gln Gln Thr Phe Ile Asp Asn Asp Lys Lys
1               5                   10

<210> SEQ ID NO 330
<211> LENGTH: 13
<212> TYPE: PRT
<213> ORGANISM: Staphylococcus aureus

<400> SEQUENCE: 330

Val Val Thr Thr Asn Ser Ile Leu Tyr Asp Met Ala Lys
1               5                   10

<210> SEQ ID NO 331
<211> LENGTH: 14
<212> TYPE: PRT
<213> ORGANISM: Staphylococcus aureus

<400> SEQUENCE: 331

Lys Asp Ile Phe Gly Glu Val Tyr Thr Asp Ser Ile Gly Lys
1               5                   10

<210> SEQ ID NO 332
<211> LENGTH: 14
```

<212> TYPE: PRT
<213> ORGANISM: Staphylococcus aureus

<400> SEQUENCE: 332

Asp Val Lys Pro Ile Tyr Leu Asn Gly Glu Glu Gly Asn Lys
1               5                   10

<210> SEQ ID NO 333
<211> LENGTH: 14
<212> TYPE: PRT
<213> ORGANISM: Staphylococcus aureus

<400> SEQUENCE: 333

Gln Asp Pro His Ala Trp Leu Ser Leu Asp Asn Gly Ile Lys
1               5                   10

<210> SEQ ID NO 334
<211> LENGTH: 16
<212> TYPE: PRT
<213> ORGANISM: Staphylococcus aureus

<400> SEQUENCE: 334

Asp Val Lys Pro Ile Tyr Leu Asn Gly Glu Glu Gly Asn Lys Asp Lys
1               5                   10                  15

<210> SEQ ID NO 335
<211> LENGTH: 16
<212> TYPE: PRT
<213> ORGANISM: Staphylococcus aureus

<400> SEQUENCE: 335

Asp Lys Gln Asp Pro His Ala Trp Leu Ser Leu Asp Asn Gly Ile Lys
1               5                   10                  15

<210> SEQ ID NO 336
<211> LENGTH: 16
<212> TYPE: PRT
<213> ORGANISM: Staphylococcus aureus

<400> SEQUENCE: 336

Gln Tyr Gly Ile Thr Pro Gly Tyr Ile Trp Glu Ile Asn Thr Glu Lys
1               5                   10                  15

<210> SEQ ID NO 337
<211> LENGTH: 20
<212> TYPE: PRT
<213> ORGANISM: Staphylococcus aureus

<400> SEQUENCE: 337

Val Ile Ala Val Ser Lys Asp Val Lys Pro Ile Tyr Leu Asn Gly Glu
1               5                   10                  15

Glu Gly Asn Lys
            20

<210> SEQ ID NO 338
<211> LENGTH: 23
<212> TYPE: PRT
<213> ORGANISM: Staphylococcus aureus

<400> SEQUENCE: 338

Leu Thr Asp Ala Asp Val Ile Leu Tyr Asn Gly Leu Asn Leu Glu Thr
1               5                   10                  15

Gly Asn Gly Trp Phe Glu Lys
            20

```
<210> SEQ ID NO 339
<211> LENGTH: 27
<212> TYPE: PRT
<213> ORGANISM: Staphylococcus aureus

<400> SEQUENCE: 339

Asn Val Gly Gly Asp Asn Val Asp Ile His Ser Ile Val Pro Val Gly
1               5                   10                  15

Gln Asp Pro His Glu Tyr Glu Val Lys Pro Lys
            20                  25

<210> SEQ ID NO 340
<211> LENGTH: 5
<212> TYPE: PRT
<213> ORGANISM: Staphylococcus aureus

<400> SEQUENCE: 340

Ala Asp Tyr Glu Lys
1               5

<210> SEQ ID NO 341
<211> LENGTH: 7
<212> TYPE: PRT
<213> ORGANISM: Staphylococcus aureus

<400> SEQUENCE: 341

Tyr Ile Ala Gln Leu Glu Lys
1               5

<210> SEQ ID NO 342
<211> LENGTH: 11
<212> TYPE: PRT
<213> ORGANISM: Staphylococcus aureus

<400> SEQUENCE: 342

His Leu Leu Val Glu Thr Ser Val Asp Lys Lys
1               5                   10

<210> SEQ ID NO 343
<211> LENGTH: 13
<212> TYPE: PRT
<213> ORGANISM: Staphylococcus aureus

<400> SEQUENCE: 343

Asp Ile Phe Gly Glu Val Tyr Thr Asp Ser Ile Gly Lys
1               5                   10

<210> SEQ ID NO 344
<211> LENGTH: 12
<212> TYPE: PRT
<213> ORGANISM: Staphylococcus aureus

<400> SEQUENCE: 344

Thr Ile Gln Gln Thr Phe Ile Asp Asn Asp Lys Lys
1               5                   10

<210> SEQ ID NO 345
<211> LENGTH: 13
<212> TYPE: PRT
<213> ORGANISM: Staphylococcus aureus

<400> SEQUENCE: 345

Val Val Thr Thr Asn Ser Ile Leu Tyr Asp Met Ala Lys
```

<210> SEQ ID NO 346
<211> LENGTH: 14
<212> TYPE: PRT
<213> ORGANISM: Staphylococcus aureus

<400> SEQUENCE: 346

Asp Val Lys Pro Ile Tyr Leu Asn Gly Glu Glu Gly Asn Lys
1               5                   10

<210> SEQ ID NO 347
<211> LENGTH: 14
<212> TYPE: PRT
<213> ORGANISM: Staphylococcus aureus

<400> SEQUENCE: 347

Gln Asp Pro His Ala Trp Leu Ser Leu Asp Asn Gly Ile Lys
1               5                   10

<210> SEQ ID NO 348
<211> LENGTH: 16
<212> TYPE: PRT
<213> ORGANISM: Staphylococcus aureus

<400> SEQUENCE: 348

Asp Val Lys Pro Ile Tyr Leu Asn Gly Glu Glu Gly Asn Lys Asp Lys
1               5                   10                  15

<210> SEQ ID NO 349
<211> LENGTH: 16
<212> TYPE: PRT
<213> ORGANISM: Staphylococcus aureus

<400> SEQUENCE: 349

Asp Lys Gln Asp Pro His Ala Trp Leu Ser Leu Asp Asn Gly Ile Lys
1               5                   10                  15

<210> SEQ ID NO 350
<211> LENGTH: 16
<212> TYPE: PRT
<213> ORGANISM: Staphylococcus aureus

<400> SEQUENCE: 350

Gln Tyr Gly Ile Thr Pro Gly Tyr Ile Trp Glu Ile Asn Thr Glu Lys
1               5                   10                  15

<210> SEQ ID NO 351
<211> LENGTH: 23
<212> TYPE: PRT
<213> ORGANISM: Staphylococcus aureus

<400> SEQUENCE: 351

Leu Thr Asp Ala Asp Val Ile Leu Tyr Asn Gly Leu Asn Leu Glu Thr
1               5                   10                  15

Gly Asn Gly Trp Phe Glu Lys
            20

<210> SEQ ID NO 352
<211> LENGTH: 27
<212> TYPE: PRT
<213> ORGANISM: Staphylococcus aureus

<400> SEQUENCE: 352

```
Asn Val Gly Gly Asp Asn Val Asp Ile His Ser Ile Val Pro Val Gly
1               5                   10                  15

Gln Asp Pro His Glu Tyr Glu Val Lys Pro Lys
            20                  25
```

<210> SEQ ID NO 353
<211> LENGTH: 6
<212> TYPE: PRT
<213> ORGANISM: Staphylococcus aureus

<400> SEQUENCE: 353

```
Ile Ile Gly Asp Tyr Arg
1               5
```

<210> SEQ ID NO 354
<211> LENGTH: 6
<212> TYPE: PRT
<213> ORGANISM: Staphylococcus aureus

<400> SEQUENCE: 354

```
Ile Phe Thr Asp Tyr Arg
1               5
```

<210> SEQ ID NO 355
<211> LENGTH: 9
<212> TYPE: PRT
<213> ORGANISM: Staphylococcus aureus

<400> SEQUENCE: 355

```
Glu Gln Gln Leu Asp Val Ile Ser Arg
1               5
```

<210> SEQ ID NO 356
<211> LENGTH: 10
<212> TYPE: PRT
<213> ORGANISM: Staphylococcus aureus

<400> SEQUENCE: 356

```
Leu Arg Glu Glu Leu Ser Glu Gln Tyr Arg
1               5                   10
```

<210> SEQ ID NO 357
<211> LENGTH: 20
<212> TYPE: PRT
<213> ORGANISM: Staphylococcus aureus

<400> SEQUENCE: 357

```
Thr Met Ala Thr Gly Ile Ala Gly Leu Ser Val Ala Ala Asp Ser Leu
1               5                   10                  15

Ser Ala Ile Lys
            20
```

<210> SEQ ID NO 358
<211> LENGTH: 19
<212> TYPE: PRT
<213> ORGANISM: Staphylococcus aureus

<400> SEQUENCE: 358

```
Ala Gly Val Ile Thr Glu Ser Glu Val Gln Glu Ile Ile Asp His Phe
1               5                   10                  15

Ile Met Lys
```

<210> SEQ ID NO 359

```
<211> LENGTH: 23
<212> TYPE: PRT
<213> ORGANISM: Staphylococcus aureus

<400> SEQUENCE: 359

Phe Leu His Ser Leu Asp Asn Leu Gly Pro Ala Pro Glu Pro Asn Leu
1               5                   10                  15

Thr Val Leu Trp Ser Val Arg
            20

<210> SEQ ID NO 360
<211> LENGTH: 24
<212> TYPE: PRT
<213> ORGANISM: Staphylococcus aureus

<400> SEQUENCE: 360

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 361
<211> LENGTH: 25
<212> TYPE: PRT
<213> ORGANISM: Staphylococcus aureus

<400> SEQUENCE: 361

Ser Gly Ala Gln Val Gly Pro Asn Phe Glu Gly Ile Asn Ser Glu Val
1               5                   10                  15

Leu Glu Tyr Asp Glu Val Phe Lys Lys
            20                  25

<210> SEQ ID NO 362
<211> LENGTH: 30
<212> TYPE: PRT
<213> ORGANISM: Staphylococcus aureus

<400> SEQUENCE: 362

Val Ala Ser Thr Ile Thr Ser His Asp Ala Gly Tyr Leu Asp Lys Asp
1               5                   10                  15

Leu Glu Thr Ile Val Gly Val Gln Thr Glu Lys Pro Phe Lys
            20                  25                  30

<210> SEQ ID NO 363
<211> LENGTH: 6
<212> TYPE: PRT
<213> ORGANISM: Staphylococcus aureus

<400> SEQUENCE: 363

Ile Phe Thr Asp Tyr Arg
1               5

<210> SEQ ID NO 364
<211> LENGTH: 15
<212> TYPE: PRT
<213> ORGANISM: Staphylococcus aureus

<400> SEQUENCE: 364

Asp Leu Glu Thr Ile Val Gly Val Gln Thr Glu Lys Pro Phe Lys
1               5                   10                  15

<210> SEQ ID NO 365
<211> LENGTH: 16
```

```
<212> TYPE: PRT
<213> ORGANISM: Staphylococcus aureus

<400> SEQUENCE: 365

Asp Leu Glu Thr Ile Val Gly Val Gln Thr Glu Lys Pro Phe Lys Arg
1               5                   10                  15

<210> SEQ ID NO 366
<211> LENGTH: 20
<212> TYPE: PRT
<213> ORGANISM: Staphylococcus aureus

<400> SEQUENCE: 366

Thr Met Ala Thr Gly Ile Ala Gly Leu Ser Val Ala Ala Asp Ser Leu
1               5                   10                  15

Ser Ala Ile Lys
            20

<210> SEQ ID NO 367
<211> LENGTH: 17
<212> TYPE: PRT
<213> ORGANISM: Staphylococcus aureus

<400> SEQUENCE: 367

Asn Glu Glu Gly Leu Val Val Asp Phe Glu Ile Glu Gly Asp Phe Pro
1               5                   10                  15

Lys

<210> SEQ ID NO 368
<211> LENGTH: 23
<212> TYPE: PRT
<213> ORGANISM: Staphylococcus aureus

<400> SEQUENCE: 368

Phe Leu His Ser Leu Asp Asn Leu Gly Pro Ala Pro Glu Pro Asn Leu
1               5                   10                  15

Thr Val Leu Trp Ser Val Arg
            20

<210> SEQ ID NO 369
<211> LENGTH: 24
<212> TYPE: PRT
<213> ORGANISM: Staphylococcus aureus

<400> SEQUENCE: 369

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 370
<211> LENGTH: 26
<212> TYPE: PRT
<213> ORGANISM: Staphylococcus aureus

<400> SEQUENCE: 370

Glu Phe Ile Gln Leu Asn Tyr Thr Leu Tyr Glu Gly Asn Asp Ser Phe
1               5                   10                  15

Leu Ala Gly Pro Thr Glu Ala Thr Ser Lys
            20                  25

<210> SEQ ID NO 371
```

```
<211> LENGTH: 6
<212> TYPE: PRT
<213> ORGANISM: Staphylococcus aureus

<400> SEQUENCE: 371

Ile Val Lys Phe Ala Arg
1               5

<210> SEQ ID NO 372
<211> LENGTH: 10
<212> TYPE: PRT
<213> ORGANISM: Staphylococcus aureus

<400> SEQUENCE: 372

Thr Leu Leu Tyr Ala Ile Asn Gly Gly Lys
1               5                   10

<210> SEQ ID NO 373
<211> LENGTH: 9
<212> TYPE: PRT
<213> ORGANISM: Staphylococcus aureus

<400> SEQUENCE: 373

Glu Gln Gln Leu Asp Val Ile Ser Arg
1               5

<210> SEQ ID NO 374
<211> LENGTH: 11
<212> TYPE: PRT
<213> ORGANISM: Staphylococcus aureus

<400> SEQUENCE: 374

Val Asp Asp Ile Ala Val Asp Leu Val Glu Arg
1               5                   10

<210> SEQ ID NO 375
<211> LENGTH: 11
<212> TYPE: PRT
<213> ORGANISM: Staphylococcus aureus

<400> SEQUENCE: 375

Leu Pro Asp Asn Phe Lys Thr Tyr Cys Ala Lys
1               5                   10

<210> SEQ ID NO 376
<211> LENGTH: 14
<212> TYPE: PRT
<213> ORGANISM: Staphylococcus aureus

<400> SEQUENCE: 376

Asp Gln Lys Gly Ala Leu Ser Ser Leu Ser Ser Val Ala Lys
1               5                   10

<210> SEQ ID NO 377
<211> LENGTH: 15
<212> TYPE: PRT
<213> ORGANISM: Staphylococcus aureus

<400> SEQUENCE: 377

Val Ala Ser Thr Ile Thr Ser His Asp Ala Gly Tyr Leu Asp Lys
1               5                   10                  15

<210> SEQ ID NO 378
<211> LENGTH: 15
<212> TYPE: PRT
```

<213> ORGANISM: Staphylococcus aureus

<400> SEQUENCE: 378

Asp Leu Glu Thr Ile Val Gly Val Gln Thr Glu Lys Pro Phe Lys
1               5                   10                  15

<210> SEQ ID NO 379
<211> LENGTH: 17
<212> TYPE: PRT
<213> ORGANISM: Staphylococcus aureus

<400> SEQUENCE: 379

Met Ser Ile Lys Thr Ser Ser Ile Gln Tyr Glu Asn Asp Asp Ile Met
1               5                   10                  15

Arg

<210> SEQ ID NO 380
<211> LENGTH: 23
<212> TYPE: PRT
<213> ORGANISM: Staphylococcus aureus

<400> SEQUENCE: 380

Phe Leu His Ser Leu Asp Asn Leu Gly Pro Ala Pro Glu Pro Asn Leu
1               5                   10                  15

Thr Val Leu Trp Ser Val Arg
            20

<210> SEQ ID NO 381
<211> LENGTH: 24
<212> TYPE: PRT
<213> ORGANISM: Staphylococcus aureus

<400> SEQUENCE: 381

Ser Gly Ala Gln Val Gly Pro Asn Phe Glu Gly Ile Asn Ser Glu Val
1               5                   10                  15

Leu Glu Tyr Asp Glu Val Phe Lys
            20

<210> SEQ ID NO 382
<211> LENGTH: 7
<212> TYPE: PRT
<213> ORGANISM: Staphylococcus aureus

<400> SEQUENCE: 382

Thr Phe Tyr Pro Glu Ala Arg
1               5

<210> SEQ ID NO 383
<211> LENGTH: 8
<212> TYPE: PRT
<213> ORGANISM: Staphylococcus aureus

<400> SEQUENCE: 383

Gln Phe Trp Gly His Leu Val Lys
1               5

<210> SEQ ID NO 384
<211> LENGTH: 9
<212> TYPE: PRT
<213> ORGANISM: Staphylococcus aureus

<400> SEQUENCE: 384

Trp Ile Pro Leu Met Met Lys Gly Arg

```
<210> SEQ ID NO 385
<211> LENGTH: 10
<212> TYPE: PRT
<213> ORGANISM: Staphylococcus aureus

<400> SEQUENCE: 385

Val Ile Asn Glu Glu Phe Glu Ile Ser Lys
1               5                   10

<210> SEQ ID NO 386
<211> LENGTH: 10
<212> TYPE: PRT
<213> ORGANISM: Staphylococcus aureus

<400> SEQUENCE: 386

Tyr Ser Phe Asp Gln Val Ile Met Thr Lys
1               5                   10

<210> SEQ ID NO 387
<211> LENGTH: 11
<212> TYPE: PRT
<213> ORGANISM: Staphylococcus aureus

<400> SEQUENCE: 387

Asn Glu Asp Trp Gln Leu Tyr Thr Ala Gly Lys
1               5                   10

<210> SEQ ID NO 388
<211> LENGTH: 13
<212> TYPE: PRT
<213> ORGANISM: Staphylococcus aureus

<400> SEQUENCE: 388

Thr Leu Leu Phe Gly Pro Phe Ala Asn Val Gly Pro Lys
1               5                   10

<210> SEQ ID NO 389
<211> LENGTH: 13
<212> TYPE: PRT
<213> ORGANISM: Staphylococcus aureus
<220> FEATURE:
<221> NAME/KEY: MOD_RES
<222> LOCATION: (9)..(9)
<223> OTHER INFORMATION: Oxidized Met

<400> SEQUENCE: 389

Gly Arg Glu Asp Asn Pro Gly Ile Met Ala Ala Ser Lys
1               5                   10

<210> SEQ ID NO 390
<211> LENGTH: 12
<212> TYPE: PRT
<213> ORGANISM: Staphylococcus aureus

<400> SEQUENCE: 390

Leu Asp Arg Pro Ala Ile Glu Ser Ser Asn Glu Arg
1               5                   10

<210> SEQ ID NO 391
<211> LENGTH: 12
<212> TYPE: PRT
<213> ORGANISM: Staphylococcus aureus

<400> SEQUENCE: 391
```

Asn Glu Asp Trp Gln Leu Tyr Thr Ala Gly Lys Arg
1               5                   10

<210> SEQ ID NO 392
<211> LENGTH: 14
<212> TYPE: PRT
<213> ORGANISM: Staphylococcus aureus

<400> SEQUENCE: 392

Ile Asp Glu Gly Thr Asp Val Asn Phe Gly Glu Leu Thr Arg
1               5                   10

<210> SEQ ID NO 393
<211> LENGTH: 13
<212> TYPE: PRT
<213> ORGANISM: Staphylococcus aureus

<400> SEQUENCE: 393

Glu Phe Ile Asn Pro Leu Pro His Ile Ser Tyr Val Arg
1               5                   10

<210> SEQ ID NO 394
<211> LENGTH: 13
<212> TYPE: PRT
<213> ORGANISM: Staphylococcus aureus

<400> SEQUENCE: 394

Glu Ile Glu Pro Asp Trp Asn Ile His Val Tyr Glu Arg
1               5                   10

<210> SEQ ID NO 395
<211> LENGTH: 16
<212> TYPE: PRT
<213> ORGANISM: Staphylococcus aureus
<220> FEATURE:
<221> NAME/KEY: MOD_RES
<222> LOCATION: (8)..(8)
<223> OTHER INFORMATION: Oxidized Met

<400> SEQUENCE: 395

Glu Pro Pro Gly Thr Pro Pro Met Thr Val Pro His Leu Asp Thr Arg
1               5                   10                  15

<210> SEQ ID NO 396
<211> LENGTH: 20
<212> TYPE: PRT
<213> ORGANISM: Staphylococcus aureus

<400> SEQUENCE: 396

Gln Val Thr Asp Tyr Val Phe Ile Gly Ala Gly Gly Ala Ile Pro
1               5                   10                  15

Leu Leu Gln Lys
            20

<210> SEQ ID NO 397
<211> LENGTH: 20
<212> TYPE: PRT
<213> ORGANISM: Staphylococcus aureus
<220> FEATURE:
<221> NAME/KEY: MOD_RES
<222> LOCATION: (12)..(12)
<223> OTHER INFORMATION: Oxidized Met

<400> SEQUENCE: 397

Val Tyr Gly Lys Glu Pro Pro Gly Thr Pro Pro Met Thr Val Pro His

```
<210> SEQ ID NO 398
<211> LENGTH: 26
<212> TYPE: PRT
<213> ORGANISM: Staphylococcus aureus

<400> SEQUENCE: 398

His Leu Gly Gly Phe Pro Ile Ser Gly Gln Phe Leu Ala Cys Thr Asn
1               5                   10                  15

Pro Gln Val Ile Glu Gln His Asp Ala Lys
            20                  25

<210> SEQ ID NO 399
<211> LENGTH: 9
<212> TYPE: PRT
<213> ORGANISM: Staphylococcus aureus

<400> SEQUENCE: 399

Ala Ala Ala Ile Asp Leu Ala Gly Arg
1               5

<210> SEQ ID NO 400
<211> LENGTH: 10
<212> TYPE: PRT
<213> ORGANISM: Staphylococcus aureus

<400> SEQUENCE: 400

Val Val Asp Ala Asn Ile Ala Ala Gln Arg
1               5                   10

<210> SEQ ID NO 401
<211> LENGTH: 9
<212> TYPE: PRT
<213> ORGANISM: Staphylococcus aureus

<400> SEQUENCE: 401

Ala Asp Ile Asp Leu Pro Phe Glu Arg
1               5

<210> SEQ ID NO 402
<211> LENGTH: 13
<212> TYPE: PRT
<213> ORGANISM: Staphylococcus aureus

<400> SEQUENCE: 402

Leu Val Gly Gly Ala Gly Glu Glu Thr Ile Ile Ala Arg
1               5                   10

<210> SEQ ID NO 403
<211> LENGTH: 14
<212> TYPE: PRT
<213> ORGANISM: Staphylococcus aureus

<400> SEQUENCE: 403

His His Thr Glu Val Leu Glu Asn Pro Asp Asn Ile Ser Lys
1               5                   10

<210> SEQ ID NO 404
<211> LENGTH: 17
<212> TYPE: PRT
<213> ORGANISM: Staphylococcus aureus
```

(also above: continuation of previous sequence)

```
Leu Asp Thr Arg
            20
```

<400> SEQUENCE: 404

Val Val Glu Ala Glu Ser Glu Val Pro Leu Ala Met Ala Glu Ala Leu
1               5                   10                  15

Arg

<210> SEQ ID NO 405
<211> LENGTH: 22
<212> TYPE: PRT
<213> ORGANISM: Staphylococcus aureus
<220> FEATURE:
<221> NAME/KEY: MOD_RES
<222> LOCATION: (17)..(17)
<223> OTHER INFORMATION: Oxidized Met

<400> SEQUENCE: 405

Ala Ala Ala Ile Asp Leu Ala Gly Arg Asp Val Leu Glu Ala Val Gln
1               5                   10                  15

Met Ser Val Asn Pro Lys
            20

<210> SEQ ID NO 406
<211> LENGTH: 22
<212> TYPE: PRT
<213> ORGANISM: Staphylococcus aureus

<400> SEQUENCE: 406

Ala Gly Leu Ala Leu Thr Thr Asn Gln Leu Glu Ser His Tyr Leu Ala
1               5                   10                  15

Gly Gly Asn Val Asp Arg
            20

<210> SEQ ID NO 407
<211> LENGTH: 27
<212> TYPE: PRT
<213> ORGANISM: Staphylococcus aureus

<400> SEQUENCE: 407

Thr Val Leu Ser Lys Gly Leu Asp Ser Gly Thr Ala Phe Glu Ile Leu
1               5                   10                  15

Ser Ile Asp Ile Ala Asp Val Asp Ile Ser Lys
            20                  25

<210> SEQ ID NO 408
<211> LENGTH: 6
<212> TYPE: PRT
<213> ORGANISM: Staphylococcus aureus

<400> SEQUENCE: 408

Phe Val Phe His Gly Arg
1               5

<210> SEQ ID NO 409
<211> LENGTH: 8
<212> TYPE: PRT
<213> ORGANISM: Staphylococcus aureus

<400> SEQUENCE: 409

Asp Gly Phe Asn Asn Ile Glu Arg
1               5

<210> SEQ ID NO 410
<211> LENGTH: 13

```
<212> TYPE: PRT
<213> ORGANISM: Staphylococcus aureus

<400> SEQUENCE: 410

Gly His Val Tyr Asn Gly Ile Ser Gly Gly Gln Phe Lys
1               5                   10

<210> SEQ ID NO 411
<211> LENGTH: 12
<212> TYPE: PRT
<213> ORGANISM: Staphylococcus aureus

<400> SEQUENCE: 411

Tyr Thr Pro Thr Ser Ile Leu Tyr Phe Asn Pro Lys
1               5                   10

<210> SEQ ID NO 412
<211> LENGTH: 13
<212> TYPE: PRT
<213> ORGANISM: Staphylococcus aureus

<400> SEQUENCE: 412

Gln Leu Ala Glu Asp Leu Gln Lys His Leu Gly Ala Lys
1               5                   10

<210> SEQ ID NO 413
<211> LENGTH: 15
<212> TYPE: PRT
<213> ORGANISM: Staphylococcus aureus
<220> FEATURE:
<221> NAME/KEY: MOD_RES
<222> LOCATION: (9)..(9)
<223> OTHER INFORMATION: Oxidized Met

<400> SEQUENCE: 413

Asn His Ser Glu Tyr Val Thr Asp Met Arg Leu Ile Gly Ile Arg
1               5                   10                  15

<210> SEQ ID NO 414
<211> LENGTH: 16
<212> TYPE: PRT
<213> ORGANISM: Staphylococcus aureus

<400> SEQUENCE: 414

Asp Leu Pro Pro Met Glu Gln Val Phe Asp Thr Leu Asp Leu Asp Lys
1               5                   10                  15

<210> SEQ ID NO 415
<211> LENGTH: 16
<212> TYPE: PRT
<213> ORGANISM: Staphylococcus aureus
<220> FEATURE:
<221> NAME/KEY: MISC_FEATURE
<223> OTHER INFORMATION: One of the two Mets in this sequence is
      oxidized.
<220> FEATURE:
<221> NAME/KEY: MOD_RES
<222> LOCATION: (6)..(6)
<223> OTHER INFORMATION: This residue may or may not be oxidized
<220> FEATURE:
<221> NAME/KEY: MOD_RES
<222> LOCATION: (9)..(9)
<223> OTHER INFORMATION: This residue may or may not be oxidized

<400> SEQUENCE: 415

Ile Arg Pro Glu Asp Met His Ile Met Ala Asn Ile Phe Leu Pro Lys
1               5                   10                  15
```

```
<210> SEQ ID NO 416
<211> LENGTH: 17
<212> TYPE: PRT
<213> ORGANISM: Staphylococcus aureus

<400> SEQUENCE: 416

Arg Ile Arg Pro Glu Asp Met His Ile Met Ala Asn Ile Phe Leu Pro
1               5                   10                  15

Lys

<210> SEQ ID NO 417
<211> LENGTH: 20
<212> TYPE: PRT
<213> ORGANISM: Staphylococcus aureus

<400> SEQUENCE: 417

Ile Ser His Leu Val Leu Thr Arg Thr Gly Leu Tyr Ile Ile Asp Ser
1               5                   10                  15

Gln Leu Leu Lys
            20
```